(12) United States Patent
Sheehan et al.

(10) Patent No.: US 9,180,191 B2
(45) Date of Patent: Nov. 10, 2015

(54) TREATMENT OF SUICIDAL IDEATION OR BEHAVIOR USING INHIBITORS OF NICOTINIC ACETYLCHOLINE RECEPTORS

(75) Inventors: David Vincent Sheehan, Lutz, FL (US); Roland Douglas Shytle, Largo, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 13/502,239

(22) PCT Filed: Oct. 15, 2010

(86) PCT No.: PCT/US2010/052949
§ 371 (c)(1),
(2), (4) Date: Jul. 3, 2012

(87) PCT Pub. No.: WO2011/047341
PCT Pub. Date: Apr. 21, 2011

(65) Prior Publication Data
US 2012/0269906 A1    Oct. 25, 2012

Related U.S. Application Data

(60) Provisional application No. 61/252,343, filed on Oct. 16, 2009.

(51) Int. Cl.
| | | |
|---|---|---|
| *A61K 8/41* | (2006.01) |
| *C07K 14/705* | (2006.01) |
| *A61K 45/06* | (2006.01) |
| *A61K 31/407* | (2006.01) |
| *A61K 31/55* | (2006.01) |
| *A61K 31/5513* | (2006.01) |
| *A61K 33/14* | (2006.01) |

(52) U.S. Cl.
CPC ............... *A61K 45/06* (2013.01); *A61K 31/407* (2013.01); *A61K 31/55* (2013.01); *A61K 31/5513* (2013.01); *A61K 33/14* (2013.01)

(58) Field of Classification Search
CPC ............... A61K 31/5513; A61K 45/06; C12Q 2600/156; G01N 33/6896
See application file for complete search history.

(56) References Cited

U.S. PATENT DOCUMENTS

| | | | |
|---|---|---|---|
| 5,952,339 A | 9/1999 | Bencherif et al. |
| 5,981,193 A | 11/1999 | Harpold et al. |
| 6,034,079 A | 3/2000 | Sanberg et al. |
| 6,121,289 A | 9/2000 | Houdi |
| 6,503,922 B2 | 1/2003 | Crooks et al. |
| 6,734,215 B2 | 5/2004 | Shytle et al. |
| 6,780,871 B2 | 8/2004 | Glick et al. |
| 6,979,698 B1 | 12/2005 | Sandberg et al. |
| 7,101,916 B2 | 9/2006 | Shytle et al. |
| 8,026,283 B2 | 9/2011 | Shytle et al. |
| 2002/0099069 A1 | 7/2002 | Crooks et al. |
| 2005/0026842 A1 | 2/2005 | Simon |
| 2006/0084692 A1 | 4/2006 | Wong et al. |
| 2006/0148675 A1 | 7/2006 | Cooke et al. |
| 2006/0211686 A1 | 9/2006 | Kohlhaas et al. |
| 2006/0280818 A1 | 12/2006 | Palu et al. |
| 2008/0058345 A1* | 3/2008 | George et al. ............ 514/254.06 |
| 2008/0287490 A1 | 11/2008 | Crooks et al. |

FOREIGN PATENT DOCUMENTS

WO    WO 2007-100430    9/2007

OTHER PUBLICATIONS

Thase, "Quetiapine monotherapy for bipolar depression", Neuropsychiatric Disease and Treatment, 2008:4(I), 11-21.*
FDA, "FDA Proposes New Warnings About Suicidal Thinking, Behavior in Young Adults Who Take Antidepressant Medications", FDA News Release, 2007.*
Rush University Medical Center, "Treatment of Depression with Quetiapine", ClinicalTrials.gov, 2007.*
WebMD, "Types of Depression", WebMD, http://www.webmd.com/depression/guide/depression-types, 2008.*
Sun "Association of tryptophan hydroxylase gene polymorphism with depression, anxiety and comorbid depression and anxiety in a population based sample of postpartum Taiwanese women", Genes, Brain and Behavior, 3: 328-336, 2004.*
Shytle, "Comorbid Bipolar Disorder in Tourette's Syndrome Responds to the Nicotinic Receptor Antagonist Mecamylamine (Inversine)", Society of Biological Psychiatry, 1028-1031, 2000.*
Oquendo, "Prospective Study of Clinical Predictors of Suicidal Acts After a Major Depressive Episode in Patients With Major Depressive Disorder or Bipolar Disorder", Am J Psychiatry 161, 1433-1441, 2004.*
Ostacher et al., "The Relationship Between Smoking and Suicidal Behavior, Comorbidity, and Course of Illness in Bipolar Disorder", J Clin Psychiatry, 67:12, Dec. 2006.*
"Bipolar disorder", Oct. 28, 2005, webpage retrieved online at minddisorders.com [retrieved on Dec. 4, 2014]. Retrieved from the Internet: <URL: http://www.minddisorders.com/A-Br/Bipolar-disorder.html>.*
Shytle et al., "Mecamylamine (Inversine®): an old antihypertensive with new research directions", Journal of Human Hypertension, 16, 453-457, 2002.*
Angst, F et al., "Mortality of patients with mood disorders: follow-up over 34-38 years" *Journal of Affective Disorders*, 2002, 68(2):167-181.

(Continued)

*Primary Examiner* — Robert T Crow
*Assistant Examiner* — John P Nguyen
(74) *Attorney, Agent, or Firm* — Saliwanchik, Lloyd & Eisenschenk

(57) ABSTRACT

The invention concerns methods of treating suicidal ideation or behavior in a subject in need thereof, comprising decreasing endogenous nicotinic acetylcholine receptor (nAChR) activity in the subject; therapeutic packages for treating suicidal ideation or behavior; and methods for determining the efficacy of a treatment for suicidal ideation or behavior. In some embodiments, the treatment methods comprise administering to the subject an effective amount of an inhibitor of a nAChR, such as a lithium compound, mecamylamine, clozapine, or asenapine.

25 Claims, 8 Drawing Sheets

(56) References Cited

OTHER PUBLICATIONS

"Guidance for Industry Suicidality: Prospective Assessment of Occurrence in Clinical Trials" *U.S. Department of Health and Human Services, Food and Drug Administration, Center for Drug Evaluation and Research (CDER)*, Sep. 2010, pp. 1-15.

Baldessarini, RJ et al., "Effects of lithium treatment and its discontinuation on suicidal behavior in bipolar manic-depressive disorders" *Journal of Clinical Psychiatry*, 1990, 60(2):77-84. [abstract].

Baldessarini, RJ et al., "Treating the suicidal patient with biopolar disorder: Reducing suicide risk with lithium" *Annals of the New York Academy of Sciences*, 2001, 932:24-38. [abstract].

Barnes, TR, "A rating scale for drug-induced akathisia" *The British Journal of Psychiatry*, 1989, 154:672-676.

Bertrand, D et al., "Activation and blocking of neuronal nicotinic acetylcholine receptor reconstituted in *Xenopus* oocytes" *Proceedings of the National Academy of Sciences of the United States of America*, 1990, 87:1993-1997.

Bowden, CL et al., "A randomized, double-blind, placebo-controlled efficacy and safety study of quetiapine or lithium as monotherapy for mania in bipolar disorder" *Journal of Clinical Psychiatry*, 2005, 66(1):111-21. [abstract].

Calabrese, JR et al., "A Randomized, Double-Blind, Placebo-Controlled Trial of Quetiapine in the Treatment of Bipolar I or II Depression" *American Journal Psychiatry*, 2005, 162(7):1351-1360.

Ciapparelli, A et al., "Clozapine for Treatment Refractory Schizophrenia, Schizoaffective Disorder, and Psychotic Bipolar Disorder: A 24-Month Naturalistic Study" *Journal of Clinical Psychiatry*, 2000, 61(5):329-334.

Coric, V et al., "Sheehan Suicidality Tracking Scale (Sheehan-STS): Preliminary Results from a Multicenter Clinical Trial in Generalized Anxiety Disorder" *Psychiatry*, 2009, 6(1):26-31.

Corringer, P-J et al., "Critical Elements Determining Diversity in Agonist Binding and Desensitization of Neuronal Nicotinic Acetylcholine Receptors" *The Journal of Neuroscience*,1998, 18(2):648-657.

Delbello, MP et al., "A double-blind, randomized, placebo-controlled study of quetiapine as adjunctive treatment for adolescent mania" *Journal of the American Academy of Child and Adolescent Psychiatry*, 2002, 41(10):1216-23. [abstract].

Dwoskin, LP and Crooks, PA, "Competitive Neuronal Nicotinic Receptor Antagonists: A New Direction for Drug Discovery" *The Journal of Pharmacology and Experimental Therapeutics*, 2001, 298(2):395-402.

Emsley, RA et al., "Differential effect of quetiapine on depressive symptoms in patients with partially responsive schizophrenia" *Journal of Psychopharmacology*, 2003, 17(2):210-215.

Goodwin, FK et al., "Suicide Risk in Bipolar Disorder During Treatment With Lithium and Divalproex" *The Journal of the American Medical Association*, 2003, 290(11):1467-1473.

Gould, AL, "A New Approach to the Analysis of Clinical Drug Trials with Withdrawals" *Biometrics*, 1980, 36(4):721-727.

Houston, JP et al., "Reduced suicidal ideation in bipolar I disorder mixed-episode patients in a placebo-controlle trial of olanzapine combined with lithium or divalproex" *Journal Clinical Psychiatry*, 2006, 67(8):1246-1252. [abstract].

Keck, PE and McElroy, SL, "Redefining mood stabilization" *Journal of Affective Disorders*, 2003, 73:163-169.

Kessler, RC et al., "The epidemiology of DSM-III-R bipolar I disorder in a general population survey" *Psychological Medicine*, 1997, 27(5):1079-1089.

Khan, A et al., "Suicide Rates in Clinical Trials of SSRIs, Other Antidepressants, and Placebo: Analysis of FDA Reports" *Journal of the American Psychiatric Association*, 2003, 160(4):790-792.

Leisgen, C et al., "Patch-Clamp Methods and Protocols: The Roboocyte: Automated Electrophysiology Based on Xenopus Oocytes" *Methods in Molecular Biology*, 2007, 288:87-109.

Leon, AC et al., "Assessing impairment in patients with panic disorder: the Sheehan Disability Scale" *Social Psychiatry and Psychiatric Epidemiology*, 1992, 27(2):78-82. [abstract].

Mann, JJ et al., "The Neurobiology and Genetics of Suicide and Attempted Suicide: A Focus on the Serotonergic System" *Neuropsychopharmacology*, 2001, 24(5):467-477.

McElroy, SL and Keck, PE Jr, "Pharmacological agents for the treatment of acute bipolar mania" *Biological Psychiatry*, 2000, 48(6):539-557. [abstract].

Posner, K et al., "Columbia Classification Algorithm of Suicide Assessment (C-CASA): Classification of Suicidal Events in the FDA's Pediatric Suicidal Risk Analysis of Antidepressants" *Journal of the American Psychiatric Association*, 2007, 164(7):1035-1043.

Posner, K, "Suicidality Issues in Clinical Trials: Columbia Suicidal Adverse Event Identification in FDA Safety Analyses" *Division of Metabolism and Endocrinology Products Advisory Committee Meeting*, Jun. 13, 2007, pp. 1-28.

Roy, A et al., "Attempted Suicide Among Living Co-Twins of Twin Suicide Victims" *Journal of the American Psychiatric Association*, 1995, 152(7):1075-1076.

Roy, A, "Genetic and Biologic Risk Factors for Suicide in Depressive Disorders" Psychiatric Quarterly, 1993, 64(4):345-358.

Sachs, G et al., "Quetiapine with lithium or divalproex for the treatment of bipolar mania: a randomized, double-blind, placebo-controlled study" *Bipolar Disorders*, 2004, 6:213-223.

Sachs, GS et al., "Effectiveness of Adjunctive Antidepressant Treatment for Bipolar Depression" *The New England Journal of Medicine*, 2007, 356(17):1711-1722.

Sheehan, DV et al., "The Measurement of Disability" *International Clinical Psychopharmacology*, 1996, 11(3):89-95. [abstract].

Sheehan, DV et al., "The Mini International Neuropsychiatric Interview (M.I.N.I.): The Development and Validation of a Structured Diagnostric Psychiatric Interview" *Journal of Clinical Psychiatry*, 1998, 59(20):22-33. [abstract].

Shytle, RD et al., "Nicotinic acetylcholine receptors as targets for antidepressants" *Molecular Psychiatry*, 2002, 7:525-535.

Smulders, CJGM et al., "Block of Neuronal Nicotinic Acetylcholine Receptors by Organophosphate Insecticides" *Toxicological Sciences*, 2004, 82:545-554.

Spearing, MK et al., "Modification of the Clinical Global Impressions (CGI) scale for use in bipolar illness (BP): the CGI-BP" *Psychiatry Research*, 1997, 73:159-171.

Suppes, T et al., "Clinical Outcome in a Randomized 1-Year Trial of Clozapine Versus Treatment as Usual for Patients With Treatment-Resistant Illness and a History of Mania" *Journal of the American Psychiatric Association*, 1999, 156(8):1164-1169.

Suppes, T et al., "Mixed Hypomania in 908 Patients With Bipolar Disorder Evaluated Prospectively in the Stanley Foundation Bipolar Treatment Network: A Sex-Specific Phenomenon" *Archives of General Psychiatry*, 2005, 62:1089-1096.

Suppes, T et al., "Risk of recurrence following discontinuation of lithium treatment in bipolar disorder" *Archives of General Psychiatry*, 1991, 48(12):1082-1088. [abstract].

Suppes, T et al., "Texas Medication Algorithm Project, phase 3(TMAP): clinical results for patients with a history of mania" *Journal of Clinical Psychiatry*, 2003, 64(4):370-82. [abstract].

Young, RC et al., "A rating scale for mania: reliability, validity and sensitivity." *The British Journal of Psychiatry*, 1978, 133:429-435.

Riedel M et al., "Quetiapine in the treatment of schizophrenia and related disorders" *Neuropsychiatric Disease and Treatment*, 2007, 3(2):219-235.

Arango, V and Mann, JJ, "Relevance of serotonergic postmortem studies to suicidal behavior" *International Review of Psychiatry*, 1992, 4:131-140.

Baldessarini, RJ et al., "Lithium Treatment and Suicide Risk in Major Affective Disorders: Update and New Findings" *Journal of Clinical Psychiatry*, 2003, 64(5):44-52.

Bertolote, JM "Suicide in the world: an epidemiological overview 1959-2000. Chapter in Suicide: an unnecessary death" Wasserman D (ed) Martin Dunitz, London, 2001:3-10.

Bertrand, D et al., "Electrophysiology: A method to investigate the Functional Properties of Ligand-Gated Channels" *Journal of Receptor and Signal Transduction Research*, 1997, 17(1-3):227-242.

(56) References Cited

OTHER PUBLICATIONS

Entusuah, R "ETRANK: a ranking procedure for handling missing data in clinical trials: application to venlafaxine extended-release depression clinical trial" *Journal of Biopharmaceutical Statistics*, 1996, 6(4):457-475.

George, TP et al., "Nicotinic Antagonist Augmentation of Selective Serotonin Reuptake Inhibitor-Refractory Major Depressive Disorder" *Journal of Clinical Psychopharmacology*, 2008, 28(3):340-344.

Gershon, ES, "Genetics" In: Goodwin FK and Redfield KR, editors. *Manic-depressive illness*; New York: Oxford University Press; 1990, 373-401.

Hamilton, M, "The assessment of anxiety states by rating" *The British Journal of Psychiatry*, 1959; 32(1):50-55.

Mann JJ and Arango V, "Neurobiology of suicide and attempted suicide. Chapter in Suicide: an unnecessary death" Wasserman D (ed.) Martin Dunitz, London, 2001:29-34.

Montgomery, S and Asberg, M, "A new depression scale designed to be sensitive to change" *The British Journal of Psychiatry*, 1979, 134:382-9.

National Institute of Mental Health, "AIMS (Abnormal Involuntary Movement Scale)" *Psychopharmacology Bulletin*, 1985, 21(4):839-843.

Posner, K et al., "Columbia-Suicide Severity Rating Scale (C-SSRS)" New York, NY: Columbia University/New York State Psychiatric Institute; 2006. http://www.fda.gov/ohrms/dockets/ac/07/slides/2007-4306s1-01-CU-Posner_files/frame.htm.

Posner, K et al., "Columbia-Suicide Severity Rating Scale (C-SSRS)" *The Columbia Suicide History Form*, developed by John Mann, MD and Maria Oquendo, MD, Conte Center for the Neuroscience of Mental Disorders, (CCNMD), New York State Psychiatric Institute, 1051 Riverside Drive, New York, NY, 10032. (Oquendo M. A., Halberstam B. & Mann J. J., Risk factors for suicidal behavior: utility and limitations of research instruments. In M.B. First [Ed.] Standardized Evaluation in Clinical Practice, 2003, 103-130). http://cssrs.columbia.edu/docs/C-SSRS_1_14_09_Baseline.pdf.

Rettersol, N and Mehlum L, "Attempted suicide as a risk factor for suicide: treatment and follow up." Wasserman D (ed) Martin Dunitz, London, 2001, 15:125-131.

Simpson, GM and Angus, JWS, "A rating scale for extrapyramidal side effects" *ACTA Psychiatrica Scandinavica*, 1970, 45(212S):S11-S19.

Stahl, SM et al., "Effectiveness of Lurasidone for Patients with Schizophrenia Following 6 Weeks of Acute Treatment with Lurasidone, Olanzapine, or Placebo: A 6-Month, Open-Label, Extension Study" *Journal of Clinical Psychiatry*, Submitted Aug. 2, 2012, accepted Feb. 15, 2013, online ahead of print: Mar. 13, 2013; 1-9.

Suppes, T et al., "The Texas Implementation of Medication Algorithms: Update to the Algorithms for Treatment of Bipolar I Disorder" *Journal of Clinical Psychiatry*, 2005, 66(7):870-886.

Suppes, T et al., "Texas Medication Algorithm Project: Development and Feasibility Testing of a Treatment Algorithm for Patients With Bipolar Disorder" *Journal of Clinical Psychiatry*, 2001, 62(6):439-447.

Brioni JD et al., "Clozapine attenuates the discriminative stimulus properties of (−)-nicotine" *Brain Research*, 1994, 643(1-2):1-9.

Iancu I et al., "Increased Suicidal Risk Among Smoking Schizophrenia Patients" *Clinical Neuropharmacology*, 2006, 29(4):230-237.

Bai O et al.,"Expression of Brain-Derived Neurotrophic Factor mRNA in Rat Hippocampus After Treatment With Antipsychotic Drugs" Journal of Neuroscience Research, 2003, 71(1):127-131.

Fukumoto T et al., "Chronic lithium treatment increases the expression of brain-derived neurotrophic factor in the rat brain" *Psychopharmacology* (Berl), 2001, 158(1):100-106.

Meltzer HY et al., "Clozapine Treatment for Suicidality in Schizophrenia: International Suicide Prevention Trial (InterSePT)" *Archives of General Psychiatry*, 2003, 60(1):82-91.

Müller-Oerlinghausen B et al., "The Impact of Lithium Long-Term Medication on Suicidal Behavior and Mortality of Bipolar Patients" *Archives of Suicide Research*, 2005, 9(3):307-319.

Stone M et al., "Risk of suicidality in clinical trials of antidepressants in adults: analysis of proprietary data submitted to US Food and Drug Administration" *BMJ*, 2009, 339:b2880.

Olesen JB et al., "Antiepileptic drugs and risk of suicide: a nationwide study" *Pharmacoepidemiology and Drug Safety*, 2010, 19:518-524.

Philip NS et al., "Nicotinic acetylcholine receptors and depression: a review of the preclinical and clinical literature" *Psychopharmacology*, Sep. 2010, Epub Jul. 8, 2010, 212(1):1-12.

Rabenstein RL et al., "The nicotinic antagonist mecamylamine has antidepressant-like effects in wild-type but not $\beta2$- or $\alpha7$-nicotinic acetylcholine receptor subunit knockout mice" *Psychopharmacology*, Dec. 2006, Epub Oct. 3, 2006, 189:395-401.

Löscher W et al., "Are neuronal nicotinic receptors a target for antiepileptic drug development? Studies in different seizure models in mice and rats" *European Journal of Pharmacology*, 2003, 466:99-111.

Chaney LA et al., "Anticonvuslant-Resistant Seizures following Pyridostigmine Bromide (PB) and N,N-Diethyl-m-toluamide (DEET)" *Toxicological Sciences*, 1999, 49:306-311.

Oquendo MA et al., "Suicidal behavior in bipolar mood disorder: clinical characteristics of attempters and nonattempters" *Journal of Affective Disorders*, 2000, 59:107-117.

Galfalvy H et al., "Clinical predictors of suicidal acts after major depression in bipolar disorder: a prospective study" *Bipolar Disorders*, 2006, 8:586-595.

Marangell LB et al., "Prospective predictors of suicide and suicide attempts in 1,556 patients with bipolar disorders followed for up to 2 years" *Bipolar Disorders*, 2006, 8:566-575.

Breslau N et al., "Smoking and the risk of suicidal behavior—A prospective study of a community sample" *Archives of General Psychiatry*, 2005, 62(3):328-334.

Brioni JD et al., "Clozapine attenuates the discriminative stimulus properties of (−)-nicotine" *Brain Research*, 1994, 643(1-2):1-9. [Abstract only].

Dwivedi Y et al., "Altered gene expression of brain-derived neurotrophic factor and receptor tyrosine kinase B in postmortem brain of suicide subjects" *Archives of General Psychiatry*, (2003), 60(8):804-815.

Fernandes CC et al., "Postsynaptic action of brain-derived neurotrophic factor attenuates alpha 7 nicotinic acetylcholine receptor-mediated responses in hippocampal Interneurons" *Journal of Neuroscience*, (2008), 28(21):5611-5618.

Grinevich VP et al., "Atypical antipsychotics as noncompetitive inhibitors of alpha4beta2 and alpha7 neuronal nicotinic receptors" 2009, *Neuropharmacology*, 57(2):183-191.

Iancu I et al., "Increased suicidal risk among smoking schizophrenia patients" *Clinical Neuropharmacology*, (2006), 29(4):230-237. [Abstract only].

Karege F et al., "Neurotrophin levels in postmortem brains of suicide victims and the effects of antemortem diagnosis and psychotropic drugs" *Molecular Brain Research*, 2005, 136(1-2):29-37.

Moore TJ et al., "Suicidal Behavior and Depression in Smoking Cessation Treatments" *PLoS One*, (2011), 6(11):E27016, pp. 1-7.

Wang H et al., "Modulation of phosphatidylinositol turnover on central nicotinic receptors" *ACTA Pharmacologica Siruca*, 1997, 18(4):341-344.

Clinical Trials Identifier NCT00319319, Last Updated Apr. 18, 2007, entitled "Nicotinic Receptor Augmentation of SSRI Antidepressants".

Clinical Trials Identifier NCT00563797, Update Jun. 11, 2009, entitled "Mecamylamine for the Treatment of Patients with Depression and Alcohol Dependence".

Hughes, JR "Smoking and Suicide: A Brief Overview" *Drug Alcohol Depend.*, Dec. 2008, 98(3):169-178.

Jamali, B et al. "Synthesis of a quaternary bis derivative of imipramine as a novel compound with potential anti-enuretic effect" *J. Pharmacy & Pharmacology*, 2009, 61:1229-1232.

Kim, B et al. "Brain-Derived Neurotrophic Factor Val/Met Polymorphism and Bipolar Disorder" *Neuropsychobiology*, 2008, 58:97-103.

(56) References Cited

OTHER PUBLICATIONS

Larsen, M et al. "Temporal expression of brain-derived neurotrophic factor (BDNF) mRNA in the rat hippocampus after treatment with selective and mixed monoaminergic antidepressants" *Eur. J. Pharmacol.*, 2008, 578:114-122.

Molteni, R. et al. "Chronic treatment with fluoxetine up-regulates cellular BDNF mRNA expression in rat dopaminergic regions" *Int'l J. Neuropsychopharmacology*, 2006, 9:307-317.

Montag, C et al. "The BDNF Val66Met polymorphism and smoking" *Neuroscience Letters*, 2008, 442:30-33.

Park, D. et al. "Mecamylamine attenuates dexamethasone-induced anxiety-like behavior in association with brain derived neurotrophic factor upregulation in rat brains" *Neuropharmacology*, 2011, 61:276-282.

Russo-Neustadt, A et al. "Hippocampal Brain-Derived Neurotrophic Factor Expression Following Treatment with Reboxetine, Citalopram, and Physical Exercise" *Neuropsychopharmacology*, 2004, 29:2189-2199.

Witte, T et al. "Do major depressive disorder and dysthymic disorder confer differential risk for suicide?" *J. Affective Disorders*, 2009, 115:69-78.

Zyprexa Relprevv prescribing information (26 pages), revised Dec. 2014.

Tegretol and Tegretol-XR prescribing information (26 pages), Sep. 2014/Jan. 2014.

Seroquel XR prescribing information (19 pages), revised Oct. 2013.

Latuda prescribing information (16 pages), revised Jul. 2013.

Lamictal prescribing information (64 pages), revised Dec. 2014.

Depakote prescribing information (51 pages), revised Mar. 2015.

Abilify prescribing information (24 pages), revised Dec. 2014.

\* cited by examiner

SHEEHAN-SUICIDALITY TRACKING SCALE (S-STS)

INSTRUCTIONS: PLEASE USE DATA FROM ALL SOURCES AND CONSIDER SEVERITY, FREQUENCY AND TIME FRAME IN YOUR RESPONSES.
THE RESPONSE "NOT AT ALL" TO ANY QUESTION MEANS "NONE" AND MEANS THAT THE THOUGHT OR BEHAVIOR "DID NOT OCCUR AT ALL".

1. Over the past (timeframe), did you have any accident?    NO ☐    YES ☐
   (this includes taking too much of your medication accidentally).

IF YES: How many times were you in an accident without intending to harm yourself or to die? ____

IF NO, SKIP TO QUESTION 2. IF YES, GO TO QUESTION 1a:

|   | Not at all | A little | Moderately | Very | Extremely |
|---|---|---|---|---|---|
| 1a. How seriously did you plan or intend to hurt yourself in any accident (either passively or actively)? | 0 | 1 | 2 | 3 | 4 |

IF THE ANSWER TO QUESTION 1a IS 0 (= Not at all), SKIP TO QUESTION 2.
IF IT IS SCORED ≥1, GO TO QUESTION 1b:

1b. Did you intend to die as a result of any accident?    NO ☐    YES ☐

Over the past (timeframe), how seriously did you:

|   | Not at all | A little | Moderately | Very | Extremely |
|---|---|---|---|---|---|
| 2. think that you would be better off dead or wish you were dead? | 0 | 1 | 2 | 3 | 4 |

How many times? ____

| 3. think about harming yourself or hurting or injuring yourself, with at least some intent or awareness that you might die as a result or think about suicide (killing yourself)? | 0 | 1 | 2 | 3 | 4 |
|---|---|---|---|---|---|

How many times? ____

| 4. have a suicide method or plan in mind (e.g. how, when or where)? | 0 | 1 | 2 | 3 | 4 |
|---|---|---|---|---|---|
| 5. Intend to follow through on a suicide plan? | 0 | 1 | 2 | 3 | 4 |
| 6. intend to die as a result of a suicidal act? | 0 | 1 | 2 | 3 | 4 |
| 7. take active steps to prepare for a suicide attempt in which you expected or intended to die? | 0 | 1 | 2 | 3 | 4 |
| 8. injure yourself on purpose without intending to kill yourself? | 0 | 1 | 2 | 3 | 4 |

How many times? ____

| 9. attempt suicide *? | 0 | 1 | 2 | 3 | 4 |
|---|---|---|---|---|---|

* "A suicide attempt is a potentially self-injurious behavior, with at least some intent (> 0) to die as a result or if intent can be inferred, e.g. if it is clearly not an accident or the individual thinks the act could be lethal, even though denying intent".
**
Note: Item 4 on S-STS ("plan for suicide") is construed as not going beyond ideas or verbalizations of a plan for suicide. If actual behaviors occur (i.e., buying a gun or taking other steps), the event should be coded as "preparatory behavior" (item 7 on S-STS). However, both events can occur separately in the same week. Aborted or interrupted attempts should NOT be coded positive on question 9, but should be coded positive on S-STS question 7. (** C-CASA definition). Posner K et al. Am J Psychiatry 164:7, July 2007.

Copyright Sheehan DV 2005-2010. All rights reserved.

FIG. 1A

SHEEHAN-SUICIDALITY TRACKING SCALE (S-STS) - EVENTS REPORT

10. IF ANSWER 9 IS POSITIVE ASK:

Over the past (timeframe), how many times did you attempt suicide? _____

| | When? dd/MMM/yyyy | How? | Not at all | A little | Moderately | Very | Extremely |
|---|---|---|---|---|---|---|---|
| | | | | | How serious was each attempt? | | |
| 1. | | | 0 | 1 | 2 | 3 | 4 |
| 2. | | | 0 | 1 | 2 | 3 | 4 |
| 3. | | | 0 | 1 | 2 | 3 | 4 |
| 4. | | | 0 | 1 | 2 | 3 | 4 |
| 5. | | | 0 | 1 | 2 | 3 | 4 |

Add rows as needed.

11. IF ANSWER 7 IS POSITIVE ASK:

Over the past (timeframe), how many distinct times did you take active steps to <u>prepare</u> for a suicide attempt in which you expected or intended to die? _____
Only count preparation events separated in time from an actual suicide attempt.

| | When? dd/MMM/yyyy | How? | Not at all | A little | Moderately | Very | Extremely |
|---|---|---|---|---|---|---|---|
| | | | | | How serious was each attempt? | | |
| 1. | | | 0 | 1 | 2 | 3 | 4 |
| 2. | | | 0 | 1 | 2 | 3 | 4 |
| 3. | | | 0 | 1 | 2 | 3 | 4 |
| 4. | | | 0 | 1 | 2 | 3 | 4 |
| 5. | | | 0 | 1 | 2 | 3 | 4 |

Add rows as needed.

SUICIDAL IDEATION EVENTS:
SUM THE "NUMBER OF TIMES" RECORDED FOR QUESTIONS 2 AND 3 TO GET THE TOTAL NUMBER OF SUICIDAL IDEATION EVENTS _____

Copyright Sheehan DV 2005-2010. All rights reserved.

FIG. 1B

SHEEHAN-SUICIDALITY TRACKING SCALE (S-STS) - CLINICIAN USE ONLY

FOR CLINICIAN USE ONLY

|   | NO | YES |
|---|----|-----|
| 12. Fatal, completed suicide? | 0 | 40 |
| 13. Fatal, but not enough information to code as a completed suicide? | 0 | 40 |

Total Scale Score     (Questions 1 - 9 + 12 + 13)     TOTAL [ ]

☐   I have reviewed the above data with the patient.

_____     _____
Clinician Signature                                    dd/MMM/yyyy Copyright Sheehan DV 2005-2010. All rights reserved.

FIG. 1C

| C-CASA Code Number | C-CASA Category | Most serious code endorsed for this time interval | # of events | How S-STS questions map to each C-CASA category |
|---|---|---|---|---|
| 1 | Completed suicide | No | 0 | A yes response to 12 |
| 2 | Suicide attempt (Potentially self-injurious behavior associated with some intent to die. Intent can be stated or inferred by rater.) | No | 0 | Any positive response to 9 or A "Yes" response to 1b |
| 3 | Preparatory acts toward imminent suicide behavior (Person takes steps to injure self but is stopped by self or other. Intent to die is either stated or inferred.). | Yes | 3 | Any positive response to 7 with a negative response to 9 |
| 4 | Suicidal ideation (Passive thoughts about wanting to be dead or active thoughts about killing oneself, not accompanied by preparatory behavior.) | No | 7 | Any positive response to 2, 3, 4, 5, or 6 with a negative response to 7 and a negative response to 9 |
| 5 | Self-injurious behavior, intent unknown (Self-injurious behavior where associated intent to die is unknown and cannot be inferred.) | No | 1 | A positive response to 1a with 1b and 5, 6 and 9 unanswered or A positive response to 7 with 1b and 5, 6 and 9 unanswered |
| 6 | Not enough information (fatal) | No | 1 | A yes response to 13 |
| 7 | Self-injurious behavior, no suicide intent | No | 0 | A positive response to 8 with negative responses to 1b and 5, 6 and 9 or A positive response to 1a and negative responses to 1b and 5, 6 and 9 |
| 8 | Other (accidental, psychiatric, medical), no deliberate self-harm | No | 2 | A positive or blank response to 1 with negative responses to 1a and 1b. and A negative response to questions 2, 3, 4, 5, 6, 7, 8, 9, 12, and 13. |
| 9 | Not enough information (non fatal) | No | 0 | Code C-CASA # 9 if there is missing or incomplete information on S-STS beyond the explicit S-STS rules above to allow mapping to codes 1-8 in C-CASA. Use information from all sources in coding. |

FIG. 2

Note: Item 4 on S-STS ("plan for suicide") is construed as not going beyond ideas or verbalizations of a plan for suicide. If actual preparatory behaviors occur (i.e., buying a gun or taking other steps – see item 7 on S-STS), the event should be regarded as "preparatory behavior" and coded as C-CASA Code Number 3. If information from the S-STS is coded as an adverse event in a research study, classify the adverse event by the C-CASA category number and category name when naming the adverse event. A "negative response" means a score of zero on that question, while a "positive response" means a score of ≥ 1 on that question.

SHEEHAN-SUICIDALITY TRACKING SCALE (S-STS)

INSTRUCTIONS: PLEASE USE DATA FROM ALL SOURCES AND CONSIDER SEVERITY, FREQUENCY AND TIME FRAME IN YOUR RESPONSES. THE RESPONSE "NOT AT ALL" TO ANY QUESTION MEANS "NONE" AND MEANS THAT THE THOUGHT OR BEHAVIOR "DID NOT OCCUR AT ALL".

1. Since your last visit, did you have any accident?    NO ☐    YES ☐
   (this includes taking too much of your medication accidentally).

IF NO, SKIP TO QUESTION 2. IF YES, GO TO QUESTION 1a:

|  | Not at all | A little | Moderately | Very | Extremely |
|---|---|---|---|---|---|
| 1a. How seriously did you plan or intend to hurt yourself in any accident (either passively or actively)? | 0 | 1 | 2 | 3 | 4 |

IF THE ANSWER TO QUESTION 1a IS 0 (= Not at all), SKIP TO QUESTION 2.
IF IT IS SCORED ≥1, GO TO QUESTION 1b:

1b. Did you intend to die as a result of any accident?    NO ☐    YES ☐

Since your last visit, how seriously did you:

|  | Not at all | A little | Moderately | Very | Extremely |
|---|---|---|---|---|---|
| 2. think that you would be better off dead or wish you were dead? | 0 | 1 | 2 | 3 | 4 |
| How many times? ____ | | | | | |
| 3. think about harming yourself or hurting or injuring yourself, with at least some intent or awareness that you might die as a result or think about suicide (killing yourself)? | 0 | 1 | 2 | 3 | 4 |
| How many times? ____ | | | | | |
| 4. have a suicide method in mind (e.g. how)? | 0 | 1 | 2 | 3 | 4 |
| 5. have a suicide plan in mind (e.g. when or where)? | 0 | 1 | 2 | 3 | 4 |
| 6. intend to act on thoughts of killing yourself? | 0 | 1 | 2 | 3 | 4 |
| 7. intend to die as a result of a suicidal act? | 0 | 1 | 2 | 3 | 4 |
| 8. take active steps to prepare for a suicide attempt in which you expected or intended to die? This includes times when you were going to kill yourself, but were interrupted or stopped yourself, before doing anything harmful. | 0 | 1 | 2 | 3 | 4 |
| 9. injure yourself on purpose without intending to kill yourself? | 0 | 1 | 2 | 3 | 4 |
| How many times? ____ | | | | | |
| 10. attempt suicide *? | 0 | 1 | 2 | 3 | 4 |

\* "A suicide attempt is a potentially self-injurious behavior, with at least some intent (> 0) to die as a result or if intent can be inferred, e.g. if it is clearly not an accident or the individual thinks the act could be lethal, even though denying intent".

\*\*
Note: Item 5 on S-STS ("plan for suicide") is construed as not going beyond ideas or verbalizations of a plan for suicide. If actual behaviors occur (i.e., buying a gun or taking other steps), the event should be coded as "preparatory behavior" (item 8 on S-STS). However, both events can occur separately in the same week. Aborted or interrupted attempts should NOT be coded positive on question 10, but should be coded positive on S-STS question 8. (\*\* C-CASA definition). Posner K et al. Am J Psychiatry 164:7, July 2007.

Copyright Sheehan DV 2005-2010. All rights reserved.

FIG. 3A

SHEEHAN-SUICIDALITY TRACKING SCALE (S-STS) - EVENTS REPORT

11. IF ANSWER 10 IS POSITIVE ASK:

Since your last visit, how many times did you attempt suicide? _____

| | When? dd/MMM/yyyy | How? | Not at all | A little | How serious was each attempt? Moderately | Very | Extremely |
|---|---|---|---|---|---|---|---|
| 1. | | | 0 | 1 | 2 | 3 | 4 |
| 2. | | | 0 | 1 | 2 | 3 | 4 |
| 3. | | | 0 | 1 | 2 | 3 | 4 |
| 4. | | | 0 | 1 | 2 | 3 | 4 |
| 5. | | | 0 | 1 | 2 | 3 | 4 |

Add rows as needed.

12. IF ANSWER 8 IS POSITIVE ASK:

Since your last visit, how many times did you take active steps to <u>prepare</u> for a suicide attempt in which you expected or intended to die? _____
    (Do not count the times connected to an actual suicide attempt.)

| | When? dd/MMM/yyyy | How? | Not at all | A little | How serious was each preparation? Moderately | Very | Extremely | Level |
|---|---|---|---|---|---|---|---|---|
| 1. | | | 0 | 1 | 2 | 3 | 4 | |
| 2. | | | 0 | 1 | 2 | 3 | 4 | |
| 3. | | | 0 | 1 | 2 | 3 | 4 | |
| 4. | | | 0 | 1 | 2 | 3 | 4 | |
| 5. | | | 0 | 1 | 2 | 3 | 4 | |

Add rows as needed.

Levels of Preparation
Level 1: You took active steps to prepare to kill yourself, but you did not start the suicide attempt itself.
Level 2: You started a suicide attempt, but then you stopped yourself before harming yourself (aborted attempt).
Level 3: You started a suicide attempt, but then someone or something stopped you before harming yourself (interrupted attempt).

SUICIDAL IDEATION EVENTS:
    SUM THE "NUMBER OF TIMES" RECORDED FOR QUESTIONS 2 AND 3 TO GET THE
    TOTAL NUMBER OF SUICIDAL IDEATION EVENTS _____

Copyright Sheehan DV 2005-2010. All rights reserved.

FIG. 3B

SHEEHAN-SUICIDALITY TRACKING SCALE (S-STS) - CLINICIAN USE ONLY

FOR CLINICIAN USE ONLY

|  | NO | YES |
|---|---|---|
| 13. Fatal, completed suicide? | 0 | 40 |
| 14. Fatal, but not enough information to code as a completed suicide? | 0 | 40 |

Total Scale Score      (Add Questions 1a + 2 through 10 + 13 + 14)      TOTAL ☐

☐  I have reviewed the above data with the patient.

_____          _____
Clinician Signature                                            dd/MMM/yyyy Copyright Sheehan DV 2005-2010. All rights reserved.

FIG. 3C

| C-CASA Code Number | C-CASA Category | Did event code occur during this coding interval? | # of times event occurred | How S-STS questions map to each C-CASA category |
|---|---|---|---|---|
| 1 | Completed suicide | No | 0 | A yes response to 13 |
| 2 | Suicide attempt (Potentially self-injurious behavior associated with some intent to die. Intent can be stated or inferred by rater.) | No | 0 | Any positive response to 10 or A "Yes" response to 1b |
| 3 | Preparatory acts toward imminent suicide behavior (Person takes steps to injure self but is stopped by self or other. Intent to die is either stated or inferred.). | Yes | 3 | Any positive response to 8 with a negative response to 10 |
| 4 | Suicidal ideation (Passive thoughts about wanting to be dead or active thoughts about killing oneself, not accompanied by preparatory behavior.) | Yes | 7 | Any positive response to 2, 3, 4, 5, 6 or 7 with a negative response to 8 and a negative response to 10 |
| 5 | Self-injurious behavior, intent unknown (Self-injurious behavior where associated intent to die is unknown and cannot be inferred.) | No | | A positive response to 1a with 1b and 6 and 7 and 10 unanswered or A positive response to 8 with 1b and 6 and 7 and 10 unanswered |
| 6 | Not enough information (fatal) | No | | A yes response to 14 |
| 7 | Self-injurious behavior, no suicide intent | No | 0 | A positive response to 9 with negative responses to 1b and 6 and 7 and 10 or A positive response to 1a and negative responses to 1b and 6 and 7 and 10 |
| 8 | Other (accidental, psychiatric, medical), no deliberate self-harm | No | | A positive or blank response to 1 with negative responses to 1a and 1b. and A negative response to questions 2, 3, 4, 5, 6, 7, 8, 9, 10, 13 and 14. |
| 9 | Not enough information (non fatal) | No | | Code C-CASA # 9 if there is missing or incomplete information on S-STS beyond the explicit S-STS rules above to allow mapping to codes 1-8 in C-CASA. Use information from all sources in coding. |

Note: Item 5 on S-STS ("plan for suicide") is construed as not going beyond ideas or verbalizations of a plan for suicide. If actual preparatory behaviors occur (i.e., buying a gun or taking other steps – see item 8 on S-STS), the event should be regarded as "preparatory behavior" and coded as C-CASA Code Number 3.
If information from the S-STS is coded as an adverse event in a research study, classify the adverse event by the C-CASA category number and category name when naming the adverse event. A "negative response" means a score of zero on that question, while a "positive response" means a score of ≥1 on that question.

FIG. 4

TREATMENT OF SUICIDAL IDEATION OR BEHAVIOR USING INHIBITORS OF NICOTINIC ACETYLCHOLINE RECEPTORS

CROSS-REFERENCE TO RELATED APPLICATION

The present application claims the benefit of U.S. Application Ser. No. 61/252,343, filed Oct. 16, 2009, which is hereby incorporated by reference herein in its entirety, including any figures, tables, nucleic acid sequences, amino acid sequences, and drawings.

BACKGROUND OF THE INVENTION

There are good reasons for investigating a medication as an anti-suicide treatment and studying suicidality as a primary indication. First, although suicide and suicidality are major and growing public health problems and suicide is now ranked as the 11th leading cause of death in the United States, the relationship between psychiatric medication and suicidality has not been well studied. Indeed, most of the work on medication and suicidality has been retrospective, confined to secondary post hoc analyses of single items on depression rating scales in registration trials pursuing other indications.

Second, although there is good evidence from clinical, epidemiologic and family populations that patients with mood disorders, including bipolar disorder I, II and NOS, have an elevated risk of suicide (1-2), there is growing evidence that vulnerability to suicidality may be inherited independently of vulnerability to mood disorders (3-8). These considerations have led to increasing calls for a separate category for "Suicide Disorders" in the Diagnostic and Statistical Manual of Mental Disorders V (DSM V).

Third, there is growing evidence that treatments that are effective for mood disorders are not always effective for suicidality and vice versa. Paradoxically, antidepressants, although they improve depression over 4 to 8 weeks, are not believed to lower suicidality. These findings highlight the need to find medications that work well for both symptomatic relief and suicidality.

Fourth, there is increasing evidence that suicidal risks vary across psychiatric medications. Today, all antidepressants, anticonvulsants and antipsychotics carry black box warnings in their product labeling, and all caution about the increased risk of suicidality on these medications compared to placebo. Preliminary evidence, however, suggests that all antipsychotics do not necessarily share the same suicidality risks and that some antipsychotics may actually lower the risk of suicidality in some disorders.

To date, no medication has been specifically approved by the U.S. Food and Drug Administration (FDA), or by other drug regulatory agencies, as an effective and safe treatment for suicidality, suicidal ideation or suicidal behaviors. Clozapine has been approved ("is indicated") "for reducing the risk of recurrent suicidal behavior in patients with schizophrenia or schizoaffective disorder who are judged to be at chronic risk for re-experiencing suicidal behavior, based on history and recent clinical state" (wording from Prescribing Information on Clozaril). However, in the context of growing concern about suicide in the United States, the FDA has recently expressed interest in reviewing any medication that might demonstrate efficacy against suicidality if suicidality is the a-priori primary outcome measure.

More than 32,000 people kill themselves each year. The increasing rates of completed and attempted suicide among veterans and active duty military is the subject of much media attention. In March 2009, the media reported that among U.S. troops, death by suicide outnumbered death in combat for two months in a row.

The World Health Organization estimates that in the year 2020 approximately 1.53 million will die from suicide. Ten to 20 times more people attempt suicide than complete suicide. This is an average of one suicide death every 20 seconds and one suicide attempt every 1 to 2 seconds (12).

Since 1950, when global suicide statistics were first collected, deaths from suicide have increased 49% in males and 33% in females. There has been a consistent but escalating three fold higher rate of successful suicides in males over females over time, ranging from 3.2:1 in 1960; 3.6:1 in 1995 to 3.9: in 2020 (12). This finding may be confounded by a larger number of countries reporting suicide statistics today than in 1950 (12). Attempted suicide is more common in females than in males. The female-male ratio for suicide attempts varies from 1.5:1 to 3:1 (13).

Approximately 10% of those admitted to hospitals following a suicide attempt eventually commit suicide. An additional 10% to 50% repeat their suicide attempts (13). After a suicide attempt, the danger of completed suicide is greatest in the first year and especially in the first 3 months after a suicide attempt (13). 90% of those who attempt suicide survive (13). Suicide attempts provide opportunities to identify and treat problems that would otherwise not come for treatment (13).

Suicide rates increase with age. In absolute numbers, most completed suicides in both men and women are between the ages of 35-45 years. The average global suicide rate for men is 24.7/100,0000 with a low of 0.9 per 100,000 for age group 5-14 years and increasing up to 66.9/100,000 in those over 75 years (12). The same increase with age is seen in females with an average rate of 6.9/100,000. This rate increases from 0.5/100,000 for the age group 5-14 years up to 29.7/100,000 in those over 75 years (12). There could be a significant increase in completed suicides in the next 15 years with the population bubble of baby boomers approaching the age of highest suicide risk. The highest suicide rates are in Eastern Europe (12).

The attempted suicide rate is higher in younger age groups than in older age groups. Conservative estimates suggest that attempted suicide is at least 10 times more common than completed suicide. The suicide attempt rate for males varies from 45-314 per 100,000 to 69-462 per 100,000 among females (13).

The largest twin study found a "concordance rate of serious suicide attempts in monozygotic twins of 23.1%" (4). This was more than a 70 fold greater risk than the risk in the total sample (4). The concordance rate for attempted suicide was higher than for completed suicide, suggesting that both attempted and completed suicide may he heritable. Adoptee studies found that the risk of suicides was transmitted from the biological family to the adoptee at birth, independent of the transmission of mood or psychotic disorders. Family studies suggest that the transmission of suicidal behavior is independent of the transmission of psychiatric disorders associated with suicidal behaviors (4, 6-8). The evidence suggests that the familial transmission of psychiatric disorders is independent of the familial transmission of genetic factors related to suicidal behavior (4, 6-8, 13).

Low levels of 5-Hydroxyindoleacetic acid (5-HIAA) in the cerebral spinal fluid (CSF) predict future suicide and suicide attempts. "Low levels of 5-HIAA in the CSF appears to be a biological index of vulnerability to suicidal behavior in several psychiatric disorders" (4). "The more lethal the suicidal behavior, the lower the level of 5-HIAA in the CSF" (4). Tryptophan hydroxylase is the enzyme "involved in the rate-limiting step in the synthesis of serotonin" (4). "Several studies found an association between a polymorphism in the tryptophan hydroxylase gene in intron 7 and suicidal behavior" (4). Those who make suicide attempts are different from those with the same psychiatric disorder but do not make suicide attempts by having more of the U-allele variant of this gene. This U-allele variant "is associated with lower levels of 5-HIAA in the CSF and a blunted prolactin response to funfluramine" (4).

The standard treatment approach for treating suicidal patients with recurrent unipolar major depressive disorder, bipolar depression and posttraumatic stress disorder, involves a combination of antidepressant medications, mood stabilizers and psychosocial treatments including cognitive behavior therapy.

Traditionally, it was assumed that the presence of suicidal ideation was driven by a depressive disorder and that when a depressive disorder was treated the suicidality would clear. Recent genetic studies suggest that, although suicidality and mood disorders frequently co-occur, there may be a different genetic vulnerability to each. All antidepressants now have "black box warnings" in their labeling indicating that there may be an increase in suicidal behaviors among some patients on antidepressants and that this needs to be monitored. Antidepressants are less effective against suicidality than was previously assumed (14). In bipolar depression, there is no evidence antidepressants are helpful (Sachs G. S. and Nierenberg A. N. et al. Effectiveness of Adjunctive Antidepressant Treatment for Bipolar Disorder. *New England Journal of Medicine April* 2007. Number 17; 356:1711-1722).

In many bipolar patients, antidepressants increase rapid cycling and sudden mood switching, and increase the risk of suicidality. Lithium is the only medication that consistently reduces suicidality in recurrent unipolar major depressive disorder and in bipolar disorder (15). Balldesarini (16) found a 13 fold lower incidence of attempted and completed suicide in those on long-term lithium treatment compared to those who did not receive lithium. Balldesarini (17) found that the fatality rate due to suicide after discontinuing lithium was 12.6 times higher compared to the rate during lithium maintenance. These findings have not been investigated in a VA population.

In research on treatment in most specialties and disease states, the main contributors to mortality are usually the primary targets of treatment. Although suicide is the most important contributor to lethality in psychiatric disorders, it is almost never the primary target in treatment studies. This may be because of safety concerns or because of the absence, until recently, of suicidality measurements that inspire scientific confidence. A medication that lowers suicidality would represent a very welcome opportunity to lower mortality rates from suicide.

BRIEF SUMMARY OF THE INVENTION

The present invention relates to the treatment of suicidal thoughts or ideation, or suicidal behavior, as a primary indication, and the identification of interventions effective in treating suicidal ideation or behavior, and reducing suicidality.

Smoking is associated with an increased risk of suicidality (independently of major depressive disorder), potentially through nicotine's activation and upregulation of neuronal nicotinic receptors (nAChR) in the brain. Varenicline, a partial agonist of neuronal nicotinic receptors, approved in the United States for the treatment of smoking cessation, has been reported to be associated with an increase in the risk of suicidality relative to other treatments (i.e., buprorion, Zyban®). Postmortem analysis of completed suicide victims reveals depletion of brain-derived neurotrophic factor (BDNF) in the brain, independent of major depressive disorder. Current drugs most effective in reducing suicidality, such as lithium and clozapine, increase brain BDNF levels. Moreover, these drugs' efficacy in treating suicidality occurs independently of their effects on symptoms of major depressive disorder. Recent studies suggest that one of BDNF's primary functions is the indirect inhibition or down-regulation of nAChrs in the brain. Moreover, chronic administration of lithium in rodents decreases their physiological response to nicotine suggesting a lithium mediated down-regulation of nAChrs. In addition, an active metabolite of Clozapine, was found to be most effective (at therapeutic concentrations) at inhibiting nAChrs relative to other atypical neuroleptics tested.

Without being limited by theory, the present inventors have surmised that overstimulation of nAChRs, either directly (e.g., nicotine, varenicline) or indirectly (e.g., low brain-derived neurotrophic factor (BDNF) levels) increases the risk of suicidality independent of major depressive disorder, and treatment with lithium or clozapine, both of which increase brain BDNF levels and inhibit nAChRs, effectively reduce suicidality independent of major depressive disorder. Therefore, inhibition of nAChRs, by lithium, clozapine, and nAChR antagonists (such as mecamylamine and TC-5214) will be effective in the treatment of suicidality even in the absence of major depressive disorder.

One aspect of the invention concerns a method of treating suicidal ideation or suicidal behavior in a subject in need thereof, in the absence of major depressive disorder, comprising decreasing endogenous nicotinic acetylcholine receptor (nAChR) activity in the subject. Preferably, nAChR activity is decreased by administering an effective amount of an inhibitor of a nAChR to the subject that is not suffering from major depressive disorder. The nAChR inhibitor may be administered to the subject in an immediate release formulation or a controlled-release (extended release or delayed release) formulation.

One aspect of the invention concerns a method of treating suicidal ideation or suicidal behavior in a subject in need thereof, in the absence of major depressive disorder, comprising administering an effective amount of asenapine to the subject that is not suffering from major depressive disorder.

The suicidal ideation or suicidal behavior may be drug-induced or non-drug-induced (e.g., endogenous). In some embodiments, the subject has suicidal thoughts and is at risk of committing suicide. In some embodiments, the subject has tried to commit suicide or has a history of suicide attempts or other suicidal behaviors (e.g., suicide gestures).

In some embodiments, the subject is identified as suffering from suicidal ideation or behavior using a suicidality scale prior to or at the time of treatment. Preferably, the suicidality is capable of direct mapping to the Columbia Classification Algorithm for Suicide Assessment (C-CASA). In some embodiments, the suicidality scale is the Sheehan Suicidality Tracking Scale (S-STS) or Columbia Suicide Severity Rating Scale (C-CSSRS).

The C-CASA System (Columbia Classification Algorithm for Suicide Assessment) is a system now widely adopted to classify all the significant domains of interest in assessing suicidal ideation, self-harm and suicidal behaviors. The C-CASA system was developed in collaboration between the CNS division of the FDA and national experts on suicide at academic institutions and at Columbia University in the United States, in the aftermath of the detection of increased suicidality in children and adolescents on antidepressants.

However, assessing and detecting the suicidal ideation, self-harm and suicidal behaviors are separate from the classification algorithm itself. Consequently, the FDA requires that any suicidality scale or suicidality assessment instrument used in clinical research must demonstrate how the assessment instrument maps to each of the C-CASA classification categories in a reproducible, transparent manner. The Sheehan-Suicidality Tracking Scale (S-STS), shown in FIGS. 1A-1C, provides such a mapping plan to the FDA. The C-CASA mapping procedure is shown in FIG. 2. Exemplified directions and scoring instructions for the S-STS of FIGS. 1A-1C are provided in Example 1. FIGS. 3A-3C show an alternative S-STS that may be utilized, with disaggregated levels of preparation, levels of intent, and levels of method and plan, which allows for re-aggregation in any of their permutations. FIG. 4 shows a C-CASA mapping table, coinciding with the alternative S-STS of FIGS. 3A-3C.

In some embodiments, the subject has abnormally low BDNF in the brain, or an abnormally low cerebrospinal fluid (CSF) monoamine metabolite concentration, prior to decreasing nAChR activity in the subject. In some embodiments, the subject is determined to have an abnormally low BDNF or cerebrospinal fluid (CSF) monoamine metabolite concentration prior to decreasing nAChR activity in the subject. In some embodiments, the monoamine metabolite is 5-hydroxyinoleacetic acid (5-HIAA). In some embodiments, the subject has a polymorphism in the tryptophan hydroxylase gene in intron 7.

Many disorders are known to sometimes be associated with suicidality. In some embodiments, the subject is suffering from bipolar disorder, panic disorder, panic disorder, social anxiety, post-traumatic stress disorder (PTSD), substance dependence/abuse, eating disorder, obsessive compulsive disorder (OCD), schizophrenia, schizo-affective disorder, schizophrenoform disorder, Huntington's disease, early Alzheimer's disease, or Parkinson's disease.

In another aspect, the invention concerns a method of treating a subject suffering from suicidal ideation or behavior, comprising the steps of: (a) marketing to a physician a pharmaceutical or biological product that is an inhibitor of nAChR activity as being effective for the treatment of a subject suffering from suicidal ideation or behavior; (b) assessing the subject as suffering from suicidal ideation or exhibiting suicidal behavior (preferably by a physician); (c) prescribing the pharmaceutical or biological product to the subject by the physician in response to the marketing of the pharmaceutical or biological product and the assessment of the subject; and (d) administering the prescribed pharmaceutical or biological product to the subject. Preferably, step (b) further includes documenting the assessment, i.e., documenting that the subject is suffering from suicidal ideation or exhibiting suicidal behavior and, optionally, the nature of the suicidal ideation or suicidal behavior present.

In another aspect, the invention concerns a method for marketing an inhibitor of nAChR activity, comprising marketing the inhibitor as being effective for the treatment of suicidal ideation or suicidal behavior in a subject.

In another aspect, the invention concerns a method for determining the efficacy of a treatment for suicidal ideation or suicidal behavior, comprising identifying a subject as having suicidality symptoms using a suicidality scale that is capable of direct mapping to the Columbia Classification Algorithm for Suicide Assessment (C-CASA); administering a candidate treatment to the identified subject; and determining whether the candidate treatment is effective in preventing, reducing (e.g., reducing the severity or frequency of), or eliminating suicidal ideation or behavior, wherein the candidate treatment comprises inhibition of nAChR activity in the subject. In some embodiments, the method comprises identifying a subject as having suicidality symptoms of more than zero as measured by the Sheehan Suicidality Tracking Scale (S-STS); administering a candidate treatment to the identified subject, wherein the candidate treatment comprises inhibition of nAChR activity in the subject; and determining whether the candidate treatment is effective in preventing, reducing, or eliminating suicidal ideation or behavior in the identified subject.

Determination of treatment effectiveness can be ascertained by comparing the effects of the candidate treatment on the identified subject to that of an appropriate control (e.g., a placebo). Improvement on the suicidality scale is indicative of treatment efficacy. Effects of the candidate nAChR inhibition treatment that may be evaluated include, but are not limited to, physiological effects and behavioral effects (e.g., symptoms of suicidal tendency, such as suicidal ideation or suicidal behavior). The candidate treatment may be any pharmacologic or biologic intervention, such as a small molecule, polypeptide, or nucleic acid molecule (e.g., DNA or RNA) that results in nAchR inhibition. However, the candidate treatment is not limited by mechanism, other than nAChR inhibition. Thus, the candidate treatment may potentially operate to treat the suicidal ideation or suicidal behavior by one or more mechanisms in addition to that of nAChR inhibition.

The method of determining the efficacy of a treatment for suicidal ideation or behavior is unique in its assessment of the specific effects of a medication or other treatment on suicidality as a primary outcome measure, and it does so in a way that is carefully designed to ensure safety and promote scientific confidence with suicidality tracking measures. If the treatment is found to be effective against suicidality in one or more of the disorders studied (e.g., bipolar disorder, and/or major depressive disorder), the study results are likely to be of great interest.

Another aspect of the invention is an article of manufacture useful for determining the efficacy of a treatment for suicidal ideation or behavior. The article of the invention comprises computer-executable instructions embodied in a computer-readable medium for performing the method for determining efficacy of a treatment for suicidal ideation or suicidal behavior described herein.

Another aspect of the invention concerns a therapeutic package comprising (a) a container, (b) a dosage form of an inhibitor of nAChR activity, and (c) written matter associated with the therapeutic package stating that the dosage form can be administered to treat suicidal ideation or behavior in a subject. Another aspect of the invention concerns a therapeutic package for dispensing an inhibitor of nicotinic acetylcholine receptor (nAChR) activity to a subject being treated for suicidal ideation or behavior, comprising: (a) one or more unit doses, each unit dose comprising an effective amount of the inhibitor to treat suicidal ideation or behavior in a subject; and (b) a container containing (i) the unit dose or unit doses and (ii) labeling directing the use of the package, unit dose, or unit doses in the treatment of suicidal ideation or behavior in a subject.

Another aspect of the invention is a method of marketing an inhibitor of nAChR activity by marketing, advertising, or selling the inhibitor for the treatment or reduction of suicidal ideation or behavior in a subject in need thereof. The marketing may be directed to, for example, people suffering from suicidal thoughts and/or physicians treating such people. The marketing step may comprise the step of including a statement in the labeling for a pharmaceutical or biological product that is an nAChR inhibitor that the product can treat or reduce suicidal ideation or behavior in a person.

BRIEF DESCRIPTION OF THE DRAWINGS

FIGS. 1A-1C show the S-STS, including questions 1-9 (FIG. 1A), questions 10-11 (FIG. 1B), and a section for clinician use (FIG. 1C).

FIG. 2 shows a C-CASA mapping table, including exemplified events and how S-STS questions map to each C-CASA category and associated code number.

FIGS. 3A-3C show an alternative S-STS, with disaggregated levels of preparation, levels of intent, and levels of method and plan, which allows for re-aggregation in any of their permutations.

FIG. 4 shows a C-CASA mapping table, coinciding with the alternative S-STS of FIGS. 3A-3C.

DETAILED DISCLOSURE OF THE INVENTION

One aspect of the invention concerns a method of treating suicidal ideation or suicidal behavior in a subject in need thereof, in the absence of major depressive disorder, comprising decreasing endogenous nicotinic acetylcholine receptor (nAChR) activity in the subject. Preferably, nAChR activity is decreased by administering an effective amount of an inhibitor of a nAChR to the subject that is not suffering from major depressive disorder. The nAChR inhibitor may be administered to the subject in an immediate release formulation or a controlled-release (extended release or delayed release) formulation.

Examples of nAChR inhibitors include small molecule antagonists of nAChR receptors, such as those disclosed in Shytle R. D. et al., *Molecular Psychiatry*, 2002, 7:525-535, which is incorporated herein by reference in its entirety. In some embodiments, the nAChR inhibitor is a lithium compound or a quetiapine compound. In some embodiments, the nAChR inhibitor is selected from the group consisting of mecamylamine, TC-5214, clozapine bupropion, amitriptyline, imipramine, desipramine, nisoxetine, fluoxetine, citalopram, nomifensine, sertraline, paroxetine, nefazodone, venlafaxine, GBR-12909, and methylcaconitine. In some embodiments, the nAChR inhibitor is a polypeptide, such as alpha-conotoxin or alpha-bungarotoxin. In some embodiments, the nAChR antagonists are mixed agonists-antagonists (also having some agonist effects on nAChR receptors). Preferably, the nAChR receptor antagonists are selective nAChR antagonists. Other nAChR antagonists include, but are not limited to, those disclosed in U.S. Pat. No. 5,981,193 (Harpold et al.); U.S. Pat. No. 5,952,339 (Bencherif et al.); U.S. Pat. No. 6,121,289 (Houdi); U.S. Pat. No. 6,503,922 (Crooks et al.); U.S. Pat. No. 6,780,871 (Glick et al.); U.S. Patent Publication No. 20060280818 (Palu et al.); U.S. Patent Publication No. 20080287490 (Crooks et al.); U.S. Patent Publication No. 20060148675 (Cooke et al.); U.S. Patent Publication No. 20020099069 (Crooks et al.); U.S. Patent Publication No. 20050026842 (Simon); Dwoskin L. P. and P. A. Crooks, *The Journal of Pharmacology and Experimental Therapeutics*, 2001, 298(2):395-402; and Dwoskin L. P. and P. A. Crooks, *Annals of the New York Academy of Sciences*, 2006, 868:617-619.

Preferably, the inhibitor of nAChR activity is a molecule(s) that reduces activity of nicotinic receptors containing either alpha4 and beta2 subunits, or alpha7-nAChR subunits. In some embodiments, the nAChR(s) inhibited by the inhibitor are neuronal nAChRs (e.g., brain nicotinic receptors such as alpha7-containing receptors, alpha4(2)beta2(3), or alpha4(3) beta2(2)). In some embodiments, the nAChR(s) inhibited by the inhibitor have at least one type of alpha and one type of beta subunit. In some embodiments, the nAChR(s) inhibited by the inhibitor is a presynaptic nAChR(s).

nAChR inhibitors that may be used in the methods and products of the invention are not limited to small molecule antagonists of nAChR activity. For example, inhibitors that inhibit nAChR activity within a subject at the genetic level (e.g., the DNA or RNA level), reducing expression of an nAChR gene, may be utilized. In some embodiments, the gene-based inhibitor is an interfering RNA molecule (e.g., siRNA or shRNA), an antisense oligonucleotide, or ribozyme that targets a nAChR gene or transcript in the subject.

In one embodiment, the inhibitor is an interfering RNA specific for a target mRNA sequence of an nAChR. RNAi molecules can be selected using an siRNA Target Finder program (AMBION) and in accordance with published guidelines (Tuschl T., *Nature Biotechnol.*, 2002, 20:446448). As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to reduce (e.g., to lessen (knockdown) or essentially eliminate ("silence")) the expression of target genes.

As used herein, the term "small interfering RNA" ("siRNA") (also referred to in the art as "short interfering RNAs") refers to an RNA (or RNA analog) that has a sequence sufficiently complementary to a target mRNA sequence to direct or mediate target-specific RNA interference (RNAi). In some embodiments, the siRNA is between about 10-50 nucleotides (or nucleotide analogs). In some embodiments, the siRNA is between about 17-30 nucleotides (or nucleotide analogs). Optionally, a polynucleotide (e.g., DNA) encoding the siRNA may be administered to cells in vitro or in vivo, such as in a vector, wherein the DNA is transcribed.

As used herein, a siRNA having a "sequence sufficiently complementary to a target mRNA sequence to direct target-specific RNA interference (RNAi)" means that the siRNA has a sequence sufficient to trigger the destruction of the target mRNA of the nAChR by the RNAi machinery or process. "mRNA" or "messenger RNA" or "transcript" includes single-stranded RNA that specifies the amino acid sequence of one or more polypeptides. This information is translated during protein synthesis when ribosomes bind to the mRNA.

Furthermore, in accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, the gene-based nAChR inhibitor (such as an RNAi molecule, antisense oligonucleotide, or ribozyme) may be targeted wholly or in part to these associated ribonucleotides as well as to the informational ribonucleotides. In preferred embodiments, the inhibitor is complementary or specifically hybridizable with a transcription initiation site, a translation initiation site, a 5' cap region, an intron/exon junction, coding sequences or sequences in the 5'- or 3'-untranslated region.

The interfering RNA that function as nAChR inhibitors include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the nAChR mRNA, and the other strand is identical or substantially identical to the first strand. The dsRNA molecules that function as nAChR inhibitors can be chemically synthesized, or can be transcribed in vitro from a DNA template, or in vivo from, e.g., shRNA.

The scientific literature is replete with reports of endogenous and exogenous gene expression silencing using siRNA, highlighting their therapeutic potential (Gupta, S. et al. *PNAS*, 2004, 101:1927-1932; Takaku, H. *Antivir Chem. Chemother*, 2004, 15:57-65; Pardridge, W. M. *Expert Opin. Biol. Ther.*, 2004, 4:1103-1113; Zheng, B. J. *Antivir. Ther.*, 2004, 9:365-374; Shen, W. G. *Chin. Med. J. (Engl)*, 2004, 117:1084-1091; Fuchs, U. et al. *Curr. Mel. Med.*, 2004, 4:507-517; Wadhwa, R. et al. *Mutat. Res.*, 2004, 567:71-84; Ichim, T. E. et al. *Am. J. Transplant*, 2004, 4:1227-1236; Jana, S. et al. *Appl. Microbiol. Biotechnol.*, 2004, 65:649-657; Ryther, R. C. et al. *Gene Ther.*, 2005, 12:5-11; Chae, S-S. et al., *J. Clin. Invest.*, 2004, 114:1082-1089; Fougerolles, A. et al., *Methods Enzymol.*, 2005, 392:278-296), each of which is incorporated herein by reference in its entirety. Therapeutic silencing of endogenous genes by systemic administration of siRNAs has been described in the literature (Kim B. et al., *American Journal of Pathology*, 2004, 165:2177-2185; Soutschek J. et al., *Nature*, 2004, 432:173-178; Pardridge W. M., *Expert Opin. Biol. Ther.*, 2004, July, 4(7): 1103-1113), each of which is incorporated herein by reference in its entirety.

There are a number of companies that will generate interfering RNAs for a specific gene. Thermo Electron Corporation (Waltham, Mass.) has launched a custom synthesis service for synthetic short interfering RNA (siRNA). Each strand is composed of 18-20 RNA bases and two DNA bases overhang on the 3' terminus. Dhannacon, Inc. (Lafayette, Colo.) provides siRNA duplexes using the 2'-ACE RNA synthesis technology. Qiagen (Valencia, Calif.) uses TOM-chemistry to offer siRNA with high individual coupling yields (Li, B. et al., *Nat. Med.*, 2005, 11(9), 944-951).

An "antisense" nucleic acid sequence (antisense oligonucleotide) can include a nucleotide sequence that is complementary to a "sense" nucleic acid encoding a protein, e.g., complementary to the coding strand of a double-stranded cDNA molecule or complementary to the nAChR mRNA. Antisense nucleic acid sequences and delivery methods are well known in the art (Goodchild *J., Curr. Opin. Mol. Ther.*, 2004, April, 6(2):120-128; Clawson G. A. et al., *Gene Ther.*, 2004, September, 11(17):1331-1341), which are incorporated herein by reference in their entirety. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence within the nAChR mRNA. An antisense oligonucleotide can be, for example, about 7, 10, 15, 20, 25, 30, 35, 40, 45, 50, 55, 60, 65, 70, 75, 80, or more nucleotides in length.

Ribozymes are a type of RNA that can be engineered to enzymatically cleave and inactivate other RNA targets in a specific, sequence-dependent fashion. Ribozymes and methods for their delivery are well known in the art (Hendry P. et al., *BMC Chem. Biol.*, 2004, December, 4(1):1; Grassi G. et al., *Curr. Pharm. Biotechnol.*, 2004, August, 5(4):369-386; Bagheri S. et al., *Curr. Mol. Med.*, 2004, August, 4(5):489-506; Kashani-Sabet M., *Expert Opin. Biol. Ther.*, 2004, November, 4(11):1749-1755), each of which are incorporated herein by reference in its entirety. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art.

The nAChR inhibitors used in the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., *Drug Deliv. Rev.* 47(1): 99-112 (2001) (describes nucleic acids loaded to polyalkylcyanoacrylate (PACA) nanoparticles); Fattal et al., *J. Control Release* 53(1-3):137-43 (1998) (describes nucleic acids bound to nanoparticles); Schwab et al., *Ann. Oncol.* 5 Suppl. 4:55-8 (1994) (describes nucleic acids linked to intercalating agents, hydrophobic groups, polycations or PACA nanoparticles); and Godard et al., *Eur. J. Biochem.* 232(2):404-10 (1995) (describes nucleic acids linked to nanoparticles).

One aspect of the invention concerns a method of treating suicidal ideation or suicidal behavior in a subject in need thereof, in the absence of major depressive disorder, comprising administering an effective amount of asenapine to the subject that is not suffering from major depressive disorder.

The suicidal ideation or suicidal behavior may be drug-induced or non-drug-induced (e.g., endogenous. In some embodiments, the subject has suicidal thoughts and is at risk of committing suicide. In some embodiments, the subject has tried to commit suicide or has a history of suicide attempts or other suicidal behaviors (e.g., suicide gestures). In some embodiments, the subject is suffering from bipolar disorder (e.g., ambulatory bipolar disorder), schizophrenia, or both. In some embodiments, the subject is not suffering from bipolar disorder. In some embodiments, the subject has suffered a major depressive episode. In some embodiments, the subject has not suffered a major depressive episode. In some embodiments, the subject is assessed (e.g., diagnosed) as suffering from suicidal ideation or behavior by a clinician prior to decreasing nAChR activity in the subject.

In some embodiments, the subject is identified as suffering from suicidal ideation or behavior using a suicidality scale prior to or at the time of treatment. Preferably, the suicidality is capable of direct mapping to the Columbia Classification Algorithm for Suicide Assessment (C-CASA). In some embodiments, the suicidality scale is the Sheehan Suicidality Tracking Scale (S-STS) or Columbia Suicide Severity Rating Scale (C-CSSRS). In some embodiments, the subject is identified as having suicidality symptoms of more than zero as measured by the S-STS prior to decreasing nAChR activity in the subject. For example, the subject of treatment may have more than a zero total suicidality score and more than a zero suicidal ideation score prior to, or at the time of, administration of the nAChR inhibitor.

In some embodiments, the subject has abnormally low BDNF in the brain, or an abnormally low cerebrospinal fluid (CSF) monoamine metabolite concentration, prior to decreasing nAChR activity in the subject. In some embodiments, the subject is determined to have an abnormally low BDNF or cerebrospinal fluid (CSF) monoamine metabolite concentration prior to decreasing nAChR activity in the subject. In some embodiments, the monoamine metabolite is 5-hydroxyinoleacetic acid (5-HIAA). In some embodiments, the subject has a polymorphism in the tryptophan hydroxylase gene in intron 7. Assays, such as enzyme-linked immunosorbent assays, useful for qualitative and/or quantitative detection of target analytes such as BDNF and 5-HIAA in a sample obtained from the subject are known in the art and may be utilized for determination of abnormal levels in the subject (Bard Y. A., Progress in Growth Factor Research, 1990, 2:237-248; Thoenen H. et al., *Trends in Neurological Sciences*, 1991, 14:165-170; Acheson A. et al., *Nature* (London), 1995, 374(6521):450-453; Laske C. et al., *Journal of Psychiatric Research*, 2007, 41:600-605; Tramontina J. et al., *Molecular Psychiatry*, 2007, 12:230-231; Neumeister A. et al., *Am. J. Psychiatry*, 2005, 162:805-807; Zakariya K. et al., *Clin. Biochem.*, 1982, 2:106-108; Manz B. et al., *Clin. Chem. Clin. Biochem.*, 1987, 25:101-106; Delaage M. A. et al., *J. Physiol.*, 1981, 77:339-347; and Zajicek B. S. et al., *Neuropsychopharmacology*, 2000, 22:240-250).

The suicidal ideation treated by reducing nAChR activity in the subject may be active suicidal ideation or passive suicidal ideation. In some embodiments, the subject is not suffering from major depressive disorder. In some embodiments, the subject is suffering from an anxiety disorder or anxiety symptoms. In some embodiments, the subject is suffering from bipolar depression, or post-traumatic stress disorder. In some embodiments, the subject is suffering from bipolar disorder. In some embodiments, the subject is not suffering from bipolar disorder.

Many disorders are known to sometimes be associated with suicidality. In some embodiments, the subject is suffering from bipolar disorder, panic disorder, panic disorder, social anxiety, post-traumatic stress disorder (PTSD), substance dependence/abuse, eating disorder, obsessive compulsive disorder (OCD), schizophrenia, schizo-affective disorder, schizophrenoform disorder, Huntington's disease, early Alzheimer's disease, or Parkinson's disease.

To reduce nAChR activity in the subject having suicidal ideation or exhibiting suicidal behavior, an inhibitor of nAChR activity is preferably administered to the subject as a monotherapy. Preferably, no substances with psychotropic effects (such as mood stabilizing, antidepressant, antipsychotic, or anxiolytic medication), other than an inhibitor, is administered to the subject concurrently with the inhibitor, or administered less than one week prior to administration of the inhibitor. In some embodiments, the subject is administered a mood stabilizing, antidepressant, antipsychotic, or anxiolytic medication at least one week, two weeks, three weeks, or one month prior to administration of the inhibitor.

Various formulations, routes of administration, and dosing regimens that may be used to deliver the nAChR inhibitor to the subject are described in detail herein. In some embodiments of the methods, the formulation is an intravenous formulation. In some embodiments of the methods, the formulation is an oral formulation. Optionally, the formulations include one or more nAChR inhibitors together with other ingredients. The formulations may be administered in a variety of dosing regimens, including administering one or more formulations that may or may not be administered via the same route of administration. The formulations may also be delivered by repeat dosing and by substantially continuous dosing.

In some embodiments, two or more nAChR inhibitors are administered to the subject. In some embodiments, the inhibitor is administered once daily. In some embodiments, the inhibitor is administered orally or via injection (e.g., intravenously). In some embodiments, the inhibitor is administered in the form of a tablet, capsule, suspension, or solution.

In some embodiments, the nAChR inhibitors are prepared with carriers that will protect the inhibitors against rapid elimination from the body, such as a controlled-release matrix, implant, and/or microencapsulated delivery system.

In another aspect, the invention concerns a method of treating a subject suffering from suicidal ideation or behavior, comprising the steps of: (a) marketing to a physician a pharmaceutical or biological product that is an inhibitor of nAChR activity as being effective for the treatment of a subject suffering from suicidal ideation or behavior; (b) assessing a subject as suffering from suicidal ideation or exhibiting suicidal behavior (preferably by a physician); (c) prescribing the pharmaceutical or biological product to the subject by the physician in response to the marketing of the pharmaceutical or biological product and the assessment of the subject; and (d) administering the prescribed pharmaceutical or biological product to the subject. Preferably, step (b) further includes documenting the assessment, i.e., documenting that the subject is suffering from suicidal ideation or exhibiting suicidal behavior and, optionally, the nature of the suicidal ideation or suicidal behavior present.

In another aspect, the invention concerns a method for marketing an inhibitor of nAChR activity, comprising marketing the inhibitor as being effective for the treatment of suicidal ideation or suicidal behavior in a subject.

In another aspect, the invention concerns a method for determining the efficacy of a treatment for suicidal ideation or suicidal behavior, comprising identifying a subject as having suicidality symptoms using a suicidality scale that is capable of direct mapping to the Columbia Classification Algorithm for Suicide Assessment (C-CASA); administering a candidate treatment to the identified subject; and determining whether the candidate treatment is effective in preventing, reducing (e.g., reducing the severity or frequency), or eliminating suicidal ideation or behavior. In some embodiments, the method comprises identifying a subject as having suicidality symptoms of more than zero as measured by the Sheehan Suicidality Tracking Scale (S-STS); administering a candidate treatment to the identified subject; and determining whether the candidate treatment is effective in preventing, reducing, or eliminating suicidal ideation or behavior in the identified subject.

Determination of treatment effectiveness can be ascertained by comparing the effects of the candidate treatment on the identified subject to that of an appropriate control (e.g., a placebo). Improvement on the suicidality scale following treatment is indicative of treatment efficacy. No change or worsening on the suicidality scale following treatment is indicative of lack of treatment efficacy. Effects of the candidate treatment that may be evaluated include, but are not limited to, physiological effects and behavioral effects (e.g., symptoms of suicidal tendency, such as suicidal ideation or suicidal behavior). The candidate treatment may be any pharmacological intervention, such as a small molecule, polypeptide, or nucleic acid molecule (e.g., DNA or RNA). Other than nAChR inhibition, the candidate treatment is not limited by mechanism, i.e., the candidate treatment may potentially operate to treat the suicidal ideation or suicidal behavior by one or more mechanisms in addition to nAChR inhibition. The efficacy determining method may be used to test one or more candidate treatments on a population of subjects, e.g., as part of a clinical trial.

In some embodiments of the efficacy determining method, the subject is suffering from bipolar disorder, panic disorder, panic disorder, social anxiety, post-traumatic stress disorder (PTSD), substance dependence/abuse, eating disorder, obsessive compulsive disorder (OCD), schizophrenia, schizo-affective disorder, schizophrenoform disorder, Huntington's disease, early Alzheimer's disease, or Parkinson's disease.

Another aspect of the invention is an article of manufacture useful for determining the efficacy of a treatment for suicidal ideation or behavior. The article of the invention comprises computer-executable instructions embodied in a computer-readable medium for performing the method for efficacy of a treatment for suicidal ideation or suicidal behavior described herein.

Another aspect of the invention concerns a therapeutic package comprising (a) a container, (h) a dosage form of an inhibitor of nAChR activity, and (c) written matter associated with the therapeutic package stating that the dosage form can be administered to treat suicidal ideation or behavior in a subject. Another aspect of the invention concerns a therapeutic package for dispensing an inhibitor of nicotinic acetylcholine receptor (nAChR) activity to a subject being treated for suicidal ideation or behavior, comprising: (a) one or more unit doses, each unit dose comprising an effective amount of the inhibitor to treat suicidal ideation or behavior in a subject; and (b) a container containing (i) the unit dose or unit doses and (ii) labeling directing the use of the package, unit dose, or unit doses in the treatment of suicidal ideation or behavior in a subject.

Another aspect of the invention is a method of marketing an inhibitor of nAChR activity by marketing, advertising, or selling the inhibitor for the treatment or reduction of suicidal ideation or behavior in a subject in need thereof. The marketing may be directed to, for example, people suffering from suicidal thoughts and/or physicians treating such people. The marketing step may comprise the step of including a statement in the labeling for a pharmaceutical or biological product that is an nAChR inhibitor that the inhibitor can treat or reduce suicidal ideation or behavior in a person.

The pharmaceutical composition comprising asenapine or one or more inhibitors of nAChR activity may be used for the treatment of persons suffering from suicidal ideation or behavior. Some persons having suicidal thoughts suffer from diseases or disorders such as, depression, including major or severe depression, depression with anxiety symptoms in the form of either anxiety disorders as defined in DSM-IV (American Psychiatric Association: *Diagnostic and Statistical Manual of Mental Disorders*, Fourth Edition, Text Revision. Washington D.C., American Psychiatric Association, 2000, or DSM-IV, which is hereby incorporated by reference) or associated anxiety symptoms and in connection with other diseases involving depression. The individuals treated in accordance with the treatment methods of the invention do not suffer from major depressive disorder at the time of the treatment.

The pharmaceutical composition according to the invention is preferably an oral formulation, preferably a tablet. However, conventional capsule formulations are also possible. Tablets may be prepared by mixing the active ingredient or a granulate thereof with ordinary adjuvants, fillers and/or diluents and subsequently compressing the mixture in a conventional tableting machine or filling the ingredients in a capsule, for example a gelatine capsule. Examples of adjuvants, fillers or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilization of the solution and filling in suitable ampules or vials. Any suitable additive conventionally used in the art may be added, such as tonicity agents, preservatives, antioxidants, etc.

An effective amount of one or more nAChR inhibitors may be administered to a subject by a number of routes. An effective amount is an amount that, during the course of therapy, will have a preventive or ameliorative effect on suicidal ideation or suicidal behavior. For example, an effective amount is an amount that prevents the occurrence or recurrence, or reduces the frequency of suicidal behaviors such as attempted suicide or suicide gesture. Quantitatively, an effective amount may vary, e.g., depending upon the patient, the severity of the disorder or symptom being treated, and the route of administration. Such dose can be determined by routine studies.

It will be understood that the dosing protocol including the amount of nAChR inhibitor(s) actually administered can be determined by a physician in the light of the relevant circumstances including, for example, the condition to be treated, the chosen route of administration, the age, weight, and response of the individual patient, and the severity of the patient's symptoms. Patients should of course be monitored for possible adverse events. For therapeutic or prophylactic use, one or more nAChR inhibitors will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

Pharmaceutical compositions useful in the practice of this invention include suitable dosage forms for oral, parenteral (including subcutaneous, intramuscular, intradermal and intravenous), transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case, conventional suspending agents may be employed. Conventional preservatives, buffering agents and the like also may be added to the parenteral dosage forms. The pharmaceutical compositions may be prepared by conventional techniques appropriate to the desired preparation containing appropriate amounts of the nAChR inhibitor(s). See, for example, Remington's Pharmaceutical. Sciences, Mack Publishing Company, Easton, Pa., 18th edition, 1990.

In making pharmaceutical compositions for use in the invention, the nAChR inhibitor(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents, or flavoring agents. The compositions of the invention may be formulated so as to provide quick, sustained, or delayed release of the nAChR inhibitor(s) after administration to the subject.

The compositions are preferably formulated in a unit dosage form. The term "unit dosage form" refers to physically discrete units suitable as unitary dosages for human subjects and other mammals, each unit containing a predetermined quantity of active material calculated to produce the desired prophylactic or therapeutic effect over the course of a treatment period, in association with the pharmaceutical carrier.

The nAChR inhibitor(s) can also be formulated in a controlled release form, e.g., delayed, sustained, or pulsatile release. In some embodiments, the nAChR inhibitor is provided in a slow or sustained (extended) release preparation, e.g., to maintain stable lithium plasma levels over the course of about 6 hours, about 8 hours, about 12 hours, about 18 hours, or even about 24 hours or longer. In some embodiments, the nAChR inhibitor is provided in a once-a-day formulation.

The nAChR inhibitor(s) can also be administered concomitantly with other drug therapies, including but not limited to other antidepressant drug therapies or other drug therapies for treating other emotional disorders. In some embodiments, the nAChR inhibitor(s) is administered to the subject as a monotherapy, with no other mood stabilizing, antidepressant, antipsychotic, or anxiolytic medication concurrently administered with the nAChR inhibitor(s), and preferably not administered less than one week prior to administration of the nAChR inhibitor(s).

In another aspect, the invention concerns a method for determining the efficacy of a treatment for suicidal ideation or suicidal behavior, comprising identifying a subject as having suicidality symptoms using a suicidality scale that is capable of direct mapping to the Columbia Classification Algorithm for Suicide Assessment (C-CASA); administering a candidate treatment to the identified subject; and determining whether the candidate treatment is effective in preventing, reducing (e.g., reducing the severity or frequency), or eliminating suicidal ideation or behavior. Preferably, the suicidicality scale is the Sheehan Suicidality Tracking Scale (S-STS). Thus, in some embodiments, the method comprises identifying a subject as having suicidality symptoms of more than zero as measured by the S-STS prior to said decreasing; administering a candidate treatment to the identified subject; and determining whether the candidate treatment is effective in preventing, reducing, or eliminating suicidal ideation or behavior in the identified subject.

Determination of effectiveness can be ascertained by comparing the effects of the candidate treatment on the identified subject to that of an appropriate control (e.g., a placebo). Improvement on the suicidality scale is indicative of treatment efficacy. Effects of the candidate treatment that may be evaluated include, but are not limited to, physiological effects and behavioral effects (e.g., symptoms of suicidal tendency, such as suicidal ideation or suicidal behavior).

Another aspect of the invention is an article of manufacture useful for determining the efficacy of a treatment for suicidal ideation or behavior. In some embodiments, the article of manufacture comprises a computer-readable medium having computer-executable instructions stored thereon for requesting information from a subject that is necessary for evaluating the subject using the S-STS.

In some embodiments, the computer-executable instructions embodied in the computer-readable medium further provide instructions for performing the following steps: (a) recording the information obtained from the one or more subjects; or (b) outputting the information obtained from the one or more subjects; or (c) both (a) and (b).

The computer-readable medium may be, for example, a hard disc (hard drive), floppy disc, compact disc (CD), digital video disc (DVD), flash memory device, random access memory (RAM), and read only memory (ROM).

The article of manufacture can include one or more peripheral devices. For example, in some embodiments, the article includes an input device by which a user can input the information used to determine the efficacy of a treatment for suicidal ideation or suicidal behavior. For example, the user (e.g., a clinician) can input responses to questions from the S-STS.

Optionally, the computer-executable instructions embodied in the computer-readable medium further include instructions for outputting: (a) the one or more subject's responses to the questionnaire on a computer display device, such as a monitor and/or printer; or (b) an indication of whether a treatment is effective for the treatment of suicidal ideation or behavior; or both (a) and (b).

In some embodiments of the article, requesting information from the subject comprises presenting the one or more subjects with a questionnaire requesting the information. The questions can be in any language, and should be understandable to the one or more subjects or be understandable to an intermediary (e.g., a human or device) that may in turn translate for the one or more subjects.

In some embodiments of the article, the questionnaire is presented from a server to a client over a computer network. In some embodiments, the questionnaire is presented to a user that presents the questionnaire to the one or more subjects. In some embodiments, the questionnaire is presented to the one or more subjects themselves (directly). In some embodiments, the questionnaire is presented to the one or more subjects on a display of a computer (e.g., handheld, laptop, desktop, etc.). In some embodiments, the questionnaire is presented to the one or more subjects via the Internet. Preferably, the one or more subjects are also provided with an interface over the Internet.

In some embodiments of the article, the questionnaire is presented to the one or more subjects on a paper printout.

In some embodiments of the article, presenting the one or more subjects with a questionnaire comprises a combination of two or more of the aforementioned modes of question presentation (e.g., computer display, paper, oral).

As used herein, the singular forms "a", "and", and "the" include plural referents unless the context clearly dictates otherwise. Thus, for example, reference to an "nAChR inhibitor" or "nAChR antagonist" includes a plurality of such inhibitors and antagonists, and reference to "the nicotine acetylcholine receptor" includes reference to one or more receptors and equivalents thereof known to those skilled in the art, and so forth.

As used herein, the term "major depressive disorder" refers to the mood disorder as defined by the American Psychiatric Association: Diagnostic *and Statistical Manual of Mental*

*Disorders*, Fourth Edition, Text Revision. Washington D.C., American. Psychiatric Association, 2000, or DSM-IV, which is incorporated herein by reference in its entirety.

The phrase "treatment of suicidal ideation", or grammatical variations thereof, means a reduction in, or elimination of, suicidal ideation in a person or patient, potentially leading to a lower frequency of suicide attempts and/or other suicidal behaviors.

The phrase "treatment of suicidal behavior", or grammatical variations thereof, means a reduction in, or elimination of, suicidal behavior in a person or patient. Treatment of "suicidal ideation or behavior" includes situations where the subject is suffering from suicidal ideation, suicidal behavior, or both suicidal ideation and suicidal behavior.

The term "advertising" refers to notifying, informing, and/or apprising one or more individuals of information (e.g., the efficacy of a pharmaceutical or biological product, such as an nAChR inhibitor, for treating or reducing an indication, such as suicidal ideation or behavior), such as by mass media, including, but not limited to, newspaper, magazine, and internet advertisements, television commercials, and billboard signs. The term "advertising" as used herein also includes including a statement that the pharmaceutical or biological product can treat or reduce the indication in the labeling for the pharmaceutical or biological product.

The term "marketing" refers to the act or process of selling a product, such as asenapine or an nAChR inhibitor, including, but not limited to, any offer for sale or sale of a product.

The term "pharmaceutical or biological product" refers to any product containing asenapine or one or more nAChR inhibitors, including, but not limited to, pharmaceutical compositions containing one or more nAChR inhibitors, and unit dosage forms, such as tablets and capsules, containing one or more nAChR inhibitors.

As used herein, the term "suicide attempt" means an action by a subject committed either with willful intent or as a response to internal compulsions or disordered thinking that puts him/herself at high-risk for death.

As used herein, the term "clinical trial" means any research study designed to collect clinical data on responses to a particular treatment, and includes, but is not limited to, Phase I, II, and III clinical trials. Standard methods are used to define the patient population and to enroll subjects.

As used herein, the term "active ingredient" refers to an inhibitor of nAChR activity (an nAChR inhibitor).

As used herein, the term "agonist" refers to a substance that activates receptor function; and the term "antagonist" refers to a substance that interferes with receptor function. Antagonists are of two types: competitive and non-competitive. A competitive antagonist (or competitive blocker) competes with the neurotransmitter for the same binding site. A non-competitive antagonist or blocker inactivates the functioning of the receptor by binding to a site other than the acetylcholine binding site.

"nAChR antagonist" refers to an nAChR inhibitor that binds substantially specifically to a nicotinic cholinergic receptor (nAChR) but fails to cause its associated ion channel to open. However, this failure of the channel to open in turn results in a pharmacological effect. This definition includes partial nAChR antagonists, which are nAChR inhibitors that, when bound to a nAChR, are less likely than a pure nAChR antagonist to block activation, but blocked activation does occur at least part of the time. nAChR antagonists can be competitive or non-competitive antagonists.

As used herein, the term "mixed agonist/antagonist" and "compounds exhibiting a mixed agonist/antagonist nAChR profile" refer to compounds that act as both agonists and antagonists toward at least one nAChR subtype. The agonist and antagonist activity can occur at the same nAChR subunit or at different nAChR subunits. Mixed agonists/antagonists include those compounds which, upon exposure to an nAChR, initially increase receptor activation, but will subsequently decrease receptor responsiveness ("agonist-induced residual inhibition"). Agonist-induced residual inhibition includes classical desensitization produced by the binding of agonist to the activation sites, or alternatively decrease in subsequent evoked responses due to the effect of agonist binding at sites other than those sites which promote activation. These compounds may sometimes be described as "agonists" or "partial agonists" in the scientific literature. Methods for identifying nAChR modulators such as nAChR antagonists are known in the art (see, for example, Bertrand D. et al., *Proceedings of the National Academy of Sciences of the United States of America*, March 1990, 87(5):1993-1997; Bertrand D et al., *Journal of Receptors and Signal Transduction*, 1997, 17(1-3):227-242; Smulders C. et al., *Toxicological Sciences*, 2004, 82:545-554; Corringer P-J et al., *J. Neurosci.*, 1998, 18(2):648-657; and Leisgen C. et al., In Patch-Clamp Methods and Protocols, *Methods in Molecular Biology*, 2007, 403:87-109.

As used herein, the term "binding" refers to the formation of a complex involving a receptor (e.g., an nAChR such as nAChR subtypes having alpha4 and beta2 subunits or alpha7 subunits) and a ligand, and "binding affinity" refers to a compound's capacity to bind to a receptor. Binding affinity may be quantified, for example, by $K_i$.

A compound may exhibit "selective" binding, by which is meant that the compound's affinity for binding to one or more particular receptor(s) is greater than the compound's affinity for binding to one other receptor, multiple other receptors, or all other receptors. For a compound that exhibits selective binding, therefore, the binding constant $K_i$ for the compound binding with one receptor is lower than the $K_i$ for the compound binding with one or more other receptor(s). For example, a compound that is selective for receptor "A" over receptor "B" will have a binding constant ratio $K_i(A)/K_i(B)$ that is less than 1/1.

As used herein, the "prodrug" includes compounds with moieties, which can be metabolized in vivo. The nAChR inhibitors used in the formulations and methods of the invention may be prodrugs. Generally, the prodrugs are metabolized in vivo by esterases or by other mechanisms to active drugs. Examples of prodrugs and their uses are well known in the art (See, e.g., Berge et al., 1977, "Pharmaceutical Salts", *J. Pharm. Sci.* 66:1-19; Silverman, 2004, "The Organic Chemistry of Drug Design and Drug Action", Second Ed., Elsevier Press, Chapter 8, pp. 497-549). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halogen, or methoxy substituents) aryl and aryl-lower alkyl esters, amides, lower-alkyl amides, di-lower alkyl amides, and hydroxy amides. Preferred prodrug moieties are propionoic and succinic acid esters, acyl esters and substituted carbamates. nAChR inhibitors that are converted to active forms of inhibitors through other mechanisms in vivo are also included in the term "prodrug".

The terms, "subject", "patient" or "individual" are used interchangeably herein, and refer to a mammalian subject to be treated, with human patients being preferred. In some cases, the methods of the invention find use in experimental animal models, in veterinary application, and in the development of animal models for disease, including, but not limited to, rodents including mice, rats, and hamsters; and primates.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

General Directions and Scoring Instructions for Sheehan-Suicidality Tracking Scale (S-STS)

The S-STS is shown in FIGS. 1A-1C. The C-CASA mapping procedure is shown in FIG. 2. Scoring instructions for the S-STS of FIGS. 1A-1C are provided below.
  Use data from all sources.
  The S-STS can be patient rated and clinician administered.
  Consider severity, frequency and time frame in your responses.
  Different timeframes may be used with this scale (e.g., "in the past week", "in the past month", "since the last visit", or "ever"). However each study should adopt a consistent time throughout the study, if the scale is to be used as an outcome measure. If it is used as a safety data capture system only, then "since the last visit" is the most appropriate time frame to use.
  All clinicians using this scale in clinical trials should receive instruction using approved training materials for S-STS. This is to ensure consistency in the understanding and application of definitions for each scale item and each C-CASA item coded.
At Screening, exclude anyone wit a score of:
  3 or 4 on either Questions 2, or 3, or 4, or 8.
  2 or higher on any Question 1a, 5, 6, 7, or 9.
During the Study:
  call the medical monitor if the score is 3 or 4 on either Question 3 or 4 or if the score is 2 or higher on any Question 1a, 5, 6, 7, or 9.
  on items of concern in your clinical judgment, clarify and ask for examples from patient.
Scoring S-STS
  7 scores are derived from the S-STS in addition to individual item scores:
1) Total Score
  Sum the scores (0-4) for each of the following:
  Questions 1a, 2, 3, 4, 5, 6, 7, 8, 9, 12 and 13.
2) Suicidal Ideation score
  Sum the scores (0-4) for each of the following:
  Questions 2, 3, 4, 5 and 6.
3) Suicidal Behavior score
  Sum the scores (0-4) for each of the following:
  Questions 1a, 7, 9, and 12.

4) Total Number of Suicidal Events
  From Questions 1.0 plus 11 plus
  Total number of Suicidal Ideation Events (from bottom of page 2 (FIG. 1B)).
5) Number of Suicidal Ideation Events
  Total number of Suicidal Ideation Events (from bottom of page 2 (FIG. 1B)).
6) Number of Active Preparatory (Suicidal) Events
  From Question 11.
7) Number of Suicidal Attempt Events
  From Question 10.
  There are no numeric scores assigned for responses to questions 1 or 1b in the calculation of the Total Score, the Suicidal Ideation score or the Suicidal Behavior score.
  If information from the S-STS needs to be coded as an adverse event in a research study, classify the adverse event by the C-CASA category number and C-CASA category name when naming the adverse event (see S-STS to C-CASA mapping Table in FIG. 2).
  Interrupted attempts and aborted attempts are NOT classified as suicide attempts, but should be scored under either suicidal ideation or suicide plans or suicide preparatory behavior—whichever most accurately applies in each case.
  S-STS uses the same definitions for suicide assessment as outlined in C-CASA (Columbia Classification Algorithm of Suicide Assessment) presented in Posner K, Oquendo M A, Gould M, Stanley B, Davies M. *Am J Psychiatry* 2007; 164: 1035-1043.
  Scoring instructions for the alternative S-STS of FIGS. 3A-3C are provided below.
General Directions & Scoring Instructions
  Use data from all sources.
  The S-STS can be patient rated and clinician administered.
  Consider severity, frequency and time frame in your responses.
  Different timeframes may be used with this scale (e.g. "in the past week", "in the past month", "since the last visit", or "ever"). However, each study should adopt a consistent time throughout the study, if the scale is to be used as an outcome measure. If it is used as a safety data capture system only, then "since the last visit" is the most appropriate time frame to use.
  All clinicians using this scale in clinical trials should receive instruction using approved training materials for S-STS. This is to ensure consistency in the understanding and application of definitions for each scale item and each C-CASA item coded.
At Screening (past month timeframe), exclude anyone with a score of:
  3 or 4 on either Questions 2, or 3, or 4, 5 or 9.
  2 or higher on any Question 1a, 6, 7, 8 or 10.
During the study:
  call the medical monitor if the score is 3 or 4 on either Question 3, 4, 5 or 9 or if the score is 2 or higher on any Question 1a, 6, 7, 8 or 10.
  on items of concern in your clinical judgment, clarify and ask for examples from patient.
Scoring S-STS
7 scores are derived from the S-STS in addition to individual item scores:
1) Total S-STS Score
  Sum the scores (0-4) for each of the following:
  Questions 1a, 2, 3, 4, 5, 6, 7, 8, 9, 10, 13 and 14.
2) Suicidal Ideation Score
  Sum the scores (0-4) for each of the following:
  Questions 2, 3, 4, 5, 6 and 7.

3) Suicidal Behavior Score
   Sum the scores (0-4) for each of the following:
   Questions 1a, 8, 10 and 13.
4) Total Number of Suicidal Events
   From Questions 11 plus 12 plus
   Total number of Suicidal Ideation Events (from bottom of page 2 (FIG. 3B)).
5) Total Number of Suicidal Ideation Events
   Total number of Suicidal Ideation Events (from bottom of page 2 (FIG. 3B)).
6) Total Number of Active Preparatory (Suicidal) Events
   From Question 12.
7) Total Number of Suicide Attempt Events
   From Question 11.

There are no numeric scores assigned for responses to questions 1 or 1b in the calculation of the Total Score, the Suicidal Ideation score or the Suicidal Behavior score.

If information from the S-STS needs to be coded as an adverse event in a research study, classify the adverse event by the C-CASA category number and C-CASA category name when naming the adverse event (see S-STS to C-CASA mapping Table (FIG. 4)).

Interrupted attempts and aborted attempts are NOT classified as suicide attempts, but should be scored under suicide preparatory behaviors (Question 8) and classified accordingly in the "Level" column of Question 12.

S-STS uses the same definitions for suicide assessment as outlined in C-CASA (Columbia Classification Algorithm of Suicide Assessment" presented in Posner K, Oquendo M A, Gould M, Stanley B, Davies M. *Am J Psychiatry* 2007; 164: 1035-1043.

In research studies, it is recommended to use all 3 pages of the alternative S-STS (FIGS. 3A-3C) to be in compliance with FDA expectations outlined in the FDA Guidance Document on Suicidality Assessment. (Guidance for Industry. Suicidality: Prospective Assessment of Occurrence in Clinical Trials. Draft Guidance. September 2010. U.S. Department of Health and Human Services. Food and Drug Administration. Center for Drug Evaluation and Research (CDER)).

In clinical settings not involved in research, where the goal is to assess and monitor suicidality in a simple, thorough, yet efficient manner, Page 1 (FIG. 3A) alone is adequate.

EXAMPLE 2

The Treatment of Suicidality in Bipolar Disorder and Major Depressive Disorder: A Randomized, Double-Blind, Placebo-Controlled Study of Quetiapine XR Monotherapy and Lithium Monotherapy The specific aim of this study is to evaluate the efficacy of quetiapine monotherapy and lithium monotherapy in comparison to placebo in the treatment of suicidality in ambulatory Bipolar Disorder and Major Depressive Disorder.
Concerns in a Suicide Study The two main concerns in doing a study on suicidality are how to manage safety and how to measure efficacy. Both concerns need to be addressed in a manner that is sensitive to effects, comprehensive and scientifically credible. Each of these concerns is addressed in detail in the two sections below.

How to Manage the Safety Concerns in a Suicide Study

Almost all placebo controlled studies for the past 30 years in major depressive disorder and bipolar depression have allowed the inclusion of patients with suicidal ideation and some suicidality—as long as the suicidality was not severe enough to place the patient at unnecessary or unacceptable risk during the study. This study proposes to exclude any patients found to be at any higher suicide severity or risk than those included in these prior studies. The only difference in the proposed study is that patients will not be included if they do not have more than a zero total suicidality score and more than a zero suicidal ideation score at both screen and baseline. In other words, all patients will need to be in the mild to moderate range and no patient may have a suicidality risk that either the board certified psychiatrist or the patient deem an unnecessary or unacceptable risks for inclusion in the placebo controlled study.

In addition, the protocol specifically includes rescue provisions, defined below, to ensure that a patient whose risk rises to an unacceptable level at any time during the study is withdrawn from the study and provided with alternative treatments. Further, all patients will be immediately started on lithium at the end of the study and appropriate follow-up treatment arrangements made.

All patients will be expected to sign a contract for safety in the presence of a board certified psychiatrist investigator. As part of the contract, patients will agree not to make any suicide attempt and agree that they feel in sufficient control of their suicidal ideation and impulses that they feel comfortable in adhering to this contract for the duration of the study.

The decision to include or exclude a patient, based on suicide assessment, will be done by a board certified psychiatrist and not a research coordinator or any other member of the research team.

The Sheehan Suicidality Tracking Scale (S-STS) (9) will be independently rated by the clinician and the patient at each weekly visit throughout the 12 week study to monitor this issue thoroughly. The computerized data acquisition software will run a consistency check between the patient and clinician rated Sheehan Suicidality Tracking Scale (S-STS) and generate a report at each visit. The treating clinician will review the consistency check report before the patient leaves the office at the end of each study visit. The reviewing physician will attempt to reconcile any inconsistencies in ratings between the clinician and the patient rated Sheehan Suicidality Tracking Scale before the patient leaves the office at the end of the visit.

An independent Data Safety Monitoring Board (DSMB), made up of experts in suicidality, will be provided with monthly reports on suicidality and with any other important safety data to monitor the safety of the study implementation. More frequent (e.g. weekly) data can be provided to the Data Safety Monitoring Board if necessary. The study's electronic data capture system permits real-time data acquisition and complete data, without any missing data or double entries. The software used permits immediate data export of any and all study data to this board for its independent analysis and review. The investigator will consult on a regular basis with the Data Safety Monitoring Board to ensure adequate quality control and patient safety.

How to Measure Efficacy in a Suicide Study

Historically, suicidality is assessed in depression and bipolar studies by reviewing and analyzing either item 10 on the Montgomery Asberg Depression Rating Scale (MADRS) or item 3 on the Hamilton Depression Rating Scale (HAMD) and by assessing the adverse events or serious adverse event data. These methods are limited in scope and in the past few years have been deemed inadequate by the FDA and other regulatory agencies. Detection of the efficacy signal on suicidality was based on the post-hoc analysis of one item on each of the two depression scales and in many studies only one of the scales was used. Even then such scales were often not done at each week throughout the study.

The FDA has indicated that relying on the analysis of one item on one scale to track suicidality is not adequate or systematic enough. They now require that any suicidality scale used for this purpose be capable of direct mapping to the Columbia Classification Algorithm for Suicide Assessment (C-CASA) (10). Only two scales in existence currently meet this criterion—the Columbia Suicide Severity Rating Scale (C-SSRS) (11) and the Sheehan Suicidality Tracking Scale (S-STS) (9) (see FIGS. 1A-1C).

Of these, only the S-STS has been shown to be sensitive to treatment effects in discriminating between active drug and placebo (9). The S-STS is shorter, easier to administer, less ambiguous and available in both patient rated and clinician rated versions. It is also much easier to score (exemplified in Example 1) and to analyze statistically. It is also computerized, runs a consistency check between patient and clinician rated versions and is also available in an interactive voice recognition (IVR) version. It assesses all significant domains of interest in suicidal ideation and behaviors. The C-SSRS (11) has not been shown to be sensitive to detecting statistically significant differences between a medication and placebo in lowering suicidality scores in treatment studies. The C-SSRS has also changed multiple times over the past three years and has no published reproducible scoring procedure or published mapping procedure to the C-CASA system.

While a sample size larger than that proposed in this study may be needed to fully detect this efficacy signal, a power analysis of the data in this pilot study will provide a good assessment of the sample size needed to document this efficacy signal at a level that is statistically significant at $p \leq 0.05$.

Preliminary Studies

Lithium Carbonate

Lithium carbonate is indicated in the treatment of manic episodes and manic-depressive illness (bipolar I disorder). Maintenance therapy prevents or diminishes the intensity of subsequent episodes in those manic depressive patients with a history of mania (18-33).

Quetiapine has been shown to be superior to placebo as monotherapy in acute bipolar mania in hospitalized patients with bipolar I disorder in two large multi-center 12-week randomized placebo-controlled trials (18-20).

Atypical Neuroleptics & Quetiapine in the Treatment of Suicidality

In a randomized, double-blind, placebo-controlled trial in 542 outpatients of quetiapine in the treatment of bipolar I and II depression, Calabrese et al. (the Boulder 1 study) (23) reported in a secondary post-hoc analysis that both 300 mg/day and 600 mg/day were more effective than placebo in reducing suicidal ideation by week 8 (endpoint) (p<0.001). The reduction in suicidal ideation on quetiapine was approximately twice that of placebo as measured by item 10 on the Montgomery Asberg Depression Rating Scale (MADRS). The mean percent reduction in suicidal thoughts was she approximately 60% on quetiapine compared to approximately 30% on placebo.

Houston et al. (34) reported that the addition of olanzapine versus placebo to lithium or divalproex monotherapy significantly reduced suicidal ideation, as measured by the Hamilton Depression Scale-item 3 scores, in 58 bipolar I mixed state patients.

Ciaparelli et al. (35) reported that quetiapine was effective in lowering suicidality in treatment resistant psychotic bipolar patients over 24 months of observation, suggesting that the anti-suicide properties of clozapine seen in schizophrenia and in schizoaffective disorder may also be seen in bipolar disorder.

Quetiapine has also been shown to be superior to placebo when used in combination with lithium or divalproex in hospitalized adult patients with acute mania (21) and when used in combination with divalproex in adolescent patients with acute bipolar I mania (22).

Quetiapine has been shown to be superior to placebo in reducing depressive and anxiety symptoms in patients with a bipolar I or II disorder and an acute bipolar depression (23, 24). It has also been shown to reduce depressive symptoms more than haloperidol in schizophrenic patients with persistent ongoing symptoms (25). Its anti-manic properties have been hypothesized to be due in part to antagonism at dopamine (DA) $D_2$ receptors and its antidepressant and anxiolytic properties may be due to its serotonergic (5HT) properties (26).

Design

This is a randomized, double blind, placebo controlled, parallel-group, 12-week trial of quetiapine monotherapy compared to Lithium monotherapy in outpatient subjects with mild to moderate suicidality co-morbid with a diagnosis of bipolar I, II, or NOS disorder or Major Depressive Disorder. Approximately 180 subjects will be randomized to obtain 90 subjects who complete the 12-week trial (30 completers per treatment group). This calculation is based on drop-out rates in a similar patient population carried out by this group of collaborators. Subjects will be randomized to quetiapine or Lithium or placebo in a 1:1:1 ratio. No concomitant psychotropic medication will be allowed throughout the study except for prn lorazepam during the first two weeks for the management of affective and anxiety symptoms, prn zolpidem or zaleplon for the management of insomnia and benztropine for the management of extrapyramidal symptoms (EPS). Throughout the study, psychiatric scales will be used to assess suicidality and psychiatric symptoms. The presence of treatment-emergent adverse events will be monitored and recorded.

Inclusion Criteria

Criteria for entering this study will include all of the following:

1. Subjects must be at least age of 18 years of age and not older than 65.
2. Subjects must have bipolar I, II, or NOS disorder as defined by DSM-IV TR criteria (36) and be in a depressive episode or mixed state episode or have major depressive disorder current at both the screening and the baseline visit.
3. Subjects' manic/hypomanic symptoms must be no more than moderate in severity, defined as a CGI-BP<4 on the Overall Bipolar Disorder dimension (37).
4. Subjects' suicidality symptoms must be more than zero as measured by the Sheehan Suicidality Tracking Scale (S-STS) (9).
5. Subjects must not be receiving regular mood stabilizing, antidepressant, antipsychotic, or anxiolytic medication for at least one week prior to baseline. Patients receiving fluoxetine or depot antipsychotics should be off these medications for at least four weeks prior to baseline.
6. Subjects or their legally authorized representative must sign the Informed Consent Document after the nature of the trial has been fully explained.
7. If female, subjects must be: postmenopausal, surgically incapable of childbearing, or practicing medically acceptable effective method(s) of contraception (e.g., hormonal methods, barrier methods, intrauterine device) for at least one month prior to study entry and throughout the study.

Exclusion Criteria

Criteria for exclusion from this study will be any of the following:
1. Subjects who do not have bipolar disorder and are not in a depressive or mixed state episode or who do not currently have major depressive disorder by DSM-IV-TR criteria (36).
2. Subjects who are receiving treatment with an anti-manic or mood stabilizing medication (lithium, valproate, carbamazepine, or an antipsychotic), and in the investigators' judgment, require ongoing treatment with that medication.
3. Subjects whose manic symptoms are presently more than markedly ill i.e. who are severely ill (defined as a mania score of >5) on the CGI-BP mania dimension (37).
4. Subjects who have a zero score on the Sheehan Suicidality Tracking Scale (S-STS) at Screen or Baseline (9).
5. Subjects at the Screening visit who answer "yes" to the question B6 on the suicidality module of the MINI (39). This question asks: do you "feel unable to control these (suicidal) impulses"?
6. Subjects who at the Screening visit have a score of "3 or 4" on questions 2 or 3 or 4 or 8 or scores of 2 or higher on questions 1a or 5 or 6 or 7 or 9 of the Suicidality Tracking Scale (S-STS).
7. Subjects will be rescued from the study at any time after randomization if their scores on the Sheehan Suicidality Tracking Scale (S-STS) (9) cross the following severity thresholds: ≥3 on questions 2 or 3 or 4 or 8 or >2 on questions 1a or 5 or 6 or 7 or 9 or in addition any score on the Sheehan Suicidality Tracking Scale (S-STS) if in the judgment of the clinician the suicidality score and risk level are such that it would place the patient at unacceptable risk to continue in the study.
8. Subjects who do not sign a contract at the screening visit agreeing not to make a suicide attempt during the study.
9. Subjects who in the psychiatrist's judgment have current suicidality scores and a suicide risk level that would place them at unacceptable risk for inclusion in a 12-week placebo controlled study.
10. Subjects with clinically significant homicidal ideation (as measured by the Violence Tracking Scale (HTS).
11. Subjects with a current DSM-IV TR Axis I diagnosis of delirium, dementia, amnesia, or other cognitive disorders; a DSM-IV TR diagnosis of a substance dependence disorder within the past six months; a lifetime DSM-IV TR psychotic disorder (e.g., schizophrenia or schizoaffective disorder).
12. Subjects with serious general medical illnesses including hepatic, renal, respiratory, cardiovascular, endocrine, neurological, or hematological disease as determined by the clinical judgment of the clinical investigator. Subjects with hypo- or hyperthyroidism unless stabilized on thyroid replacement >3 months.
13. Subjects with a clinically significant abnormality in their pre-study physical exam, vital signs, EKG, or laboratory tests.
14. Subjects who are allergic to or who have demonstrated hypersensitivity or intolerance to either of the active study medications.
15. Women who are pregnant or nursing.
16. Subjects who have received an experimental drug or used an experimental device within 30 days.
17. Subjects who have a history of neuroleptic malignant syndrome.
18. A patient with diabetes mellitus (DM) fulfilling one of the following criteria:
    Unstable DM defined as enrollment glycosylated hemoglobin (HbA1c) >8.5%
    Admitted to hospital for treatment of DM or DM related illness within the past 12 weeks
    Not under physician care for DM
    Physician responsible for patient's DM care has not indicated that the patient's DM is controlled
    Physician responsible for patient's DM care has not approved the patient's participation in the study
    Has not been on the same dose of oral hypoglycemic drug(s) and/or diet for the 4 weeks before randomization. For thiazolidinediones (glitazones) this period should not be less than 8 weeks before randomization
    Taking insulin whose daily dose on one occasion in the past 4 weeks has been more than 10% above or below their mean dose in the preceding 4 weeks Note: If a patient with DM meets one of these criteria, the patient is to be excluded even if the treating physician believes that the patient is stable and can participate in the study.

Medication Dosing

The dose of each medication will be flexibly adjusted for each patient based on efficacy and tolerability. The medications will be titrated and dosed at a rate not exceeding that outlined in Table 1.

Quetiapine XR will be administered at an initial dose of 50 mg/day and will be titrated upward to a dose considered optimal by the investigator based on the subject's clinical response and adverse events, but not to exceed 150 mg/day during the second week on medication. Subsequently, quetiapine XR may be increased based on clinical response and tolerability to a maximum of 300 mg/day.

Lithium will be administered at an initial dose of 300 mg on a BID schedule. At the end of the week 1 visit, the dose will be increased to 300 mg in am+600 mg in pm based on each subject's tolerability of the bid dose. If the lithium 300 mg bid is associated with troublesome side effects, the dose will not be increased. Most patients tolerate 900 mg/day (300 in am+600 in pm). At week 2, a lithium level will be drawn. Subsequent upward titration of the lithium doses (not to exceed 300 mg/week) will be driven by the results of the lithium level until each patient is in a therapeutic range of 0.8-1.2 mEq/L. The dose in no case will exceed 1800 mg/day (900 in am+900 in pm).

Both quetiapine XR and Lithium and placebo will be taken on a BID schedule as outlined in Table 1. Patients in consultation with their physician may however elect to take their total daily dose at bedtime instead of the BID schedule, based on efficacy and tolerability. However this decision will not be taken lightly. Patients will be encouraged to take their medication on a BID schedule. From the second week onwards the physician may adjust the dosing up or down for each patient, based on patient tolerability and efficacy.

As needed study-prescribed (prn) use of lorazepam will be allowed for the management of affective and anxiety symptoms for the first two weeks of the study; a maximum of 2 mg per day will be allowed during the first week, and a maximum of 1 mg per day will be allowed during the second week. During the second week, the subject must be tapered off the lorazepam. For the final six weeks of the study, no lorazepam will be permitted. Zolpidem (10-20 mg/day) or zaleplon (10-20 mg/day) will be allowed for management of insomnia, and benztropine (0.5-3.0 mg/day) will be allowed for management of extrapyramidal symptoms. The latter three agents will be permitted throughout the study.

All other medications with psychotropic effects are prohibited from 1 week prior to baseline onwards.

TABLE 1

Maximum Daily Dosing Schedule in mgs and Tablet Equivalents (given bid).

| Visit | | Quetiapine XR Tablets | mgs. | Lithium Tablets | mgs. | Quetiapine XR Placebo Tablets | Lithium Placebo Tablets | Dosing level |
|---|---|---|---|---|---|---|---|---|
| Days 1-3 | 2nd | 0 + 1 | 0 + 50 | 0 + 1 | 0 + 300 | 0 + 1 | 0 + 1 | Level 1 |
| Days 4-7 | 2nd | 1 + 1 | 50 + 50 | 1 + 1 | 300 + 300 | 1 + 1 | 1 + 1 | Level 2 |
| Week 1-2 | 3rd | 1 + 2 | 50 + 100 | 1 + 2 | 300 + 600 | 1 + 2 | 1 + 2 | Level 3 |
| Week 2-3 | 4th | 2 + 2 | 100 + 100 | 2 + 2 | 600 + 600 | 2 + 2 | 2 + 2 | Level 4 |
| Week 3-4 | 5th | 2 + 3 | 100 + 150 | 2 + 3 | 600 + 900 | 2 + 3 | 2 + 3 | Level 5 |
| Week 4-5 | 6th | 3 + 3 | 150 + 150 | 3 + 3 | 900 + 900 | 3 + 3 | 3 + 3 | Level 6 |
| Week 5-6 | 7th | 3 + 3 | 150 + 150 | 3 + 3 | 900 + 900 | 3 + 3 | 3 + 3 | Level 6 |
| Week 6-7 | 8th | 3 + 3 | 150 + 150 | 3 + 3 | 900 + 900 | 3 + 3 | 3 + 3 | Level 6 |
| Week 7-8 | 9th | 3 + 3 | 150 + 150 | 3 + 3 | 900 + 900 | 3 + 3 | 3 + 3 | Level 6 |
| Week 8-9 | 10th | 3 + 3 | 150 + 150 | 3 + 3 | 900 + 900 | 3 + 3 | 3 + 3 | Level 6 |
| Week 9-10 | 11th | 3 + 3 | 150 + 150 | 3 + 3 | 900 + 900 | 3 + 3 | 3 + 3 | Level 6 |
| Week 10-11 | 12th | 3 + 3 | 150 + 150 | 3 + 3 | 900 + 900 | 3 + 3 | 3 + 3 | Level 6 |
| Week 11-12 | 13th | 3 + 3 | 150 + 150 | 3 + 3 | 900 + 900 | 3 + 3 | 3 + 3 | Level 6 |

Adjustment of Dose Using Lithium Levels

The 12 hr lithium level will be given to a "designated clinician" at each site who is not directly involved in doing any patient rating of any scales or case report forms during the study. Clinicians directly involved in patient rating and care throughout the study ("rating clinicians") will not see these results.

If a lithium level is above the acceptable range, for the study (i.e., in a toxic range), this designated clinician will immediately advise the rating clinicians involved with the patient to lower the dose. If the blood level is below a therapeutic range, the designated clinician will advise the rating clinician that the dose of study medication can be increased. To preserve the study blinding, the designated clinician will also advise the rating clinician to either increase or decrease the doses of a matching number of patients on placebo. The recommendation on adjusting the placebo doses will not be given at the same time as the recommendation to adjust the active drug to better preserve blinding. The designated clinician will keep a log of the study code and the timing and content of the recommendation, to ensure an equal balance of dose adjustments and direction of adjustments between the active drug and placebo.

Identification Number Assignments

All patients will receive a 7 digit patient screening I.D. number. The first digit (on the left) is the site number. The first four digits are assigned at screening in sequential order. For example, the first patient presenting for screening at site 1 gets the screening number 1001000, the second, 1002000, etc. The set of last three digits of the I.D. number is the medication number and is assigned in sequential order at the time the patient is randomized to the study drug.

| For Example Site 1 | Screening #/Medication # |
|---|---|
| 1001 001 | (screened & randomized to medication # 001) |
| 1002 000 | (non-starter: $2^{nd}$ patient screened only) |
| 1003 002 | ($3^{rd}$ patient screened & randomized to medication # 002) |
| 1004 000 | (non-starter: $4^{th}$ patient screened only) |
| 1005 003 | ($5^{th}$ patient screened & randomized to medication # 003) |
| 1011 000 | will be the screening number for the $11^{th}$ patient |

Each site will be assigned a range of numbers for screening (also called the "Confidential I.D. Number"). Study Site 1 will use the screening numbers 1001000-1999000; Study Site 2 will use the screening numbers 2001000-2999000. Study Site 3 will use the screening numbers 3001000-3999000.

Each site will be initially shipped a supply of medication to randomize 10 patients. Additional lots of randomized medication will be shipped to each site in blocks of 5 as needed until a total of 150 patients have completed the study at the combined sites. The 3 digit medication number assigned to the patient is used as the last 3 digits of the randomization number. The randomization number is a 7 digit number.

For the example given above of I.D. assignments for Site 1, the corresponding number for Site 2 is as follows:

| For Example Site 2 | Screening #/Medication # |
|---|---|
| 2001 001 | (screened & randomized to medication # 001) |
| 2002 000 | (non-starter: $2^{nd}$ patient screened only) |
| 2003 002 | ($3^{rd}$ patient screened & randomized to medication # 002) |
| 2004 000 | (non-starter: $4^{th}$ patient screened only) |
| 2005 003 | ($5^{th}$ patient screened & randomized to medication # 003) |
| 2011 000 | will be the screening number for the $11^{th}$ patient |

Assessments

Screening Visit(s)

The Screening Period will last a minimum of 2 to a maximum of 30 days. At the first screening visit (Visit 0), informed consent will be obtained. The MINI International Neuropsychiatric Interview 6 (MINI) (39), (which includes a Suicidality Assessment Module) will be performed to establish whether the patient meets DSM-IV TR (36) criteria for bipolar disorder I, II, or NOS, with a major depressive episode or for Major Depressive Disorder. The Sheehan Suicidality Tracking Scale (S-STS) (9) will be independently rated by the Clinician and the patient at this and each subsequent visit to assess the degree of suicidality. The computer on which these S-STS ratings are captured at the visit will run a consistency check between the patient and clinician rated S-STS scales and provide an immediate report to the clinician, so that any differences can be re-checked in the interest of patient safety. The CGI-BP (37) and the CGI-S (38) will be performed to establish the severity of bipolar affective symptoms and depressive disorder, respectively. Subjects will keep a mood chart in between visits to help them follow their affective and depressive symptoms. The subject's manic symptoms must be no more than markedly ill (i.e., is not severely ill (defined as a CGI-BP Score>5 on the mania dimension)), and his/her depressive symptoms must be at least moderate in severity (a CGI-S of >4) for him/her to be able to continue in the screening process and enter the randomized phase. The screening assessments will include a medical history, a physical exam, height, weight, vital signs, an electrocardiogram (EKG) and laboratory studies (Complete Metabolic Profile, TSH, Free T4, Hemoglobin A1c (HgA1c), Lipid profile, complete blood count (CBC) with differential+platelets, urinalysis, serum pregnancy test and urine drug screen). These assessments will be used to determine whether subjects meet the study eligibility criteria.

Baseline Visit

A flow chart of patient evaluations is shown in Table 2. At baseline (Visit 1), subjects whose screening evaluations continue to meet all inclusion/exclusion criteria may enter the study and be randomized. These evaluations will include repeating the Clinical Global Impression modified for bipolar illness (CGI-BP) (37) and the Clinical Global Impressions Scale—Severity for depressive symptoms (CGI-S) (38) to ensure the subject continues to have no more than moderately severe bipolar affective symptoms and at least moderately depressive symptoms. Baseline ratings will include: the Sheehan Suicidality Tracking Scale (S-STS) (9) to assess suicidality; the Violence Tracking Scale (HTS) to assess Violence; the Hamilton Anxiety Scale (HAM-A) (40) to assess anxiety symptoms; the Young Mania Rating Scale (YMRS) (41), the Irritability Scale, (SIS), and the Rapid Ideas Scale (RISC) to assess manic symptoms; the Montgomery Asberg Depression Rating Scale (MADRS) (42) to assess depressive symptoms. Subjects will also be evaluated with the CGT-BP, and the Sheehan Disability Scale (SDS) (43-44). The Family Impact Scale (FIS) will be administered. The Abnormal Involuntary Movement Scale (AIMS) (45), Simpson Angus Scale (SAS) (46), and Barnes Akathisia Rating Scale (BARS) (47) will be administered to assess for extrapyramidal symptoms. Blood pressure, pulse, and weight, will be measured. Study medication will be dispensed by the Physician Investigator in the form of 50 mg capsules of quetiapine or 300 mg of lithium. The dose range of quetiapine will be 50 to 300 mg/day. The dose range of Lithium will be 300 to 1800 mg/day.

Treatment Period

Study visits will occur every week (+3 days) through the eight weeks of treatment. It is expected that the study medication will be gradually increased to an optimal dose during the first several weeks of treatment. The following procedures will be completed at each visit.

Collect unused medication, perform study drug accountability, and record dosage of study drug used. A subject's unused study medication can be re-dispensed back to the subject.

Review mood chart and administer the Sheehan Suicidality Tracking Scale (rated by both patient and clinician independently), Clinician Global Improvement-21 point scale (CGI-I-21), Patient Global Improvement –21 point scale (PGI-21) (22) HTS, HAM-A, YMRS, SIS, RISC, MADRS, CG1-BP, and SDS ratings.

Assess and record adverse events. An adverse event is defined as ANY treatment emergent event or as any pre-existing condition that increases in frequency or severity during the course of the study.

Perform AIMS, SAS, and BARS.

Obtain blood pressure, pulse, and weight.

Record concomitant medication use.

Adjust study medication dose (if necessary) and dispense study drug.

A lithium level will be drawn at weeks 2, 3, 4, 5 and 12 or early termination visit. When the lithium level reaches a therapeutic range, further lithium levels will not be drawn until week 12. The lithium levels at weeks 3, 4 and 5 will only be done if the lithium level is deemed "not in the therapeutic range".

Final Evaluation (Week 8)

The following evaluations will be conducted at the completion of, or early withdrawal from, the 8-week treatment phase. All psychiatric evaluations and all other final study procedures (including a repeat physical exam, EKG, and laboratory studies) will be completed prior to the discontinuation of quetiapine. The evaluations to be performed are:

Collect unused study medication, perform study drug accountability, and record dosage of study drug used.

Review mood chart and perform S-STS (patient and clinician rated), CGI-21, HTS, HAM-A, YMRS, SIS, RISC, MADRS, CGI-BP, PGI-21, and SDS ratings.

Repeat Family Impact Scale (FIS)

Assess and record adverse events.

Obtain blood pressure, pulse, weight.

Perform physical examination, AIMS, SAS, BARS.

Laboratory studies (Complete Metabolic Profile, Hemoglobin A1c (HgA1c), Lipid profile, CBC with/diff+platelets, Urinalysis, serum pregnancy test).

Repeat EKG.

Record concomitant medication use.

Adjust study medication dose (if necessary) and prescribe drug (if subject has responded and chooses to continue on study medication), or dispense study medication for taper or discontinuation (if subject has not responded or if subject chooses to discontinue study medication for any reason).

Early Termination Visit

In the event of an early termination visit, the usual scales for that patient's weekly visit will be completed. If they terminate at week 4, then the week 4 visit scales are completed.

In addition to the above, the following termination data will be collected:

Physical examination, EKG, laboratory tests (complete metabolic profile, Hemoglobin A1c (HgA1c), lipid profile, CBC with/diff+platelets, urinalysis, serum pregnancy test), lithium level, Family Impact Scale and Termination Record Form.

Termination Criteria

Subjects will be terminated from the protocol if:

The CGI-BP or CGI-I rating for change is "very much worse," the YMRS is >21, or the MADRS is >40.

The subject manifests signs of, or, shows evidence of clinically significant suicidality or homicidal ideation that would place them at unacceptable risk to continue in the study. Subjects who are suicidal or homicidal or who require hospitalization will be terminated from the protocol to allow for unencumbered medication changes.

In the absence of the above, subjects will be terminated at the treating psychiatrist's discretion in response to symptoms of sufficient severity that medication changes are warranted as described above.

Subjects may withdraw or be withdrawn from the protocol at any time, for any reason, and such terminations will be documented. All subjects who are terminated from the protocol will receive at least:

3 additional physician visits.

Referrals for other appropriate sources of continued care.

The option to receive open-label effective medications for bipolar disorder as clinically indicated.

Data Collection and Analysis

Electronic Data Capture

All the standardized data captured in this study, except for the history, the laboratory results, the EKG, the physical exam form and the informed and HIPAA forms will be directly recorded at the time of the visit into an electronic data capture database program on a Tablet PC or a Laptop PC, instead of first recording it on to a paper source document and later copying this information into a computer after the visit is completed. All the data capture forms (including scales, structured interviews, medication monitoring, adverse events concomitant medication tracking) for this study will be in the Tablet PCs. The appearance and layout of these forms in the Tablet PC mirrors those traditionally used in paper case report forms. Both the physician and patient will enter their data directly into the Tablet PC at the time of the visit. The database file in the Tablet PC is the source document for this study.

Direct entry electronic data capture (EDC) at the time of the visit, eliminates the need for later data entry by manual key punching into a computer from paper source documents, which is associated with transcription errors, personnel costs and delays. EDC eliminates the problem of missing values and double entries, since the software program in the Tablet PC will not save data from scales, unless all questions are answered. EDC is also programmed to make it impossible to give two responses to one question, where only one response is required.

At the end of each visit, the completed forms can be printed out via the PC wireless card in the Tablet PC and then filed in ring binders for later audit as paper case report forms. The data in the Tablet PC can be sent electronically to a sponsor daily or as often as required. This permits the sponsor to monitor patient enrollment and to monitor adverse events and other data of interest as the study progresses. It substantially reduces the need for site monitors, since monitoring can now be done centrally in-house by the sponsor. At the end of the study, or sooner if needed, the data can be exported directly from the Tablet PC in a form that can be read in Excel or in any statistics package on any other computer.

Data Analysis Plan

The primary comparison of interest is quetiapine versus Lithium versus placebo using the Sheehan Suicidality Tracking Scale (S-STS)—both clinician rated and patient rated versions. Secondary comparisons include quetiapine versus Lithium versus placebo for the following measures: the HTS, the HAM-A total score, the psychic and somatic factor scores of the HAM-A, the YMRS total score, the SIS total score, the RISC total score, the MADRS total score, the CGI-21, the PGI-21, the CGI-BP, the FIS, and the work, social, and family disability (SDS) scores. Additional comparisons of interest include the use of adjunctive anxiolytic and hypnotic medication, adherence to study medication, frequency and severity of side effects, and reasons for early termination.

The comparability of treatment groups will be assessed at baseline using parametric statistics for continuous variables (e.g., age) and chi-square or appropriate non parametric statistic, with a continuity correction where indicated, for categorical variables (e.g. gender, previous use of medications).

Efficacy analyses will be based on the intent-to-treat (ITT) population. For the purpose of the study, the ITT population will be defined as all patients who are randomly assigned to treatment, receive at least one dose of study medication, and have at least one post-baseline assessment. For these analyses, missing data will be carried forwards using the last-observation-carried forwards (LOCF) technique. Because of the relatively small size of the sample (30 completed per treatment group) data will be pooled for the three centers. Analyses will also be carried out on the observed cases dataset although these analyses will be considered secondary and supplemental to the primary LOCF analyses.

Repeated measures analysis of covariance (ANCOVA) with baseline scores as a covariate will be the main method for assessing the efficacy of quetiapine versus Lithium versus placebo for the primary efficacy variable, improvement on the Sheehan Suicidality Tracking Scale (S-STS)—both clinician rated and patient rated versions. Repeated measures analysis of covariance (ANCOVA), with baseline score as a covariate, will be used to compare the efficacy of quetiapine, Lithium, and placebo for the secondary measures HTS, HAM-A, YMRS, SIS, RISC, MADRS, the CGI-21, the PGI-21, CGI-BP, FIS and SDS scales. Non-parametric statistics (e.g., chi-square with a correction for continuity as indicated) will be employed to examine potential differences in the use of adjunctive anxiolytics and hypnotics, adherence to study medication, and reasons for early termination. All statistical tests will be two-tailed and carried out at an alpha level of 0.05.

An additional analysis of the primary efficacy measures will be conducted using the ETRANK statistical method developed by Richard Entsuah (48). This analysis is included to provide a potentially more sensitive and accurate alternative to the LOCF technique for imputing missing data. The method, is a modification and extension of Gould's (49) ranking approach. It accounts for treatment related (informative censoring) dropouts by using a nonparametric (randomization) method to analyze incomplete repeated-measures data.

With this technique, the observed full data set is used and the pattern, time, reasons and proportion of study withdrawals are incorporated in the statistical method. As Entsuah observes, parametric missing data methods such as Mixed Effects models, Hierarchical Linear Models (HLM), and Imputations methods need to be validated using the assumptions of Missing at Random (MAR) and Missing Completely at Random (MCAR) (50). In contrast, the ETRANK principle is not based on these assumptions. All available data are included, regardless of the reason for early termination from the study, and withdrawals due to adverse events or lack of efficacy are assigned weights, which reflect discontinuation due to improvement, deterioration, and time. Patients who have only baseline measurements who discontinue the study may be included in the computations.

For all numeric variables, assumptions of normality and homogeneity of variance will be assessed by examining normal probability and residual plots. If assumptions of normality and homogeneity of variance are not met, additional analyses will be performed in order to assess the robustness of the conclusions from the primary analysis. This will include investigation of appropriate transformations of the efficacy variable and if an appropriate transformation cannot be identified, non-parametric methods will be used (i.e., the Wilcoxan Rank Sum test).

Safety analyses will be based on all patients receiving medication at baseline (the intent to treat population). Treatment emergent differences in the AIMS, BARS and SAS total scores will be analyzed using one-way analysis of variance at each study week. One-way analysis of variance will also be used to examine weekly differences in vital signs (blood pressure and pulse). A listing of the final dose achieved by each patient and its relationship with rating scales will be provided. In addition, a listing of all adverse experiences, abnormal clinical values, abnormal vital signs (blood pressure and pulse) and termination data will be supplied. In addition, all efficacy measures over the course of the study will be presented and summarized in graphs and tables. Continuous data will be summarized by means, standard deviations, medians, maximum, minimum and number of patients. Categorical data will be summarized by counts and percentages.

The data for a final endpoint visit will not be included in the efficacy analysis if the date of that visit is ≥12 days from the previous visit at which medication was dispensed. The reason for this is to exclude patients from the endpoint efficacy analyses if they have been off their study medication or out of study medication for at least 2 days at endpoint. All safety data on these patients will be included in the safety analyses. In addition, endpoint efficacy data will be excluded on any patient if their study exit is associated with a protocol violation that could influence efficacy (e.g. taking a benzodiazepine or lithium, or not taking study medication for an extended period).

Power Analysis

There are no published studies on suicidality on which to base a power calculation. The sample size of 30 completed patients per treatment arm was chosen because it is typically the minimum sample size needed to provide normally distributed data on most of the scales used as outcome measures. This will allow analysis of the data using parametric analyses, thereby increasing the sensitivity of the analyses. Such a sample size will provide us with data that will permit a power analysis to be run on the results and to calculate the sample size that would be needed to statistically separate active drug from placebo should there be a difference that falls is not statistically significant at p<0.05. This would be helpful in planning future larger studies on suicidality.

Using a simple t-test on change from baseline in standard bipolar disorder studies to estimate a lower bound on power, the discernible effect sizes are:

| Number of patients per arm | | | |
|---|---|---|---|
| 30 | 25 | 20 | |
| 0.74 | 0.81 | 0.91 | 80% power, statistical significance = 0.05 |

Using a repeated measures analysis, a higher power and the ability to discern smaller effect sizes can be expected.

Data Monitoring

The study data will be monitored by the coordinating site at the University of South Florida College of Medicine. All sites will provide the coordinating site with enrollment logs monthly generated from the study software computer program. This will certify work done and will be the basis for the payments monthly to each site. The computer databases of completed work will also be sent to the coordinating site monthly for data monitoring purposes.

A study start-up teleconference will be held before the study begins, at intervals during the study, and as often as deemed necessary by the coordinating site and at the study close-out. Communication by telephone, fax, e-mail and mail may be used as needed to supplement the teleconferences. The purpose of these teleconferences is to verify 1) adherence to the protocol and 2) the completeness and accuracy of the direct data entry and any additional case report forms, informed consent documents and the clinical stock record. Adequate time for these teleconferences should be allocated by the investigators at each site. Patients' source documents and PC databases will be available for review.

A source document is defined as the place where the original information is first recorded. Most of the data will be directly entered at the time of the visit into a computer database program designed specifically for the study. The database file in the PC will therefore be the source document for almost all of the data in the study. A paper case report form may be a source document if the original information is first recorded there. Unnecessary duplication or re-transcription of data will be avoided where possible so as to insure accuracy and avoid transcription errors. Interim checks on the progress of the study will be made by telephone and by sharing of enrollment logs.

Data Safety Monitoring Board

Because of the unique safety concerns about conducting a study of this kind, a data safety monitoring board will be set up to monitor safety concerns, particularly relating to suicidality. Because the data in this study is being collected in real time the data will be relayed to the chairperson of the data safety monitoring board weekly for review with a summary report of the Sheehan Suicidality Tracking Scale (S-STS) results on individual patients. The data safety monitoring board will be provided a copy of the software and export engine so that they can independently assess any information they need to know to ensure every effort is being made to properly provide for patient safety.

Data Storage and Confidentiality

Back-ups of the data in the computer database file will be made daily and stored at each site. Strict measures will be taken at each site to ensure that tablet PCs or laptops used for the study and the back-up data records are kept under lock and key when not in use to ensure confidentiality. All data will be verified for accuracy before being transferred into a statistical package for data analysis.

Human Subjects

Subjects will include 180 randomized patients to yield 90 completed outpatients with lifetime bipolar I disorder, bipolar II disorder, or bipolar disorder NOS or Major Depressive Disorder by DSM-IV-TR criteria (25), who have more than zero suicidality at the study screening and baseline visits (but whose suicidality is not at a level of severity that will place them at unacceptable risk during the study). Subjects must not be on other psychotropic medications except pm use of lorazepam (for the first 2 weeks of the study), zolpidem, or zaleplon. Subjects must sign a contract not to suicide during the study. Subjects must be ≥18 years of age, be able to provide informed consent, and if female, be postmenopausal, surgically incapable of childbearing, or practicing medically acceptable method(s) of contraception (e.g., hormonal methods, intrauterine device, barrier methods) for at least 1 month prior to study entry and throughout the study. Exclusion criteria include subjects with a current DSM-IV Axis I diagnosis of delirium, dementia, amnesia, or other cognitive disorders, a lifetime psychotic disorder (e.g. schizoaffective disorder or schizophrenia), or a substance dependence disorder within the past six months; those with clinically significant suicidal or homicidal ideation; those with serious or unstable general medical illnesses; those who are allergic to or who have demonstrated hypersensitivity to quetiapine or lithium; and females who are pregnant or nursing. Subjects will be recruited from local physician referrals and by advertising.

Safety and Subject Protection

A number of measures are included to ensure subject safety in this protocol. The informed consent process allows the subjects to read the informed consent at their leisure. It is then reviewed with the subject by the study coordinator or investigator. The investigator will be available to answer all questions a patient may have about the study and their participation. Only then will the subject sign and date the informed consent document and the HIPAA document.

Investigators and research personnel are available 24 hours/day for emergencies for study subjects. Additional visits to monitor emerging symptoms will be scheduled as needed. Subjects' rights as research subjects will be reviewed at each visit.

To ensure patient comfort, but not confound study results, use of low dose lorazepam may be used for the management of affective and anxiety symptoms during the first two weeks of the study. Zolpidem and Zaleplon may be used on an as needed basis throughout the study for the management of insomnia. The use of all medications will be recorded throughout the study. As previously described, if clinical symptoms require the use of additional psychotropic agents, subjects will be terminated from the study.

A physical examination and routine laboratory monitoring at screening and endpoint will be performed. Weight, blood pressure, pulse, and EPS symptoms will be assessed at each visit. A trough lithium level will be measured at weeks 2, 3, 4, 5, and 12 (or early termination visit). When the lithium level reaches a therapeutic range, further lithium levels will not be drawn until week 12 or early termination. The lithium levels at weeks 3, 4 and 5 will only be done if the lithium level is deemed "not in the therapeutic range". These lithium levels will be only seen by an assessor not otherwise involved in the ratings in the study (who will advise a site that the dose be lowered if the lithium level is above the safe therapeutic range). To maintain the blind this assess or will chose an equal number of other patients selected at random from the placebo group to have a dose adjustment and advise the site accordingly.

At the conclusion of the trial, subjects will be offered continuation treatment with quetiapine or other medications used for the treatment of bipolar disorder. Subjects will be offered at least three additional physician visits to allow for a transition and referral for follow-up care within the clinic or community as appropriate.

1. Risks

The most commonly observed side effects associated with quetiapine in clinical trials in schizophrenia were: anxiety, somnolence, EPS, dizziness, constipation, nausea, dyspepsia, rhinitis, rash, and tachycardia. The most commonly observed side effects observed with Lithium are tremor, diarrhea, polydipsia, polyuria and nausea.

A rare risk of taking psychiatric drugs like quetiapine is the risk of developing neuroleptic malignant syndrome (NMS). NMS is a serious, potentially life-threatening disorder that includes symptoms such as: fever, tight muscles, changes in blood pressure and heart rate, as well as changes in thinking and understanding. As of early 2005, the risk of neuroleptic malignant syndrome in patients receiving quetiapine has been extremely rare.

If the subject or the study doctor decides to stop a subject's participation in the study due to increased symptoms of bipolar disorder or adverse experiences with study medication, subjects will receive appropriate follow-up treatment as determined by the study doctor. The subject's mental and physical conditions will be monitored closely by the study physician.

2. Pregnancy

Quetiapine is a Class-C teratogen (FDA Approved Labeling Text). Lithium is contraindicated in pregnancy where its use has been associated with neural tube defects. Therefore, women of childbearing potential who are not using adequate contraception and nursing mothers will be excluded from this protocol. Females who are of childbearing age:

Must have a negative pregnancy test prior to entering the study.

Must use an acceptable method of birth control (e.g., hormonal methods, intrauterine devices, barrier methods)

Must not be breast-feeding.

Agree to inform the investigator if they suspect that they are pregnant.

Agree to inform the investigator if they have stopped using the approved form of birth control.

3. Reporting of Serious Adverse Events

Investigators and other site personnel must inform the FDA, via a Medwatch form, of any unexpected and possibly Study Drug-related serious adverse events (SAEs) according to the FDA reporting requirement timelines. Reporting to the FDA is recommended regardless of whether an IND is required for the study.

All SAEs will be documented. The investigator is responsible for informing the IRB and/or the regulatory authority of the SAE as per local requirements.

4. Definitions for Adverse Event Reports

A serious adverse event is defined as one that satisfies any of the following criteria:

Results in death is immediately life-threatening requires in-patient hospitalization or prolongation of existing hospitalization results in persistent or significant disability or incapacity is a congenital abnormality or birth defect is an important medical event that may jeopardize the patient or may require medical intervention to prevent one of the outcomes listed above Serious adverse events are further explained as follows:

any death resulting from an adverse event occurring during the trial period or within 30 days after the last dose of the trial drug.

the subject must have been at an immediate risk of dying from the adverse event as it occurred. This does not include events that might have caused death if they had occurred in a more serious form (e.g., drug-induced hepatitis that resolves without hepatic failure).

any adverse event resulting in hospital admission and usually an overnight stay. Prolongs hospitalization means delayed planned or anticipated discharge date (again usually by at least one overnight stay). This does not include hospitalization for elective surgery for a condition that was present prior to trial entry and whose clinical course has not changed after exposure to the trial drug.

any adverse event resulting in impairment, damage or disruption in the subject's body function, structure or both, physical activities or quality of fife.

any adverse event resulting in a condition which requires medical or surgical intervention to prevent permanent impairment of a body function or permanent damage to a body structure of the subject. Examples of this can include procedures such as blood transfusion or catheterization. However, discontinuation of the trial drug, or routine administration of prescription medications or changes in their dosages, should not be considered as medical intervention.

if there are suspicions that exposure of either parent to the trial drug resulted in an adverse outcome in the offspring 5. Guide to Interpreting the Causality Question Time Course. Exposure to suspect drug. Has the subject actually received the suspect drug? Did the AE occur in a reasonable temporal relationship to the administration of the suspect drug?

Consistency with known drug profile. Was the AE consistent with the previous knowledge of the suspect drug (pharmacology and toxicology) or drugs of the same pharmacological class? OR could the AE be anticipated from its pharmacologic properties?

De-challenge experience. Did the AE resolve or improve on stopping or reducing the dose of the suspect drug?

No alternative cause. The AE cannot be reasonably explained by another etiology such as the underlying disease, other drugs, other host or environmental factors.

Re-challenge experience. Did the AE reoccur if the suspected drug was reintroduced after having been stopped?

Laboratory tests. A specific laboratory investigation (if performed) has confirmed the relationship.

A "reasonable possibility" could be considered to exist for an AE where one or more of these factors exist.

In contrast, there would not be a "reasonable possibility" of causality if none of the above criteria apply or where there is evidence of exposure and a reasonable time course but any de-challenge (if performed) is negative or ambiguous or there is another more likely cause of the AE.

In difficult cases, other factors could be considered such as:
is this a recognized feature of overdose of the drug?
is there a known mechanism?

Ambiguous cases should be considered as being a "reasonable possibility" of a causal relationship unless further evidence becomes available to refute this. Causal relationship in cases where the disease under study has deteriorated due to lack of effect should be classified as no reasonable possibility.

Life Threatening

"Life-threatening" means that the subject was at immediate risk of death from the AE as it occurred or it is suspected that use or continued use of the product would result in the subject's death. "Life-threatening" does not mean that had an AE occurred in a more severe form it might have caused death (e.g., hepatitis that resolved without hepatic failure).

Hospitalization

Out-patient treatment in an emergency room is not in itself a serious AE, although the reasons for it may be (e.g., bronchospasm, laryngeal edema). Hospital admissions and/or surgical operations planned before or during a study are not considered AEs if the illness or disease existed before the subject was enrolled in the study, provided that it did not deteriorate in an unexpected way during the study, 6. Important Medical Event or Medical Intervention Medical and scientific judgment should be exercised in deciding whether a case is serious in situations where important medical events may not be immediately life-threatening or result in death, hospitalization, disability or incapacity but may jeopardize the subject or may require medical intervention to prevent one or more outcomes listed in the definition of serious. These should usually be considered as serious.

Simply stopping the suspect drug does not mean that it is an important medical event; medical judgment must be used.

Examples of such events are:

Angioedema not severe enough to require intubation but requiring iv hydrocortisone treatment Hepatotoxicity caused by paracetamol (acetaminophen) overdose requiring treatment with N-acetylcysteine Intensive treatment in an emergency room or at home for allergic bronchospasm Blood dyscrasias (e.g., neutropenia or anemia requiring blood transfusion, etc.) or convulsions that do not result in hospitalization Development of drug dependency or drug abuse 7. Benefits The benefits of this study would include a thorough psychiatric evaluation; a thorough medical evaluation; the possibility that either of the study medications might alleviate suicidal symptoms or behavior, manic, depressive, and/or anxiety symptoms in subjects with bipolar disorder or Major Depressive Disorder; help and referral for additional treatment if needed; and the chance to contribute to a scientific investigation which may be of benefit to patients with bipolar disorder or Major Depressive Disorder in the future.

TABLE 2

Flow Chart of Patient Evaluations

| | | Screen | Baseline Week | Visit 3-13 | 14 | Early |
|---|---|---|---|---|---|---|
| | | −1 | 0 | 1-11 | 12 | Termination |
| ENTRY/DEMOGRAPHIC EVALUATIONS | | | | | | |
| | Informed Consent & HIPAA Form/Not-to-Suicide Contract | X | | | | |
| P | Demographic Data Inventory (DDI) | X | | | | |
| C | Psychiatric, Medical & Medication History | X | | | | |
| C | M.I.N.I. Structured Psychiatric Diagnostic Interview (MINI) | X | | | | |
| P | Past Medical Illnesses & Medical Review of Systems | X | | | | |
| P | Family Impact Scale (FIS) | | X | | X | X |
| | Patient Randomization | | X | | | |
| EFFICACY EVALUATIONS | | | | | | |
| C | Clinical Global Impressions Scale Bipolar (CGI-BP) | X | X | X | X | |
| C | Clinical Global Impressions Scale Severity (CGI-S) | X | X | | | |
| C | Violence Tracking Scale (HTS) | | X | X | X | |
| C | Hamilton Anxiety Scale (HAMA) | | X | X | X | |
| C | Young Mania Rating Scale (YMRS) | | X | X | X | |
| P | Sheehan Irritability Scale (SIS) | | X | X | X | |
| P | Rapid Ideas Scale (RISC) | | X | X | X | |
| C | Montgomery Asberg Depression Rating Scale (MADRS) | | X | X | X | |
| C | Clinician Global Improvement-21 point (CGI-21) | | | X | X | |
| P | Patient Global Improvement-21 point (PGI-21) | | | X | X | |
| P | Sheehan Disability Scale (SDS) | | X | X | X | |

TABLE 2-continued

Flow Chart of Patient Evaluations

|  | Visit | | | | |
| --- | --- | --- | --- | --- | --- |
|  | Screen | Baseline Week | 3-13 | 14 | Early |
|  | −1 | 0 | 1-11 | 12 | Termination |
| P Sheehan Suicidality Tracking Scale (S-STS) clinician & | X | X | X | X | |
| C patient rated | | | | | |
| SAFETY EVALUATIONS | | | | | |
| Serum Pregnancy Test | X | | | X | X |
| Laboratory Evaluations* (including lipids)** | X | X* | | X | X |
| EKG | X | | | X | X |
| Physical Examination | X | | | X | X |
| Body Weight and Basal Metabolic Rate (BMI) | X | X | X | X | |
| Vital Signs, Weight | X | X | X | X | |
| C Abnormal Involuntary Movement Scale (AIMS) | | X | X | X | |
| C Barnes Akathesia Scale (BARS) | | X | X | X | |
| C Simpson Angus Scale (SAS) | | X | X | X | |
| C Adverse Event Monitoring | | | X | X | |
| MISCELLANEOUS RECORDS | | | | | |
| P Mood Chart & Suicidality Chart | | X | X | X | |
| C Study Medication & Dosage Record | | X | X | X | |
| C Concomitant Medications | X | X | X | X | |
| C Patient Termination Record | | | | | X |
| Lithium Level (Blinded) at weeks 2, 3, 4, 5, and 12 | | | X | X | X |

*Baseline Laboratory Evaluation performed only if clinically significant abnormal values are noted at the Screen Evaluation and/or if deemed necessary by the site investigator. C = Clinician rated; P = Patient rated.
**Endpoint lab tests will not include Urine drug screen, TSH or T4.

EXAMPLE 3

The Treatment of Suicidality in Bipolar Disorder and Schizophrenia: A Randomized, Double-Blind, Placebo-Controlled Study of Asenapine Monotherapy The specific aim of this study is to evaluate the efficacy of asenapine monotherapy in comparison to placebo in the treatment of suicidality in ambulatory Bipolar Disorder and Schizophrenia.

Asenapine is a pharmacological agent recently approved by the US Food and Drug Administration for the treatment of bipolar disorder and schizophrenia. Asenapine is characterized by high affinity for an ensemble of serotonergic, dopaminergic, and a-adrenergic receptors but it has no appreciable affinity for muscarinic cholinergic receptors. Several trials had been conducted assessing the efficacy, safety and tolerability of asenapine in the treatment of bipolar 1 with manic and mixed symptoms including approximately 1300 subjects. In these trials asenapine showed rapid and significant advantage compared to placebo in acute use. Asenapine also showed efficacy comparable to olanzapine in extended use in these population. Asenapine was found to be superior to placebo as adjunctive therapy in bipolar patients who showed inadequate improvement on monotherapy with a mood stabilizer. Asenapine also showed a favorable profile and tolerability with long-term use (51-52). To date, it has not been specifically studied for the treatment of suicidality (suicidal ideation or suicidal behaviors).

A. Experimental Design And Methods
Methods and Procedures
Design

This is a randomized, double blind, placebo controlled, parallel-group, 12-week trial of asenapine monotherapy in outpatient subjects with mild to moderate suicidality co-morbid with a diagnosis of bipolar I or II disorder or Schizophrenia. Approximately 120 subjects will be randomized to obtain 80 subjects who complete the 12-week trial (20 completers per treatment group for each of the 2 major disorders—bipolar disorder and schizophrenia). This calculation is based on drop-out rates in a similar patient population carried out by this group of collaborators. Subjects will be randomized to asenapine or placebo in a 1:1 ratio. No concomitant psychotropic medication will be allowed throughout the study except for prn lorazepam during the first two weeks for the management of affective and anxiety symptoms, prn zolpidem or zaleplon for the management of insomnia and benztropine for the management of extrapyramidal symptoms (EPS). Throughout the study, psychiatric scales will be used to assess suicidality and psychiatric symptoms. The presence of treatment-emergent adverse events will be monitored and recorded.

Inclusion Criteria
Criteria for entering this study will include all of the following:
1. Subjects must at least age of 18 years of age and not older than 65.
2. Subjects must have bipolar I or II disorder or schizophrenia current at both the screening and the baseline visit as defined by DSM-IV TR criteria (36).
3. Subjects' bipolar or psychotic symptoms must be no more than moderate in severity, defined as a CGI-BP<4 on the Overall Bipolar Disorder dimension (37) or on the CGI-S.
4. Subjects' suicidality symptoms must be more than zero as measured by the Sheehan Suicidality Tracking Scale (S-STS) (9).
5. Subjects must not be receiving regular mood stabilizing, antidepressant, antipsychotic, or anxiolytic medication for at least one week prior to baseline. Patients receiving fluoxetine or depot antipsychotics should be off these medications for at least four weeks prior to baseline.

6. Subjects or their legally authorized representative must sign the Informed Consent Document after the nature of the trial has been fully explained.
7. If female, subjects must be: postmenopausal, surgically incapable of childbearing, or practicing medically acceptable effective method(s) of contraception (e.g., hormonal methods, barrier methods, intrauterine device) for at least one month prior to study entry and throughout the study.

Exclusion Criteria

Criteria for exclusion from this study will be any of the following:

1. Subjects who do not have bipolar disorder or schizophrenia by DSM-IV-TR criteria (36).
2. Subjects who are receiving treatment with an anti-manic or mood stabilizing medication (lithium, valproate, carbamazepine, or an antipsychotic), and in the investigators' judgment, require ongoing treatment with that medication.
3. Subjects whose manic symptoms are presently more than markedly ill (i.e., who are severely ill (defined as a mania score of >5)) on the CGI-BP mania dimension (37).
4. Subjects who have a zero score on the Sheehan Suicidality Tracking Scale (S-STS) at Screen or Baseline (9).
5. Subjects at the Screening visit who answer "yes" to the question B6 on the suicidality module of the MINI (39). This question asks: do you "feel unable to control these (suicidal) impulses"?
6. Subjects who at the Screening visit have a score of "3 or 4" on questions 2 or 3 or 4 or 8 or scores of 2 or higher on questions 1a or 5 or 6 or 7 or 9 of the Suicidality Tracking Scale (S-STS).
7. Subjects will be rescued from the study at any time after randomization if their scores on the Sheehan Suicidality Tracking Scale (S-STS) (9) cross the following severity thresholds: ≥3 on questions 3 or 4>2 on questions 1a or 5 or 6 or 7 or 9 or in addition any score on the Sheehan Suicidality Tracking Scale (S-STS) if in the judgment of the clinician the suicidality score and risk level are such that it would place the patient at unacceptable risk to continue in the study.
8. Subjects who do not sign a contract at the screening visit agreeing not to make a suicide attempt during the study.
9. Subjects who in the psychiatrist's judgment have current suicidality scores and a suicide risk level that would place them at unacceptable risk for inclusion in a 12-week placebo controlled study.
10. Subjects with clinically significant homicidal ideation (as measured by the Violence Tracking Scale (HTS).
11. Subjects with a current DSM-IV TR Axis I diagnosis of delirium, dementia, amnesia, or other cognitive disorders; a DSM-IV TR diagnosis of a substance dependence disorder within the past six months).
12. Subjects with serious general medical illnesses including hepatic, renal, respiratory, cardiovascular, endocrine, neurological, or hematological disease as determined by the clinical judgment of the clinical investigator. Subjects with hypo- or hyperthyroidism unless stabilized on thyroid replacement >3 months.
13. Subjects with a clinically significant abnormality in their pre-study physical exam, vital signs, EKG, or laboratory tests.
14. Subjects who are allergic to or who have demonstrated hypersensitivity or intolerance to either of the active study medications.
15. Women who are pregnant or nursing.
16. Subjects who have received an experimental drug or used an experimental device within 30 days.
17. Subjects who have a history of neuroleptic malignant syndrome.
18. A patient with diabetes mellitus (DM) fulfilling one of the following criteria:

Unstable DM defined as enrollment glycosylated hemoglobin (HbA1c) ≥8.5%

Admitted to hospital for treatment of DM or DM related illness within the past 12 weeks Not under physician care for DM Physician responsible for patient's DM care has not indicated that the patient's DM is controlled Physician responsible for patient's DM care has not approved the patient's participation in the study Has not been on the same dose of oral hypoglycemic drug(s) and/or diet for the 4 weeks before randomization. For thiazolidinediones (glitazones) this period should not be less than 8 weeks before randomization Taking insulin whose daily dose on one occasion in the past 4 weeks has been more than 10% above or below their mean dose in the preceding 4 weeks Note: If a patient with DM meets one of these criteria, the patient is to be excluded even if the treating physician believes that the patient is stable and can participate in the study.

Medication Dosing

The dose of each medication will be flexibly adjusted for each patient based on efficacy and tolerability. The medications will be titrated and dosed at a rate not exceeding that outlined in Table 3.

Asenapine will be administered at an initial dose of 5 mg bid and will be titrated upward to a dose considered optimal by the investigator based on the subject's clinical response and adverse events, but not to exceed 10 mg bid during the second week on medication. Subsequently, asenapine may be increased based on clinical response and tolerability to a maximum of 10 mg bid.

Asenapine and placebo will be taken on a BID schedule as outlined in Table 3. Patients in consultation with their physician may however elect to take their total daily dose at bedtime instead of the BID schedule, based on efficacy and tolerability. However this decision will not be taken lightly. Patients will be encouraged to take their medication on a BID schedule. From the second week onwards the physician may adjust the dosing up or down for each patient, based on patient tolerability and efficacy.

As needed study-prescribed (prn) use of lorazepam will be allowed for the management of affective and anxiety symptoms for the first two weeks of the study; a maximum of 2 mg per day will be allowed during the first week, and a maximum of 1 mg per day will be allowed during the second week. During the second week, the subject must be tapered off the lorazepam. For the final six weeks of the study, no lorazepam will be permitted. Zolpidem (10-20 mg/day) or zaleplon (10-20 mg/day) will be allowed for management of insomnia, and benztropine (0.5-3.0 mg/day) will be allowed for management of extrapyramidal symptoms. The latter three agents will be permitted throughout the study.

All other medications with psychotropic effects are prohibited from 1 week prior to baseline onwards.

TABLE 3

Maximum Daily Dosing Schedule in mgs and Tablet Equivalents (given bid).

| Visit | | Asenapine Tablets | Max dose mgs. | Asenapine Placebo Tablets | Dosing level |
|---|---|---|---|---|---|
| Days 1-3 | 2nd | 1 + 1 | 5 + 5 | 1 + 1 | Level 1 |
| Days 4-7 | 2nd | 1 + 2 | 5 + 10 | 1 + 2 | Level 2 |
| Week 1-2 | 3rd | 2 + 2 | 10 + 10 | 2 + 2 | Level 3 |
| Week 2-3 | 4th | 2 + 2 | 10 + 10 | 2 + 2 | Level 1-3 |
| Week 3-4 | 5th | 2 + 2 | 10 + 10 | 2 + 2 | Level 1-3 |
| Week 4-5 | 6th | 2 + 2 | 10 + 10 | 2 + 2 | Level 1-3 |
| Week 5-6 | 7th | 2 + 2 | 10 + 10 | 2 + 2 | Level 1-3 |
| Week 6-7 | 8th | 2 + 2 | 10 + 10 | 2 + 2 | Level 1-3 |
| Week 7-8 | 9th | 2 + 2 | 10 + 10 | 2 + 2 | Level 1-3 |
| Week 8-9 | 10th | 2 + 2 | 10 + 10 | 2 + 2 | Level 1-3 |
| Week 9-10 | 11th | 2 + 2 | 10 + 10 | 2 + 2 | Level 1-3 |
| Week 10-11 | 12th | 2 + 2 | 10 + 10 | 2 + 2 | Level 1-3 |
| Week 11-12 | 13th | 2 + 2 | 10 + 10 | 2 + 2 | Level 1-3 |

TABLE 4

Research Drug Supply Needed In 5 mg Asenapine tablets and Matching Placebo.
Please note these calculations are based on visits 1 week apart ± 3 days

| | Visit | Asenapine Tablets | Number Needed | Asenapine Placebo Tablets | Number Needed |
|---|---|---|---|---|---|
| Days 1-3 | 2nd | 1 + 1 | 6 | 1 + 1 | 6 |
| Days 4-7 | 2nd | 1 + 2 | 21 | 1 + 2 | 21 |
| Week 1-2 | 3rd | 2 + 2 | 40 | 2 + 2 | 40 |
| Week 2-3 | 4th | 2 + 2 | 40 | 2 + 2 | 40 |
| Week 3-4 | 5th | 2 + 2 | 40 | 2 + 2 | 40 |
| Week 4-5 | 6th | 2 + 2 | 40 | 2 + 2 | 40 |
| Week 5-6 | 7th | 2 + 2 | 40 | 2 + 2 | 40 |
| Week 6-7 | 8th | 2 + 2 | 40 | 2 + 2 | 40 |
| Week 7-8 | 9th | 2 + 2 | 40 | 2 + 2 | 40 |
| Week 8-9 | 10th | 2 + 2 | 40 | 2 + 2 | 40 |
| Week 9-10 | 11th | 2 + 2 | 40 | 2 + 2 | 40 |
| Week 10-11 | 12th | 2 + 2 | 40 | 2 + 2 | 40 |
| Week 11-12 | 13th | 2 + 2 | 40 | 2 + 2 | 40 |
| Total | | | 467 | | 467 |
| For sample of 110 patients | | | 51,370 | | 51,370 |

Identification Number Assignments

The identification number assignment procedures will be identical to those described in Example 2.

Assessments

Screening Visit(s)

The Screening Period will last a minimum of 2 to a maximum of 30 days. At the first screening visit (Visit 0), informed consent will be obtained. The MINI International Neuropsychiatric Interview 6 (MINI 6) (39), (which includes a Suicidality Assessment Module) will be performed to establish whether the patient meets DSM-IV TR (36) criteria for Bipolar disorder I or II or Schizophrenia. The Sheehan Suicidality Tracking Scale (S-STS) (9) will be independently rated by the clinician and the patient at this and each subsequent visit to assess the degree of suicidality. The computer will on which these S-STS ratings are captured at the visit will run a consistency check between the patient and clinician rated S-STS scales and provide an immediate report to the clinician, so that any differences can be re-checked in the interest of patient safety. The CGI-BP (37) and the CGI-S (38) will be performed to establish the severity of bipolar affective symptoms and schizophrenia, respectively. Subjects will keep a mood chart in between visits to help them follow their affective symptoms. The subject's manic symptoms must be no more than markedly ill (i.e., not severely ill (defined as a score ≥5 on the CGI-BP mania dimension)), and his/her illness severity must be at least moderate in severity (a CGI-S of ≥4) for him/her to be able to continue in the screening process and enter the randomized phase. The screening assessments will include a medical history, a physical exam, height, weight, vital signs, an electrocardiogram (EKG) and laboratory studies (Complete Metabolic Profile, TSH, Free T4, Hemoglobin A1c (HgA1c), Lipid profile, complete blood count (CBC) with differential+platelets, urinalysis, serum pregnancy test and urine drug screen). These assessments will be used to determine whether subjects meet the study eligibility criteria.

Baseline Visit

At baseline (Visit 1), subjects whose screening evaluations continue to meet all inclusion/exclusion criteria may enter the study and be randomized. These evaluations will include repeating the Clinical Global Impression modified for bipolar illness (CGI-BP) (37) and the Clinical Global Impressions Scale—Severity for depressive symptoms (CGI-S) (38) to ensure the subject continues to have no more than moderately severe bipolar affective symptoms and at least moderate schizophrenia. Baseline ratings will include: the Sheehan Suicidality Tracking Scale (S-STS) (9) to assess suicidality; the Violence Tracking Scale (HTS) to assess Violence; the Hamilton Anxiety Scale (HAM-A) (40) to assess anxiety symptoms; the Young Mania Rating Scale (YMRS) (41) and the Rapid Ideas Scale (RISC) to assess manic symptoms; the BPRS to assess psychotic symptoms; the Irritability Scale, (SIS), the Montgomery Asberg Depression Rating Scale (MADRS) (42) to assess depressive symptoms. Subjects will also be evaluated with the CGI-BP, and the Sheehan Disability Scale (SDS) (43-44). The Family Impact Scale (FIS) will be administered. The Abnormal Involuntary Movement Scale (AIMS) (45), Simpson Angus Scale (SAS) (46), and Barnes Akathisia Rating Scale (BARS) (47) will be administered to assess for extrapyramidal symptoms. Blood pressure, pulse, and weight, will be measured. Study medication will be dispensed by the Physician Investigator in the form of 5 mg capsules of asenapine or matching placebo. The dose range of asenapine will be 5 to 10 mg/bid.

Treatment Period

Study visits will occur every week (+3 days) through the eight weeks of treatment. It is expected that the study medication will be gradually increased to an optimal dose during the first several weeks of treatment. The following procedures will be completed at each visit.

Collect unused medication, perform study drug accountability, and record dosage of study drug used. A subject's unused study medication can be re-dispensed back to the subject.

Review mood chart and administer the Sheehan Suicidality Tracking Scale (rated by both patient and clinician independently), Clinician Global Improvement-21 point scale (CGI-I-21), Patient Global Improvement –21 point scale (PGI-21) (22) HTS, HAM-A, YMRS, SIS, RISC, BPRS, MADRS, CGI-BP, and SDS ratings.

Assess and record adverse events. An adverse event is defined as ANY treatment emergent event or as any pre-existing condition that increases in frequency or severity during the course of the study.
Perform AIMS, SAS, and BARS.
Obtain blood pressure, pulse, and weight.
Record concomitant medication use.
Adjust study medication dose (if necessary) and dispense study drug.

Final Evaluation (Week 8)

The following evaluations will be conducted at the completion of, or early withdrawal from, the 8-week treatment phase. All psychiatric evaluations and all other final study procedures (including a repeat physical exam, EKG, and laboratory studies) will be completed prior to the discontinuation of asenapine. The evaluations to be performed are:
  Collect unused study medication, perform study drug accountability, and record dosage of study drug used.
  Review mood chart and perform S-STS (patient and clinician rated), CGI-21, HTS, HAM-A, YMRS, SIS, RISC, BPRS, MADRS, CGI-BP, PGI-21, and SDS ratings.
  Repeat Family Impact Scale (FIS)
  Assess and record adverse events.
  Obtain blood pressure, pulse, weight.
  Perform physical examination, AIMS, SAS, BARS.
  Laboratory studies (Complete Metabolic Profile, Hemoglobin A1c (HgA1c), Lipid profile, CBC with/diff+platelets, Urinalysis, serum pregnancy test).
  Repeat EKG.
  Record concomitant medication use.
  Adjust study medication dose (if necessary) and prescribe drug (if subject has responded and chooses to continue on study medication), or dispense study medication for taper or discontinuation (if subject has not responded or if subject chooses to discontinue study medication for any reason).
Early Termination Visit:
  In the event of an early termination visit, the usual scales for that patient's weekly visit will be completed. If they terminate at week 4, then the week 4 visit scales are completed.
  In addition to the above, the following termination data will be collected:
  Physical examination, EKG, laboratory tests (complete metabolic profile, Hemoglobin A1e (HgA1c), lipid profile, CBC with/diff+platelets, urinalysis, serum pregnancy test), Family Impact Scale and Termination Record Form.
Termination Criteria:
  Subjects will be terminated from the protocol if:
  At any time after randomization if their scores on the Sheehan Suicidality Tracking Scale (S-STS) (9) cross the following severity thresholds: >3 on questions 4 or 5 or 6 or 10 or ≥2 on questions 3a or 7 or 8 or 9 or 11 or in addition any score on the Sheehan Suicidality Tracking Scale (S-STS) if in the judgment of the clinician the suicidality score and risk level are such that it would place the patient at unacceptable risk to continue in the study.
  The CGI-BP or CGI-I rating for change is "very much worse," the YMRS is >21, or the MADRS is >40.
  The subject manifests signs of, or, shows evidence of clinically significant suicidality or homicidal ideation that would place them at unacceptable risk to continue in the study. Subjects who are suicidal or homicidal or who require hospitalization will be terminated from the protocol to allow for unencumbered medication changes.
  In the absence of the above, subjects will be terminated at the treating psychiatrist's discretion in response to symptoms of sufficient severity that medication changes are warranted as described above.
Subjects may withdraw or be withdrawn from the protocol at any time, for any reason, and such terminations will be documented. All subjects who are terminated from the protocol will receive at least:
  3 additional physician visits.
  Referrals for other appropriate sources of continued care.
  The option to receive open-label effective medications for bipolar disorder as clinically indicated.
Data Collection and Analysis
Electronic Data Capture All the standardized data captured in this study, except for the history, the laboratory results, the EKG, the physical exam form and the informed and HIPAA forms will be directly recorded at the time of the visit into an electronic data capture database program on a Tablet PC or a Laptop PC, instead of first recording it on to a paper source document and later copying this information into a computer after the visit is completed. All the data capture forms (including scales, structured interviews, medication monitoring, adverse events concomitant medication tracking) for this study will be in the Tablet PCs. The appearance and layout of these forms in the Tablet PC mirrors those traditionally used in paper case report forms. Both the physician and patient will enter their data directly into the Tablet PC at the time of the visit. The database file in the Tablet PC is the source document for this study.

Direct entry electronic data capture (EDC) at the time of the visit, eliminates the need for later data entry by manual key punching into a computer from paper source documents, which is associated with transcription errors, personnel costs and delays. EDC eliminates the problem of missing values and double entries, since the software program in the Tablet PC will not save data from scales, unless all questions are answered. EDC is also programmed to make it impossible to give two responses to one question, where only one response is required.

At the end of each visit, the completed forms can be printed out via the PC wireless card in the Tablet PC and then filed in ring binders for later audit as paper case report forms. The data in the Tablet PC can be sent electronically to a sponsor daily or as often as required. This permits the sponsor to monitor patient enrollment and to monitor adverse events and other data of interest as the study progresses. It substantially reduces the need for site monitors, since monitoring can now be done centrally in-house by the sponsor. At the end of the study, or sooner if needed, the data can be exported directly from the Tablet PC in a form that can be read in Excel or in any statistics package on any other computer.
Data Analysis Plan The primary comparison of interest is asenapine versus placebo using the Sheehan Suicidality Tracking Scale (S-STS)—both clinician rated and patient rated versions. Secondary comparisons include asenapine versus placebo for the following measures: the HTS, the HAM-A total score, the psychic and somatic factor scores of the HAM-A, the YMRS total score, the SIS total score, the RISC total score, the BPRS, the MADRS total score, the CGI-21, the PGI-21, the CGI-BP, the FIS, and the work, social, and family disability (SDS) scores. Additional comparisons of interest include the use of adjunctive anxiolytic and hypnotic medication, adherence to study medication, frequency and severity of side effects, and reasons for early termination.

The comparability of treatment groups will be assessed at baseline using parametric statistics for continuous variables (e.g., age) and chi-square or appropriate non parametric statistic, with a continuity correction where indicated, for categorical variables (e.g. gender. previous use of medications).

Efficacy analyses will be based on the intent-to-treat (ITT) population. For the purpose of the study, the ITT population will be defined as all patients who are randomly assigned to treatment, receive at least one dose of study medication, and have at least one post-baseline assessment. For these analyses, missing data will be carried forwards using the last-observation-carried forwards (LOCF) technique. Because of the relatively small size of the sample (30 completed per treatment group) data will be pooled for the three centers. Analyses will also be carried out on the observed cases dataset although these analyses will be considered secondary and supplemental to the primary LOCF analyses. Repeated measures analysis of covariance (ANCOVA) with baseline scores as a covariate will be the main method for assessing the efficacy of asenapine versus placebo for the primary efficacy variable, improvement on the Sheehan Suicidality Tracking Scale (S-STS)—both clinician rated and patient rated versions. Repeated measures analysis of covariance (ANCOVA), with baseline score as a covariate, will be used to compare the efficacy of asenapine and placebo for the secondary measures HTS, HAM-A, YMRS, SIS, RISC, MADRS, the CGI-21, the PGI-21, CGI-BP, FIS and SDS scales. Non-parametric statistics (e.g. chi-square with a correction for continuity as indicated) will be employed to examine potential differences in the use of adjunctive anxiolytics and hypnotics, adherence to study medication, and reasons for early termination. All statistical tests will be two-tailed and carried out at an alpha level of 0.05.

An additional analysis of the primary efficacy measures will be conducted using the ETRANK statistical method developed by Richard Entsuah (48). This analysis is included to provide a potentially more sensitive and accurate alternative to the LOCF technique for imputing missing data. The method, is a modification and extension of Gould's (49) ranking approach. It accounts for treatment related (informative censoring) dropouts by using a nonparametric (randomization) method to analyze incomplete repeated-measures data. With this technique, the observed full data set is used and the pattern, time, reasons and proportion of study withdrawals are incorporated in the statistical method. As Entsuah observes, parametric missing data methods such as Mixed Effects models, Hierarchical Linear Models (HLM), and Imputations methods need to be validated using the assumptions of Missing at Random (MAR) and Missing Completely at Random (MCAR) (50). In contrast, the ETRANK principle is not based on these assumptions. All available data are included, regardless of the reason for early termination from the study, and withdrawals due to adverse events or lack of efficacy are assigned weights, which reflect discontinuation due to improvement, deterioration, and time. Patients who have only baseline measurements who discontinue the study may be included in the computations.

For all numeric variables, assumptions of normality and homogeneity of variance will be assessed by examining normal probability and residual plots. If assumptions of normality and homogeneity of variance are not met, additional analyses will be performed in order to assess the robustness of the conclusions from the primary analysis. This will include investigation of appropriate transformations of the efficacy variable and if an appropriate transformation cannot be identified, non-parametric methods will be used (i.e. the Wilcoxan Rank Sum test).

Safety analyses will be based on all patients receiving medication at baseline (the intent to treat population). Treatment emergent differences in the AIMS, BARS and SAS total scores will be analyzed using one-way analysis of variance at each study week. One-way analysis of variance will also be used to examine weekly differences in vital signs (blood pressure and pulse). A listing of the final dose achieved by each patient and its relationship with rating scales will be provided. In addition, a listing of all adverse experiences, abnormal clinical values, abnormal vital signs (blood pressure and pulse) and termination data will be supplied.

In addition, all efficacy measures over the course of the study will be presented and summarized in graphs and tables. Continuous data will be summarized by means, standard deviations, medians, maximum, minimum and number of patients. Categorical data will be summarized by counts and percentages.

The data for a final endpoint visit will not be included in the efficacy analysis if the date of that visit is ≥12 days from the previous visit at which medication was dispensed. The reason for this is to exclude patients from the endpoint efficacy analyses if they have been off their study medication or out of study medication for at least 2 days at endpoint. All safety data on these patients will be included in the safety analyses. In addition, endpoint efficacy data will be excluded on any patient if their study exit is associated with a protocol violation that could influence efficacy (e.g., taking a benzodiazepine or lithium, or not taking study medication for an extended period).

Power Analysis

There are no published studies on suicidality on which to base a power calculation. The sample size of 20 completed patients per treatment arm per disorder studied was chosen because it is typically the minimum sample size needed to provide normally distributed data on most of the scales used as outcome measures. This will allow analysis of the data using parametric analyses, thereby increasing the sensitivity of our analyses. Such a sample size will provide data that will permit a power analysis to be run on the results and provide the ability to calculate the sample size that would be needed to statistically separate active drug from placebo should there be a difference that falls is not statistically significant at p<0.05. This would be helpful in planning future larger studies on suicidality.

Using a simple t-test on change from baseline in standard bipolar disorder studies to estimate a lower bound on power, the discernible effect sizes are:

| Number of patients per arm | | | |
| --- | --- | --- | --- |
| 30 | 25 | 20 | |
| 0.74 | 0.81 | 0.91 | 80% power, statistical significance = 0.05 |

Using a repeated measures analysis, we can expect higher power and to be able to discern smaller effect sizes.

Data Monitoring

The study data will be monitored by the coordinating site at the University of South Florida College of Medicine. All sites will provide the coordinating site with enrollment logs monthly generated from the study software computer program. This will certify work done and will be the basis for the payments monthly to each site. The computer databases of completed work will also be sent to the coordinating site monthly for data monitoring purposes.

A study start-up teleconference will be held before the study begins, at intervals during the study, and as often as deemed necessary by the coordinating site and at the study close-out. Communication by telephone, fax, e-mail and mail may be used as needed to supplement the teleconferences. The purpose of these teleconferences is to verify 1) adherence to the protocol and 2) the completeness and accuracy of the direct data entry and any additional case report forms, informed consent documents and the clinical stock record. Adequate time for these teleconferences should be allocated by the investigators at each site. Patients' source documents and PC databases will be available for review.

A source document is defined as the place where the original information is first recorded. Most of the data will be directly entered at the time of the visit into a computer database program designed specifically for the study. The database file in the PC will therefore be the source document for almost all of the data in the study. A paper case report form may be a source document if the original information is first recorded there. Unnecessary duplication or re-transcription of data will be avoided where possible so as to insure accuracy and avoid transcription errors. Interim checks on the progress of the study will be made by telephone and by sharing of enrollment logs.

Data Safety Monitoring Board

Because of the unique safety concerns about conducting a study of this kind, a data safety monitoring board will be set up to monitor safety concerns, particularly relating to suicidality. Because the data in this study is being collected in real time the data will be relayed to the chairperson of the data safety monitoring board weekly for review with a summary report of the Sheehan Suicidality Tracking Scale (S-STS) results on individual patients. The data safety monitoring board will be provided a copy of the software and export engine so that they can independently assess any information they need to know to ensure every effort is being made to properly provide for patient safety.

Data Storage and Confidentiality

Back-ups of the data in the computer database file will be made daily and stored at each site. Strict measures will be taken at each site to ensure that tablet PCs or laptops used for the study and the back-up data records are kept under lock and key when not in use to ensure confidentiality. All data will be verified for accuracy before being transferred into a statistical package for data analysis.

B. Human Subjects

Subjects will include 120 randomized patients to yield 80 completed outpatients with lifetime bipolar I disorder, bipolar II disorder, or Schizophrenia by DSM-IV-TR criteria (25), who have more than zero suicidality at the study screening and baseline visits (but whose suicidality is not at a level of severity that will place them at unacceptable risk during the study). Subjects must not be on other psychotropic medications except pm use of lorazepam (for the first 2 weeks of the study), zolpidem, or zaleplon. Subjects must sign a contract not to suicide during the study. Subjects must be ≥18 years of age, be able to provide informed consent, and if female, be postmenopausal, surgically incapable of childbearing, or practicing medically acceptable method(s) of contraception (e.g., hormonal methods, intrauterine device, barrier methods) for at least 1 month prior to study entry and throughout the study. Exclusion criteria include subjects with a current DSM-IV Axis 1 diagnosis of delirium, dementia, amnesia, or other cognitive disorders, or a substance dependence disorder within the past six months; those with clinically significant suicidal or homicidal ideation; those with serious or unstable general medical illnesses; those who are allergic to or who have demonstrated hypersensitivity to asenapine; and females who are pregnant or nursing. Subjects will be recruited from local physician referrals and by advertising.

C. Safety And Subject Protection

A number of measures are included to ensure subject safety in this protocol. The informed consent process allows the subjects to read the informed consent at their leisure. It is then reviewed with the subject by the study coordinator or investigator. The investigator will be available to answer all questions a patient may have about the study and their participation. Only then will the subject sign and date the informed consent document and the HIPAA document. Investigators and research personnel are available 24 hours/day for emergencies for study subjects. Additional visits to monitor emerging symptoms will be scheduled as needed. Subjects' rights as research subjects will be reviewed at each visit.

To ensure patient comfort, but not confound study results, use of low dose lorazepam may be used for the management of affective and anxiety symptoms during the first two weeks of the study. Zolpidem and Zaleplon may be used on an as needed basis throughout the study for the management of insomnia. The use of all medications will be recorded throughout the study. As previously described, if clinical symptoms require the use of additional psychotropic agents, subjects will be terminated from the study.

A physical examination and routine laboratory monitoring at screening and endpoint will be performed. Weight, blood pressure, pulse, and EPS symptoms will be assessed at each visit.

At the conclusion of the trial, subjects will be offered continuation treatment with asenapine or other medications used for the treatment of bipolar disorder or schizophrenia. The asenapine will not be provided free of charge by Schering Plough. Subjects will be offered at least three additional physician visits to allow for a transition and referral for follow-up care within the clinic or community as appropriate.

1. Risks

The most commonly observed side effects associated with asenapine in clinical trials in schizophrenia were: anxiety, somnolence, EPS, dizziness, constipation, nausea, dyspepsia, rhinitis, rash, and tachycardia.

A rare risk of taking psychiatric drugs like asenapine is the risk of developing neuroleptic malignant syndrome (NMS). NMS is a serious, potentially life-threatening disorder that includes symptoms such as: fever, tight muscles, changes in blood pressure and heart rate, as well as changes in thinking and understanding. The risk of neuroleptic malignant syndrome in patients receiving asenapine is extremely rare.

If the subject or the study doctor decides to stop a subject's participation in the study due to increased symptoms of bipolar disorder or adverse experiences with study medication, subjects will receive appropriate follow-up treatment as determined by the study doctor. The subject's mental and physical conditions will be monitored closely by the study physician.

2. Pregnancy

Asenapine is a Class-C teratogen (FDA Approved Labeling Text). Therefore, women of childbearing potential who are not using adequate contraception and nursing mothers will be excluded from this protocol. Females who are of childbearing age:

Must have a negative pregnancy test prior to entering the study.

Must use an acceptable method of birth control (e.g., hormonal methods, intrauterine devices, barrier methods)

Must not be breast-feeding.

Agree to inform the investigator if they suspect that they are pregnant.

Agree to inform the investigator if they have stopped using the approved form of birth control.

3. Reporting of Serious Adverse Events

Investigators and other site personnel must inform the FDA, via a Medwatch form, of any unexpected and possibly Study Drug-related serious adverse events (SAEs) according to the FDA reporting requirement timelines. The investigator must also inform appropriate Schering Plough representatives of any SAE that occurs in the course of the study within one day (i.e., immediately but no later than the end of the next business day) of when he or she becomes aware of it. The investigator must also report follow-up information on SAEs within one day. A copy off the Medwatch report must be faxed Schering Plough at the time at the event is reported to the FDA. Reporting to the FDA is recommended regardless of whether an IND is required for the study.

> Additionally, the Investigator shall provide Schering Plough with a report of all other SAEs that did not qualify for expedited reporting to the FDA (e.g., considered to be expected and/or not related) on at least a quarterly basis in order for Schering Plough to meet its regulatory reporting obligations.
>
> If the Study is blinded, the Institution shall provide Schering Plough with the code break information with the initial SAE report or a copy of the randomization schedule at the start of the Study, so that Schering Plough may un-blind SAE reports to the extent necessary to meet global regulatory reporting requirements.

A complete written SAE report must be sent with a cover page indicating the following:

Drug name (Saphris); this is an Investigator Sponsored Study (ISS)

Research (Protocol) and Schering Plough Tracking Number (XX_____)

Principal investigator's IND number assigned by the FDA (if applicable)

Principal investigator's full name and address

Unblinding information (if applicable)

Send by way of fax to Saphris ISS Safety Representative (XXX) XXX-XXXX.

> If a non-serious AE becomes serious, this and other relevant follow-up information must also be provided to Schering Plough and the FDA within one day as described above. All SAEs have to be reported to Schering Plough, whether or not considered causally related to the investigational product. All SAEs will be documented. The investigator is responsible for informing the IRB and/or the regulatory authority of the SAE as per local requirements.

4. Definitions for Adverse Event Reports

A serious adverse event is defined as one that satisfies any of the following criteria:

> Results in death
> is immediately life-threatening
> requires in-patient hospitalization or prolongation of existing hospitalization
> results in persistent or significant disability or incapacity
> is a congenital abnormality or birth defect
> is an important medical event that may jeopardize the patient or may require medical intervention to prevent one of the outcomes listed above
> Serious adverse events are further explained as follows:
> any death resulting from an adverse event occurring during the trial period or within 30 days after the last dose of the trial drug.
> the subject must have been at an immediate risk of dying from the adverse event as it occurred. This does not include events that might have caused death if they had occurred in a more serious form (e.g., drug-induced hepatitis that resolves without hepatic failure).
> any adverse event resulting in hospital admission and usually an overnight stay. Prolongs hospitalization means delayed planned or anticipated discharge date (again usually by at least one overnight stay). This does not include hospitalization for elective surgery for a condition that was present prior to trial entry and whose clinical course has not changed after exposure to the trial drug.
> any adverse event resulting in impairment, damage or disruption in the subject's body function, structure or both, physical activities or quality of fife.
> any adverse event resulting in a condition which requires medical or surgical intervention to prevent permanent impairment of a body function or permanent damage to a body structure of the subject. Examples of this can include procedures such as blood transfusion or catheterization. However, discontinuation of the trial drug, or routine administration of prescription medications or changes in their dosages, should not be considered as medical intervention.
> if there are suspicions that exposure of either parent to the trial drug resulted in an adverse outcome in the offspring 5. Guide to Interpreting the Causality Question > Time Course. Exposure to suspect drug. Has the subject actually received the suspect drug? Did the AE occur in a reasonable temporal relationship to the administration of the suspect drug?
> Consistency with known drug profile. Was the AE consistent with the previous knowledge of the suspect drug (pharmacology and toxicology) or drugs of the same pharmacological class? OR could the AE be anticipated from its pharmacologic properties?
> De-challenge experience. Did the AE resolve or improve on stopping or reducing the dose of the suspect drug?
> No alternative cause. The AE cannot be reasonably explained by another etiology such as the underlying disease, other drugs, other host or environmental factors.
> Re-challenge experience. Did the AE reoccur if the suspected drug was reintroduced after having been stopped? Schering Plough would not normally recommend or support a re-challenge.
> Laboratory tests. A specific laboratory investigation (if performed) has confirmed the relationship.

A "reasonable possibility" could be considered to exist for an AE where one or more of these factors exist.

In contrast, there would not be a "reasonable possibility" of causality if none of the above criteria apply or where there is evidence of exposure and a reasonable time course but any de-challenge (if performed) is negative or ambiguous or there is another more likely cause of the AE.

In difficult cases, other factors could be considered such as:

is this a recognized feature of overdose of the drug?

is there a known mechanism?

Ambiguous cases should be considered as being a "reasonable possibility" of a causal relationship unless further evidence becomes available to refute this. Causal relationship in cases where the disease under study has deteriorated due to lack of effect should be classified as no reasonable possibility.

Life Threatening

"Life-threatening" means that the subject was at immediate risk of death from the AE as it occurred or it is suspected that use or continued use of the product would result in the subject's death. "Life-threatening" does not mean that had an AE occurred in a more severe form it might have caused death (e.g., hepatitis that resolved without hepatic failure).

Hospitalization

Out-patient treatment in an emergency room is not in itself a serious AE, although the reasons for it may be (e.g., bronchospasm, laryngeal edema). Hospital admissions and/or surgical operations planned before or during a study are not considered AEs if the illness or disease existed before the subject was enrolled in the study, provided that it did not deteriorate in an unexpected way during the study.

6. Important Medical Event or Medical Intervention

Medical and scientific judgment should be exercised in deciding whether a case is serious in situations where important medical events may not be immediately life-threatening or result in death, hospitalization, disability or incapacity but may jeopardize the subject or may require medical intervention to prevent one or more outcomes listed in the definition of serious. These should usually be considered as serious.

Simply stopping the suspect drug does not mean that it is an important medical event; medical judgment must be used.

Examples of such events are:
Angioedema not severe enough to require intubation but requiring iv hydrocortisone treatment
Hepatotoxicity caused by paracetamol (acetaminophen) overdose requiring treatment with N-acetylcysteine
Intensive treatment in an emergency room or at home for allergic bronchospasm
Blood dyscrasias (e.g., neutropenia or anemia requiring blood transfusion, etc.) or convulsions that do not result in hospitalization
Development of drug dependency or drug abuse 7. Benefits The benefits of this study would include a thorough psychiatric evaluation; a thorough medical evaluation; the possibility that either of the study medications might alleviate suicidal symptoms or behavior, manic, depressive, and/or anxiety symptoms in subjects with bipolar disorder or schizophrenia; help and referral for additional treatment if needed; and the chance to contribute to a scientific investigation which may be of benefit to patients with bipolar disorder or Major Depressive Disorder in the future.

TABLE 5

Flow Chart of Patient Evaluations

| | | Screen | Baseline Week | 3-13 | 14 | Early |
|---|---|---|---|---|---|---|
| | | −1 | 0 | 1-11 | 12 | Termination |
| ENTRY/DEMOGRAPHIC EVALUATIONS | | | | | | |
| | Informed Consent & HIPAA Form/Not-to-Suicide Contract | X | | | | |
| P | Demographic Data Inventory (DDI) | X | | | | |
| C | Psychiatric, Medical & Medication History | X | | | | |
| C | M.I.N.I. Structured Psychiatric Diagnostic Interview (MINI) | X | | | | |
| P | Past Medical Illnesses & Medical Review of Systems | X | | | | |
| P | Family Impact Scale (FIS) | | X | | X | X |
| | Patient Randomization | | X | | | |
| EFFICACY EVALUATIONS | | | | | | |
| C | Clinical Global Impressions Scale Bipolar (CGI-BP) | X | X | X | X | |
| C | Clinical Global Impressions Scale Severity (CGI-S) | X | X | | | |
| C | Violence Tracking Scale (HTS) | | X | X | X | |
| C | Hamilton Anxiety Scale (HAMA) | | X | X | X | |
| C | Young Mania Rating Scale (YMRS) | | X | X | X | |
| P | Sheehan Irritability Scale (SIS) | | X | X | X | |
| P | Rapid Ideas Scale (RISC) | | X | X | X | |
| C | Montgomery Asberg Depression Rating Scale (MADRS) | | X | X | X | |
| C | Brief Psychiatric Rating Scale (BPRS) | | X | X | X | |
| C | Clinician Global Improvement-21 point (CGI-21) | | | X | X | |
| P | Patient Global Improvement-21 point (PGI-21) | | | X | X | |
| P | Sheehan Disability Scale (SDS) | | X | X | X | |
| P C | Sheehan Suicidality Tracking Scale (S-STS) clinician & patient rated | X | X | X | X | |
| SAFETY EVALUATIONS | | | | | | |
| | Serum Pregnancy Test | X | | | X | X |
| | Laboratory Evaluations* (including lipids)** | X | X* | | X | X |
| | EKG | X | | | X | X |
| | Physical Examination | X | | | X | X |
| | Body Weight and Basal Metabolic Rate (BMI) | X | X | X | X | |
| | Vital Signs, Weight | X | X | X | X | |
| C | Abnormal Involuntary Movement Scale (AIMS) | | X | X | X | |
| C | Barnes Akathisia Scale (BARS) | | X | X | X | |
| C | Simpson Angus Scale (SAS) | | X | X | X | |
| C | Adverse Event Monitoring | | | X | X | |
| MISCELLANEOUS RECORDS | | | | | | |
| P | Mood Chart & Suicidality Chart | | X | X | X | |
| C | Study Medication & Dosage Record | | | X | X | |
| C | Concomitant Medications | | X | X | X | X |

TABLE 5-continued

Flow Chart of Patient Evaluations

|   |   | Visit | | | | |
|---|---|---|---|---|---|---|
|   |   | Screen | Baseline Week | 3-13 | 14 | Early |
|   |   | −1 | 0 | 1-11 | 12 | Termination |
| C | Patient Termination Record |   |   |   |   | X |
|   | Lithium Level (Blinded) at weeks 2, 3, 4, 5, and 12 |   | X | X | X |   |

*Baseline Laboratory Evaluation performed only if clinically significant abnormal values are noted at the Screen Evaluation and/or if deemed necessary by the site investigator.
C = Clinician rated;
P = Patient rated.
**Endpoint lab tests will not include Urine drug screen, TSH or T4.

EXAMPLE 4

The Treatment of Suicidality in Bipolar Disorder and Major Depressive Disorder: A Randomized, Double-Blind, Placebo-Controlled Study of Aripiprazole Monotherapy The specific aim of this study is to evaluate the efficacy of aripiprazole monotherapy in comparison to placebo in the treatment of suicidality in ambulatory Bipolar Disorder and Major Depressive Disorder.

In a randomized, double-blind, placebo-controlled trial in 542 outpatients of quetiapine in the treatment of bipolar I and II depression, Calabrese et al. (Boulder 1 study) (23) reported in a secondary post-hoc analysis that both 300 mg/day and 600 mg/day were more effective than placebo in reducing suicidal ideation by week 8 (endpoint) (p<0.001). The reduction in suicidal ideation on quetiapine was approximately twice that of placebo as measured by item 10 on the Montgomery Asberg Depression Rating Scale (MADRS). The mean percent reduction in suicidal thoughts was she approximately 60% on quetiapine compared to approximately 30% on placebo.

Houston et al. (34) reported that the addition of olanzapine versus placebo to lithium or divalproex monotherapy significantly reduced suicidal ideation, as measured by the Hamilton Depression Scale –item 3 scores, she in 58 bipolar I mixed state patients.

Ciaparelli et al. (35) reported that quetiapine was effective in lowering suicidality in treatment resistant psychotic bipolar patients over 24 months of observation, suggesting that the anti-suicide properties of clozapine seen in schizophrenia and in schizoaffective disorder may also be seen in bipolar disorder.

Quetiapine has also been shown to be superior to placebo when used in combination with lithium or divalproex in hospitalized adult patients with acute mania (21) and when used in combination with divalproex in adolescent patients with acute bipolar I mania (22).

Quetiapine has been shown to be superior to placebo in reducing depressive and anxiety symptoms in patients with a bipolar 1 or II disorder and an acute bipolar depression (23, 24). It has also been shown to reduce depressive symptoms more than haloperidol in schizophrenic patients with persistent ongoing symptoms (25). Its anti-manic properties have been hypothesized to be due in part to antagonism at dopamine (DA) $D_2$ receptors and its antidepressant and anxiolytic properties may be due to its serotonergic (5HT) properties (26).

Asenapine is a pharmacological agent recently approved by the US Food and Drug Administration for the treatment of bipolar disorder and schizophrenia. Asenapine is characterized by high affinity for an ensemble of serotonergic, dopaminergic, and a-adrenergic receptors but it has no appreciable affinity for muscarinic cholinergic receptors. Several trials had been conducted assessing the efficacy, safety and tolerability of asenapine in the treatment of bipolar I with manic and mixed symptoms including approximately 1300 subjects. In these trials asenapine showed rapid and significant advantage compared to placebo in acute use. Asenapine also showed efficacy comparable to olanzapine in extended use in these population. Asenapine was found to be superior to placebo as adjunctive therapy in bipolar patients who showed inadequate improvement on monotherapy with a mood stabilizer. Asenapine also showed a favorable profile and tolerability with long-term use (51-52). To date, it has not been specifically studied for the treatment of suicidality (suicidal ideation or suicidal behaviors).

Aripiprazole is a pharmacological agent approved by the US Food and Drug Administration for the treatment of manic or mixed episodes associated with bipolar I disorder, maintenance treatment of bipolar I disorder and adjunctive treatment of major depressive disorder (MDD) and schizophrenia. The clinical efficacy of aripiprazole may be mediated through a combination of partial agonist activity at D2 and 5-HT1a receptors and antagonist activity at 5HT2a receptors. Additional actions at receptors other than the D2, 5HT1a and 5HT2a receptors may explain some of the other clinical effects.

At least 4 positive, 3 week trials were conducted assessing the efficacy, safety and tolerability of aripiprazole in the treatment of bipolar I disorder with manic and mixed symptoms with approximately 1450 subjects (n=268; n=248; n=480; n=485). In these trials aripiprazole showed rapid and significant advantage compared to placebo in acute use. Aripiprazole was found to be superior to placebo as adjunctive therapy (with either lithium or valproate) in bipolar I patients, manic or mixed state who showed inadequate improvement on monotherapy with a mood stabilizer. Aripiprazole was found in two, 6 week studies, to be superior to placebo as adjunctive therapy (with either paroxetine controlled release, venlafaxine extended release, fluoxetine, escitalopram or sertraline) in patients with major depressive disorder, who showed an inadequate response on monotherapy with prior antidepressant therapy. Aripiprazole also showed a favorable profile and tolerability with long-term use up to 6 months. To date, aripiprazole has not been specifically studied for the treatment of suicidality (suicidal ideation or suicidal behaviors).

A. Experimental Design and Methods
Methods and Procedures
Design

This is a randomized, double blind, placebo controlled, parallel-group, 12-week trial of aripiprazole monotherapy in outpatient subjects with mild to moderate suicidality co-morbid with a diagnosis of bipolar I or II disorder or Major Depressive Disorder. Approximately 120 subjects will be randomized to obtain 80 subjects who complete the 12-week trial (20 completers per treatment group for each of the 2 major disorders—bipolar disorder and Major Depressive Disorder). This calculation is based on drop-out rates in a similar patient population carried out by this group of collaborators. Subjects will be randomized to aripiprazole or placebo in a 1:1 ratio. No concomitant psychotropic medication will be allowed throughout the study except for prn lorazepam during the first two weeks for the management of affective and anxiety symptoms, pm zolpidem or zaleplon for the management of insomnia and benztropine for the management of extrapyramidal symptoms (EPS). Throughout the study, psychiatric scales will be used to assess suicidality and psychiatric symptoms. The presence of treatment-emergent adverse events will be monitored and recorded.

Inclusion Criteria

Criteria for entering this study will include all of the following:

1. Subjects must at least age of 25 years of age and not older than 65.
2. Subjects must have bipolar I or II disorder or Major Depressive Disorder current at both the screening and the baseline visit as defined by DSM-IV TR criteria (36).
3. Subjects' bipolar or psychotic symptoms must be no more than moderate in severity, defined as a CGI-BP<4 on the Overall Bipolar Disorder dimension (37) or on the CGI-S.
4. Subjects' suicidality symptoms must be more than zero as measured by the Sheehan Suicidality Tracking Scale (S-STS) (9).
5. Subjects must not be receiving regular mood stabilizing, antidepressant, antipsychotic, or anxiolytic medication for at least one week prior to baseline. Patients receiving fluoxetine or depot antipsychotics should be off these medications for at least four weeks prior to baseline.
6. Subjects or their legally authorized representative must sign the Informed Consent Document after the nature of the trial has been fully explained.
7. If female, subjects must be: postmenopausal, surgically incapable of childbearing, or practicing medically acceptable effective method(s) of contraception (e.g., hormonal methods, barrier methods, intrauterine device) for at least one month prior to study entry and throughout the study.

Exclusion Criteria

Criteria for exclusion from this study will be any of the following:

1. Subjects who do not have Bipolar Disorder I or II or NOS or Major Depressive
   Disorder by DSM-IV-TR criteria (36).
2. Subjects who are receiving treatment with an anti-manic or mood stabilizing medication (lithium, valproate, carbamazepine, or an antipsychotic), and in the investigators' judgment, require ongoing treatment with that medication.
3. Subjects whose manic symptoms are presently more than markedly ill (i.e., who are severely ill (defined as a mania score of >5)) on the CGI-BP mania dimension (37).
4. Subjects who have a zero score on the Sheehan Suicidality Tracking Scale (S-STS) at Screen or Baseline (9).
5. Subjects at the Screening visit who answer "yes" to the question B6 on the suicidality module of the MINI (39). This question asks: do you "feel unable to control these (suicidal) impulses"?
6. Subjects who at the Screening visit have a score of "3 or 4" on questions 2 or 3 or 4 or 8 or scores of 2 or higher on questions 1a or 5 or 6 or 7 or 9 of the Suicidality Tracking Scale (S-STS).
7. Subjects will be rescued from the study at any time after randomization if their scores on the Sheehan Suicidality Tracking Scale (S-STS) (9) cross the following severity thresholds: ≥3 on questions 3 or 4 or >2 on questions 1a or 5 or 6 or 7 or 9 or in addition any score on the Sheehan Suicidality Tracking Scale (S-STS) if in the judgment of the clinician the suicidality score and risk level are such that it would place the patient at unacceptable risk to continue in the study.
8. Subjects who do not sign a contract at the screening visit agreeing not to make a suicide attempt during the study.
9. Subjects who in the psychiatrist's judgment have current suicidality scores and a suicide risk level that would place them at unacceptable risk for inclusion in a 12-week placebo controlled study.
10. Subjects with clinically significant homicidal ideation (as measured by the Violence Tracking Scale (HTS).
11. Subjects with a current DSM-IV TR Axis I diagnosis of delirium, dementia, amnesia, or other cognitive disorders; a DSM-IV TR diagnosis of a substance dependence disorder within the past six months).
12. Subjects with serious general medical illnesses including hepatic, renal, respiratory, cardiovascular, endocrine, neurological, or hematological disease as determined by the clinical judgment of the clinical investigator. Subjects with hypo- or hyperthyroidism unless stabilized on thyroid replacement >3 months.
13. Subjects with a clinically significant abnormality in their pre-study physical exam, vital signs, EKG, or laboratory tests.
14. Subjects who are allergic to or who have demonstrated hypersensitivity or intolerance to either of the active study medications.
15. Women who are pregnant or nursing.
16. Subjects who have received an experimental drug or used an experimental device within 30 days.
17. Subjects who have a history of neuroleptic malignant syndrome.
18. A patient with diabetes mellitus (DM) fulfilling one of the following criteria:
    Unstable DM defined as enrollment glycosylated hemoglobin (HbA1c) ≥8.5%
    Admitted to hospital for treatment of DM or DM related illness within the past 12 weeks
    Not under physician care for DM
    Physician responsible for patient's DM care has not indicated that the patient's DM is controlled
    Physician responsible for patient's DM care has not approved the patient's participation in the study
    Has not been on the same dose of oral hypoglycemic drug(s) and/or diet for the 4 weeks before randomization. For thiazolidinediones (glitazones) this period should not be less than 8 weeks before randomization
    Taking insulin whose daily dose on one occasion in the past 4 weeks has been more than 10% above or below their mean dose in the preceding 4 weeks Note: If a patient with DM meets one of these criteria, the patient is to be excluded even if the treating physician believes that the patient is stable and can participate in the study.

Medication Dosing

The dose of each medication will be flexibly adjusted for each patient based on efficacy and tolerability. The medications will be titrated and dosed at a rate not exceeding that outlined in Table 6.

Aripiprazole will be administered at an initial dose of 5 mg qd and will be titrated upward to a dose considered optimal by the investigator based on the subject's clinical response and adverse events, but not to exceed 10 mg qd during the second week on medication. Subsequently, aripiprazole may be increased based on clinical response and tolerability to a maximum of 30 mg qd.

Aripiprazole and placebo will be taken on a QD schedule as outlined in Table 6. Patients in consultation with their physician may elect to take their total daily dose at bedtime based on efficacy and tolerability. From the second week onwards the physician may adjust the dosing up or down for each patient, based on patient tolerability and efficacy. As needed study-prescribed (prn) use of lorazepam will be allowed for the management of affective and anxiety symptoms for the first two weeks of the study; a maximum of 2 mg per day will be allowed during the first week, and a maximum of 1 mg per day will be allowed during the second week. During the second week, the subject must be tapered off the lorazepam. For the final six weeks of the study, no lorazepam will be permitted. Zolpidem (10-20 mg/day) or zaleplon (10-20 mg/day) will be allowed for management of insomnia, and benztropine (0.5-3.0 mg/day) will be allowed for management of extrapyramidal symptoms. The latter three agents will be permitted throughout the study.

All other medications with psychotropic effects are prohibited from 1 week prior to baseline onwards.

TABLE 6

Maximum Daily Dosing Schedule in mgs and Tablet Equivalents (given qd).

| | Visit | Aripiprazole Tablets | Max dose mgs. | Aripiprazole Placebo Tablets | Dosing level |
|---|---|---|---|---|---|
| Week 0-1 | 2nd | 1 | 5 | 1 | Level 1 |
| Week 1-2 | 3rd | 1-2 | 10 | 1-2 | Level 1-2 |
| Week 2-3 | 4th | 1-3 | 15 | 1-3 | Level 1-3 |
| Week 3-4 | 5th | 1-4 | 20 | 1-4 | Level 1-4 |
| Week 4-5 | 6th | 1-5 | 25 | 1 5 | Level 1-5 |
| Week 5-6 | 7th | 1-6 | 30 | 1-6 | Level 1-8 |
| Week 6-7 | 8th | 1-6 | 30 | 1-6 | Level 1-6 |
| Week 7-8 | 9th | 1-6 | 30 | 1-6 | Level 1-6 |
| Week 8-9 | 10th | 1-6 | 30 | 1-6 | Level 1-6 |
| Week 9-10 | 11th | 1-6 | 30 | 1-6 | Level 1-6 |
| Week 10-11 | 12th | 1-6 | 30 | 1-6 | Level 1-6 |
| Week 11-12 | 13th | 1-6 | 30 | 1-6 | Level 1-6 |

TABLE 7

Research Drug Supply Needed In 5 mg Aripiprazole tablets and Matching Placebo.
Please note these calculations are based on visits 1 week apart ± 3 days

| | Visit | Aripiprazole Tablets | Number Needed | Aripiprazole Placebo Tablets | Number Needed |
|---|---|---|---|---|---|
| Week 0-1 | 2nd | 1 | 10 | 1 | 10 |
| Week 1-2 | 2nd | 1-2 | 20 | 1-2 | 20 |
| Week 2-3 | 3rd | 1-3 | 30 | 1-3 | 30 |
| Week 3-4 | 4th | 1-4 | 40 | 1-4 | 40 |
| Week 4-5 | 5th | 1-5 | 50 | 1-5 | 50 |
| Week 5-6 | 6th | 1-6 | 60 | 1-6 | 60 |
| Week 6-7 | 7th | 1-6 | 60 | 1-6 | 60 |
| Week 7-8 | 8th | 1-6 | 60 | 1-6 | 60 |
| Week 8-9 | 9th | 1-6 | 60 | 1-6 | 60 |
| Week 9-10 | 10th | 1-6 | 60 | 1-6 | 60 |
| Week 10-11 | 11th | 1-6 | 60 | 1-6 | 60 |
| Week 11-12 | 12th | 1-6 | 60 | 1-6 | 60 |
| Total | | | 570 | | 570 |
| For sample of 110 patients | | | 62,700 | | 62,700 |

Identification Number Assignments

All patients will receive a 7 digit patient screening I.D. number. The first digit (on the left) is the site number. The first four digits are assigned at screening in sequential order. For example, the first patient presenting for screening at site 1 gets the screening number 1001000, the second, 1002000, etc. The set of last three digits of the I.D. number is the medication number and is assigned in sequential order at the time the patient is randomized to the study drug.

For Example
Site 1          Screening #/Medication #

| 1001 001 | (screened & randomized to medication # 001) |
| 1002 000 | (non-starter: 2nd patient screened only) |
| 1003 002 | (3rd patient screened & randomized to medication # 002) |
| 1004 000 | (non-starter: 4th patient screened only) |
| 1005 003 | (5th patient screened & randomized to medication # 003) |
| 1011 000 | will be the screening number for the 11th patient |

Each site will be assigned a range of numbers for screening (also called the "Confidential I.D. Number"). Study Site 1 will use the screening numbers 1001000-1999000; Study Site 2 will use the screening numbers 2001000-2999000. Study Site 3 will use the screening numbers 3001000-3999000.

Each site will be initially shipped a supply of medication to randomize 10 patients. Additional lots of randomized medication will be shipped to each site in blocks of 5 as needed until a total of 150 patients have completed the study at the combined sites. The 3 digit medication number assigned to the patient is used as the last 3 digits of the randomization number. The randomization number is a 7 digit number.

For the example given above of I.D. assignments for Site 1, the corresponding number for Site 2 is as follows:

For Example
Site 2          Screening #/Medication #

| 2001 001 | (screened & randomized to medication # 001) |
| 2002 000 | (non-starter: 2nd patient screened only) |
| 2003 002 | (3rd patient screened & randomized to medication # 002) |
| 2004 000 | (non-starter: 4th patient screened only) |
| 2005 003 | (5th patient screened & randomized to medication # 003) |
| 2011 000 | will be the screening number for the 11th patient |

Assessments

Screening Visit(s)

The Screening Period will last a minimum of 2 to a maximum of 30 days. At the first screening visit (Visit 0), informed consent will be obtained. The MINI International Neuropsychiatric Interview 6 (MINI 6) (39), (which includes a Suicidality Assessment Module) will be performed to establish whether the patient meets DSM-IV TR (36) criteria for Bipolar disorder I or II or Major Depressive Disorder. The Sheehan Suicidality Tracking Scale (S-STS) (9) will be independently rated by the clinician and the patient at this and each subsequent visit to assess the degree of suicidality. The computer will on which these S-STS ratings are captured at the visit will run a consistency check between the patient and clinician rated S-STS scales and provide an immediate report to the clinician, so that any differences can be re-checked in the interest of patient safety. The CGI-BP (37) and the CGI-S (38) will be performed to establish the severity of bipolar affective symptoms and Major Depressive Disorder, respectively. Subjects will keep a mood chart in between visits to help them follow their affective symptoms. The subject's manic symptoms must be no more than markedly ill (i.e. not severely ill (defined as a mania CGI-BP Score>5)), and his/her illness severity must be at least moderate in severity (a. CGI-S of ≥4) for him/her to be able to continue in the screening process and enter the randomized phase. The screening assessments will include a medical history, a physical exam, height, weight, vital signs, an electrocardiogram (EKG) and laboratory studies (Complete Metabolic Profile, TSH, Free T4, Hemoglobin A1c (HgA1c), Lipid profile, complete blood count (CBC) with differential+platelets, urinalysis, serum pregnancy test and urine drug screen). We will use these assessments to determine whether subjects meet the study eligibility criteria.

Baseline Visit

At baseline (Visit 1), subjects whose screening evaluations continue to meet all inclusion/exclusion criteria may enter the study and be randomized. These evaluations will include repeating the Clinical Global Impression modified for bipolar illness (CGI-BP) (37) and the Clinical Global Impressions Scale—Severity for depressive symptoms (CGI-S) (38) to ensure the subject continues to have no more than moderately severe bipolar affective symptoms and at least moderate Major Depressive Disorder. Baseline ratings will include: the Sheehan Suicidality Tracking Scale (S-STS) (9) to assess suicidality; the Violence Tracking Scale (HTS) to assess Violence; the Hamilton Anxiety Scale (HAM-A) (40) to assess anxiety symptoms; the Young Mania Rating Scale (YMRS) (41) and the Rapid Ideas Scale (RISC) to assess manic symptoms; the BPRS to assess psychotic symptoms; the Irritability Scale, (SIS), the Montgomery Asberg Depression Rating Scale (MADRS) (42) to assess depressive symptoms. Subjects will also be evaluated with the CGI-BP, and the Sheehan Disability Scale (SDS) (43-44). The Family Impact Scale (FIS) will be administered. The Abnormal Involuntary Movement Scale (AIMS) (45), Simpson Angus Scale (SAS) (46), and Barnes Akathisia. Rating Scale (BARS) (47) will be administered to assess for extrapyramidal symptoms. Blood pressure, pulse, and weight, will be measured. Study medication will be dispensed by the Physician Investigator in the form of 5 mg capsules of aripiprazole or matching placebo. The dose range of aripiprazole will be 5 to 10 mg/bid.

Treatment Period

Study visits will occur every week (+3 days) through the eight weeks of treatment. It is expected that the study medication will be gradually increased to an optimal dose during the first several weeks of treatment. The following procedures will be completed at each visit.

- Collect unused medication, perform study drug accountability, and record dosage of study drug used. A subject's unused study medication can be re-dispensed back to the subject.
- Review mood chart and administer the Sheehan Suicidality Tracking Scale (rated by both patient and clinician independently), Clinician Global Improvement-21 point scale (CGI-I-21), Patient Global Improvement –21 point scale (PGI-21) (22) HTS, HAM-A, YMRS, SIS, RISC, BPRS, MADRS, CGI-BP, and SDS ratings.
- Assess and record adverse events. An adverse event is defined as ANY treatment emergent event or as any pre-existing condition that increases in frequency or severity during the course of the study.
- Perform AIMS, SAS, and BARS.
- Obtain blood pressure, pulse, and weight.
- Record concomitant medication use.
- Adjust study medication dose (if necessary) and dispense study drug.

Final Evaluation (Week 8)

The following evaluations will be conducted at the completion of, or early withdrawal from, the 8-week treatment phase. All psychiatric evaluations and all other final study procedures (including a repeat physical exam, EKG, and laboratory studies) will be completed prior to the discontinuation of aripiprazole. The evaluations to be performed are:

- Collect unused study medication, perform study drug accountability, and record dosage of study drug used.
- Review mood chart and perform S-STS (patient and clinician rated), CGI-21, HTS, HAM-A, YMRS, SIS, RISC, BPRS, MADRS, CGI-BP, PGI-21, and SDS ratings.
- Repeat Family Impact Scale (FIS)
- Assess and record adverse events.
- Obtain blood pressure, pulse, weight.
- Perform physical examination, AIMS, SAS, BARS.
- Laboratory studies (Complete Metabolic Profile, Hemoglobin A1c (HgA1c), Lipid profile, CBC with/diff+platelets, Urinalysis, serum pregnancy test).
- Repeat EKG.
- Record concomitant medication use.
- Adjust study medication dose (if necessary) and prescribe drug (if subject has responded and chooses to continue on study medication), or dispense study medication for taper or discontinuation (if subject has not responded or if subject chooses to discontinue study medication for any reason).

Early Termination Visit

In the event of an early termination visit, the usual scales for that patient's weekly visit will be completed. If they terminate at week 4, then the week 4 visit scales are completed.

In addition to the above, the following termination data will be collected:

Physical examination, EKG, laboratory tests (complete metabolic profile, Hemoglobin A1c (HgA1c), lipid profile, CBC with/diff+platelets, urinalysis, serum pregnancy test), Family Impact Scale and Termination Record Form.

Termination Criteria

Subjects will be terminated from the protocol if:

At any time after randomization if their scores on the Sheehan Suicidality Tracking Scale (S-STS) (9) cross the following severity thresholds: >3 on questions 4 or 5 or 6 or 10 or >2 on questions 3a or 7 or 8 or 9 or 11 or in addition any score on the Sheehan Suicidality Tracking Scale (S-STS) if in the judgment of the clinician the suicidality score and risk level are such that it would place the patient at unacceptable risk to continue in the study.

The CGI-BP or CGI-1 rating for change is "very much worse," the YMRS is >21, or the MADRS is >40.

The subject manifests signs of, or, shows evidence of clinically significant suicidality or homicidal ideation that would place them at unacceptable risk to continue in the study. Subjects who are suicidal or homicidal or who require hospitalization will be terminated from the protocol to allow for unencumbered medication changes.

In the absence of the above, subjects will be terminated at the treating psychiatrist's discretion in response to symptoms of sufficient severity that medication changes are warranted as described above.

Subjects may withdraw or be withdrawn from the protocol at any time, for any reason, and such terminations will be documented. All subjects who are terminated from the protocol will receive at least:

3 additional physician visits.

Referrals for other appropriate sources of continued care.

The option to receive open-label effective medications for bipolar disorder as clinically indicated.

Data Collection and Analysis

Electronic Data Capture

All the standardized data captured in this study, except for the history, the laboratory results, the EKG, the physical exam form and the informed and HIPAA forms will be directly recorded at the time of the visit into an electronic data capture database program on a Tablet PC or a Laptop PC, instead of first recording it on to a paper source document and later copying this information into a computer after the visit is completed. All the data capture forms (including scales, structured interviews, medication monitoring, adverse events concomitant medication tracking) for this study will be in the Tablet PCs. The appearance and layout of these forms in the Tablet PC mirrors those traditionally used in paper case report forms. Both the physician and patient will enter their data directly into the Tablet PC at the time of the visit. The database file in the Tablet PC is the source document for this study.

Direct entry electronic data capture (EDC) at the time of the visit, eliminates the need for later data entry by manual key punching into a computer from paper source documents, which is associated with transcription errors, personnel costs and delays. EDC eliminates the problem of missing values and double entries, since the software program in the Tablet PC will not save data from scales, unless all questions are answered. EDC is also programmed to make it impossible to give two responses to one question, where only one response is required.

At the end of each visit, the completed forms can be printed out via the PC wireless card in the Tablet PC and then filed in ring binders for later audit as paper case report forms. The data in the Tablet PC can be sent electronically to a sponsor daily or as often as required. This permits the sponsor to monitor patient enrollment and to monitor adverse events and other data of interest as the study progresses. It substantially reduces the need for site monitors, since monitoring can now be done centrally in-house by the sponsor. At the end of the study, or sooner if needed, the data can be exported directly from the Tablet PC in a form that can be read in Excel or in any statistics package on any other computer.

Data Analysis Plan

The primary comparison of interest is aripiprazole versus placebo using the Sheehan Suicidality Tracking Scale (S-STS)—both clinician rated and patient rated versions. Secondary comparisons include aripiprazole versus placebo for the following measures: the HTS, the HAM-A total score, the psychic and somatic factor scores of the HAM-A, the YMRS total score, the SIS total score, the RISC total score, the BPRS, the MADRS total score, the CGI-21, the PGI-21, the CGI-BP, the FIS, and the work, social, and family disability (SDS) scores. Additional comparisons of interest include the use of adjunctive anxiolytic and hypnotic medication, adherence to study medication, frequency and severity of side effects, and reasons for early termination.

The comparability of treatment groups will be assessed at baseline using parametric statistics for continuous variables (e.g. age) and chi-square or appropriate non parametric statistic, with a continuity correction where indicated, for categorical variables (e.g. gender, previous use of medications).

Efficacy analyses will be based on the intent-to-treat (ITT) population. For the purpose of the study, the ITT population will be defined as all patients who are randomly assigned to treatment, receive at least one dose of study medication, and have at least one post-baseline assessment. For these analyses, missing data will be carried forwards using the last-observation-carried forwards (LOCF) technique. Because of the relatively small size of the sample (30 completed per treatment group) data will be pooled for the three centers. Analyses will also be carried out on the observed cases dataset although these analyses will be considered secondary and supplemental to the primary LOCF analyses.

Repeated measures analysis of covariance (ANCOVA) with baseline scores as a covariate will be the main method for assessing the efficacy of aripiprazole versus placebo for the primary efficacy variable, improvement on the Sheehan Suicidality Tracking Scale (S-STS)—both clinician rated and patient rated versions. Repeated measures analysis of covariance (ANCOVA), with baseline score as a covariate, will be used to compare the efficacy of aripiprazole and placebo for the secondary measures HTS, HAM-A, YMRS, SIS, RISC, MADRS, the CGI-21, the PGI-21, CGI-BP, FIS and SDS scales. Non-parametric statistics (e.g. chi-square with a correction for continuity as indicated) will be employed to examine potential differences in the use of adjunctive anxiolytics and hypnotics, adherence to study medication, and reasons for early termination. All statistical tests will be two-tailed and carried out at an alpha level of 0.05.

An additional analysis of the primary efficacy measures will be conducted using the ETRANK statistical method developed by Richard Entsuah (48). This analysis is included to provide a potentially more sensitive and accurate alternative to the LOCF technique for imputing missing data. The method, is a modification and extension of Gould's (49) ranking approach. It accounts for treatment related (informative censoring) dropouts by using a nonparametric (randomization) method to analyze incomplete repeated-measures data.

With this technique, the observed full data set is used and the pattern, time, reasons and proportion of study withdrawals are incorporated in the statistical method. As Entsuah observes, parametric missing data methods such as Mixed Effects models, Hierarchical Linear Models (HLM), and Imputations methods need to be validated using the assumptions of Missing at Random (MAR) and Missing Completely at Random (MCAR) (50). In contrast, the ETRANK principle is not based on these assumptions. All available data are included, regardless of the reason for early termination from the study, and withdrawals due to adverse events or lack of efficacy are assigned weights, which reflect discontinuation due to improvement, deterioration, and time. Patients who have only baseline measurements who discontinue the study may be included in the computations.

For all numeric variables, assumptions of normality and homogeneity of variance will be assessed by examining normal probability and residual plots. If assumptions of normality and homogeneity of variance are not met, additional analyses will be performed in order to assess the robustness of the conclusions from the primary analysis. This will include investigation of appropriate transformations of the efficacy variable and if an appropriate transformation cannot be identified, non-parametric methods will be used (i.e. the Wilcoxan Rank Sum test).

Safety analyses will be based on all patients receiving medication at baseline (the intent to treat population). Treatment emergent differences in the AIMS, BARS and SAS total scores will be analyzed using one-way analysis of variance at each study week. One-way analysis of variance will also be used to examine weekly differences in vital signs (blood pressure and pulse). A listing of the final dose achieved by each patient and its relationship with rating scales will be provided. In addition, a listing of all adverse experiences, abnormal clinical values, abnormal vital signs (blood pressure and pulse) and termination data will be supplied.

In addition, all efficacy measures over the course of the study will be presented and summarized in graphs and tables. Continuous data will be summarized by means, standard deviations, medians, maximum, minimum and number of patients. Categorical data will be summarized by counts and percentages.

The data for a final endpoint visit will not be included in the efficacy analysis if the date of that visit is ≥12 days from the previous visit at which medication was dispensed. The reason for this is to exclude patients from the endpoint efficacy analyses if they have been off their study medication or out of study medication for at least 2 days at endpoint. All safety data on these patients will be included in the safety analyses. In addition, endpoint efficacy data will be excluded on any patient if their study exit is associated with a protocol violation that could influence efficacy (e.g. taking a benzodiazepine or lithium, or not taking study medication for an extended period).

Power Analysis

This study is exploratory. There are no published studies on suicidality on which to base a power calculation. We chose the sample size of 20 completed patients per treatment arm per disorder studied because it is typically the minimum sample size needed to provide normally distributed data on most of the scales used as outcome measures. This will allow us to analyze the data using parametric analyses, thereby increasing the sensitivity of our analyses. Such a sample size will provide us with data that will permit a power analysis to be run on the results and to calculate the sample size that would be needed to statistically separate active drug from placebo should there be a difference that falls is not statistically significant at p<0.05. This would be helpful in planning future larger studies on suicidality.

Using a simple t-test on change from baseline in standard bipolar I disorder studies to estimate a lower bound on power, the discernible effect sizes are:

| Number of patients per arm | | | |
|---|---|---|---|
| 30 | 25 | 20 | |
| 0.74 | 0.81 | 0.91 | 80% power, statistical significance = 0.05 |

Using a repeated measures analysis, we can expect higher power and to be able to discern smaller effect sizes.

Data Monitoring

The study data will be monitored by the coordinating site at the University of South Florida College of Medicine. All sites will provide the coordinating site with enrollment logs monthly generated from the study software computer program. This will certify work done and will be the basis for the payments monthly to each site. The computer databases of completed work will also be sent to the coordinating site monthly for data monitoring purposes. Status updates of this study will be provided quarterly to the drug sponsor who will not review the case report forms or source documents.

A study start-up teleconference will be held before the study begins, at intervals during the study, and as often as deemed necessary by the coordinating site and at the study close-out. Communication by telephone, fax, e-mail and mail may be used as needed to supplement the teleconferences. The purpose of these teleconferences is to verify 1) adherence to the protocol and 2) the completeness and accuracy of the direct data entry and any additional case report forms, informed consent documents and the clinical stock record. Adequate time for these teleconferences should be allocated by the investigators at each site. Patients' source documents and PC databases will be available for review.

A source document is defined as the place where the original information is first recorded. Most of the data will be directly entered at the time of the visit into a computer database program designed specifically for the study. The database file in the PC will therefore be the source document for almost all of the data in the study. A paper case report form may be a source document if the original information is first recorded there. Unnecessary duplication or re-transcription of data will be avoided where possible so as to insure accuracy and avoid transcription errors. Interim checks on the progress of the study will be made by telephone and by sharing of enrollment logs.

Data Safety Monitoring Board

Because of the unique safety concerns about conducting a study of this kind, a data safety monitoring board will be set up to monitor safety concerns, particularly relating to suicidality. Because the data in this study is being collected in real time the data will be relayed to the chairperson of the data safety monitoring board weekly for review with a summary report of the Sheehan Suicidality Tracking Scale (S-STS) results on individual patients. The data safety monitoring board will be provided a copy of the software and export engine so that they can independently assess any information they need to know to ensure every effort is being made to properly provide for patient safety.

Data Storage and Confidentiality

Back-ups of the data in the computer database file will be made daily and stored at each site. Strict measures will be taken at each site to ensure that tablet PCs or laptops used for the study and the back-up data records are kept under lock and key when not in use to ensure confidentiality. All data will be verified for accuracy before being transferred into a statistical package for data analysis.

Study Sites

This study will be performed at the Depression and Anxiety Disorders Research Institute of University of South Florida College of Medicine, 3515 East Fletcher Avenue, Tampa, Fla., 33613. Although this is planned as a single site study, the University of South Florida College of Medicine might, following consultation with the drug sponsor, subcontract out some of the study to additional sites in the interest of completing the study on the shortest possible timeline.

Laboratory Methods and Facilities

Laboratory tests (Complete Metabolic Profile, CBC with/diff+platelets, Urinalysis and, Urine Drug Screens) will be performed at Quest Diagnostic Inc., 4225 East Fowler Ave, Tampa, Fla. 33617 (for the University of South Florida site) and at (add additional lab information here as needed).

Estimated Period of Time to Complete the Study

It is estimated that this study will take two years to complete.

D. Human Subjects

Subjects will include 120 randomized patients to yield 80 completed outpatients with lifetime bipolar 1 disorder, bipolar 11 disorder, or Major Depressive Disorder by DSM-IV-TR criteria (25), who have more than zero suicidality at the study screening and baseline visits (but whose suicidality is not at a level of severity that will place them at unacceptable risk during the study). Subjects must not be on other psychotropic medications except pm use of lorazepam (for the first 2 weeks of the study), zolpidem, or zaleplon. Subjects must sign a contract not to suicide during the study. Subjects must be ≥18 years of age, be able to provide informed consent, and if female, be postmenopausal, surgically incapable of childbearing, or practicing medically acceptable method(s) of contraception (e.g., hormonal methods, intrauterine device, barrier methods) for at least 1 month prior to study entry and throughout the study. Exclusion criteria include subjects with a current DSM-IV Axis I diagnosis of delirium, dementia, amnesia, or other cognitive disorders, or a substance dependence disorder within the past six months; those with clinically significant suicidal or homicidal ideation; those with serious or unstable general medical illnesses; those who are allergic to or who have demonstrated hypersensitivity to aripiprazole; and females who are pregnant or nursing. Subjects will be recruited from local physician referrals and by advertising.

E. Safety and Subject Protection

A number of measures are included to ensure subject safety in this protocol. The informed consent process allows the subjects to read the informed consent at their leisure. It is then reviewed with the subject by the study coordinator or investigator. The investigator will be available to answer all questions a patient may have about the study and their participation. Only then will the subject sign and date the informed consent document and the HIPAA document.

Investigators and research personnel are available 24 hours/day for emergencies for study subjects. Additional visits to monitor emerging symptoms will be scheduled as needed. Subjects' rights as research subjects will be reviewed at each visit.

To ensure patient comfort, but not confound study results, use of low dose lorazepam may be used for the management of affective and anxiety symptoms during the first two weeks of the study. Zolpidem and Zaleplon may be used on an as needed basis throughout the study for the management of insomnia. The use of all medications will be recorded throughout the study. As previously described, if clinical symptoms require the use of additional psychotropic agents, subjects will be terminated from the study.

A physical examination and routine laboratory monitoring at screening and endpoint will be performed. Weight, blood pressure, pulse, and EPS symptoms will be assessed at each visit.

At the conclusion of the trial, subjects will be offered continuation treatment with aripiprazole or other medications used for the treatment of bipolar disorder or Major Depressive Disorder. The aripiprazole will not be provided free of charge by the drug sponsor. Subjects will be offered at least three additional physician visits to allow for a transition and referral for follow-up care within the clinic or community as appropriate.

1. Risks

The most commonly observed side effects associated with aripiprazole in clinical trials in mood disorders (bipolar I disorder and major depressive disorder) were: akathisia, sedation, restlessness, tremor, insomnia, constipation, fatigue, blurred vision and extrapyramidal disorder.

A rare risk of taking psychiatric drugs like aripiprazole is the risk of developing neuroleptic malignant syndrome (NMS). NMS is a serious, potentially life-threatening disorder that includes symptoms such as: fever, tight muscles, changes in blood pressure and heart rate, as well as changes in thinking and understanding. The risk of neuroleptic malignant syndrome in patients receiving aripiprazole is extremely rare.

If the subject or the study doctor decides to stop a subject's participation in the study due to increased symptoms of bipolar disorder or adverse experiences with study medication, subjects will receive appropriate follow-up treatment as determined by the study doctor. The subject's mental and physical conditions will be monitored closely by the study physician.

2. Pregnancy

Aripiprazole is a Class-C teratogen (FDA Approved Labeling Text). Therefore, women of childbearing potential who are not using adequate contraception and nursing mothers will be excluded from this protocol.

Females who are of childbearing age:
  Must have a negative pregnancy test prior to entering the study.
  Must use an acceptable method of birth control (e.g., hormonal methods, intrauterine devices, harrier methods)
  Must not be breast-feeding.
  Agree to inform the investigator if they suspect that they are pregnant.
  Agree to inform the investigator if they have stopped using the approved form of birth control.

3. Reporting of Serious Adverse Events

Investigators and other site personnel must inform the FDA, via a Medwatch form, of any unexpected and possibly Study Drug-related serious adverse events (SAEs) according to the FDA reporting requirement timelines. The investigator must also inform appropriate drug sponsor representatives of any SAE that occurs in the course of the study within one day (i.e., immediately but no later than the end of the next business day) of when he or she becomes aware of it. The investigator must also report follow-up information on SAEs within one day. A copy off the Medwatch report must be faxed to the drug sponsor at the time at the event is reported to the FDA. Reporting to the FDA is recommended regardless of whether an IND is required for the study.

Additionally, the Investigator shall provide the drug sponsor with a report of all other SAEs that did not qualify for expedited reporting to the FDA (e.g., considered to be expected and/or not related) on at least a quarterly basis in order for the drug sponsor to meet its regulatory reporting obligations.

If the Study is blinded, the Institution shall provide the drug sponsor with the code break information with the initial SAE report or a copy of the randomization schedule at the start of the Study, so that the drug sponsor may un-blind SAE reports to the extent necessary to meet global regulatory reporting requirements.

A complete written SAE report must be sent with a cover page indicating the following:

Drug name (Ability); this is an Investigator Sponsored Study (ISS)

Research (Protocol) and Drug Sponsor Tracking Number (XX_____)

Principal investigator's IND number assigned by the FDA (if applicable)

Principal investigator's full name and address

Unblinding information (if applicable)

Send by way of fax to Ability ISS Safety Representative (XXX) XXX-XXXX.

If a non-serious AE becomes serious, this and other relevant follow-up information must also be provided to the drug sponsor and the FDA within one day as described above. All SAEs have to be reported to the drug sponsor, whether or not considered causally related to the investigational product. All SAEs will be documented. The investigator is responsible for informing the IRB and/or the regulatory authority of the SAE as per local requirements.

4. Definitions for Adverse Event Reports

A serious adverse event is defined as one that satisfies any of the following criteria:

Results in death is immediately life-threatening requires in-patient hospitalization or prolongation of existing hospitalization results in persistent or significant disability or incapacity is a congenital abnormality or birth defect is an important medical event that may jeopardize the patient or may require medical intervention to prevent one of the outcomes listed above Serious adverse events are further explained as follows:

any death resulting from an adverse event occurring during the trial period or within 30 days after the last dose of the trial drug.

the subject must have been at an immediate risk of dying from the adverse event as it occurred. This does not include events that might have caused death if they had occurred in a more serious form (e.g., drug-induced hepatitis that resolves without hepatic failure).

any adverse event resulting in hospital admission and usually an overnight stay. Prolongs hospitalization means delayed planned or anticipated discharge date (again usually by at least one overnight stay). This does not include hospitalization for elective surgery for a condition that was present prior to trial entry and whose clinical course has not changed after exposure to the trial drug.

any adverse event resulting in impairment, damage or disruption in the subject's body function, structure or both, physical activities or quality of life.

any adverse event resulting in a condition which requires medical or surgical intervention to prevent permanent impairment of a body function or permanent damage to a body structure of the subject. Examples of this can include procedures such as blood transfusion or catheterization. However, discontinuation of the trial drug, or routine administration of prescription medications or changes in their dosages, should not be considered as medical intervention.

if there are suspicions that exposure of either parent to the trial drug resulted in an adverse outcome in the offspring 5. Guide to Interpreting the Causality Question Time Course. Exposure to suspect drug. Has the subject actually received the suspect drug? Did the AE occur in a reasonable temporal relationship to the administration of the suspect drug?

Consistency with known drug profile. Was the AE consistent with the previous knowledge of the suspect drug (pharmacology and toxicology) or drugs of the same pharmacological class? OR could the AE be anticipated from its pharmacologic properties?

De-challenge experience. Did the AE resolve or improve on stopping or reducing the dose of the suspect drug?

No alternative cause. The AE cannot be reasonably explained by another etiology such as the underlying disease, other drugs, other host or environmental factors.

Re-challenge experience. Did the AE reoccur if the suspected drug was reintroduced after having been stopped? The drug sponsor would not normally recommend or support a re-challenge.

Laboratory tests. A specific laboratory investigation (if performed) has confirmed the relationship.

A "reasonable possibility" could be considered to exist for an AE where one or more of these factors exist.

In contrast, there would not be a "reasonable possibility" of causality if none of the above criteria apply or where there is evidence of exposure and a reasonable time course but any de-challenge (if performed) is negative or ambiguous or there is another more likely cause of the AE.

In difficult cases, other factors could be considered such as:

is this a recognized feature of overdose of the drug?

is there a known mechanism?

Ambiguous cases should be considered as being a "reasonable possibility" of a causal relationship unless further evidence becomes available to refute this. Causal relationship in cases where the disease under study has deteriorated due to lack of effect should be classified as no reasonable possibility.

Life Threatening

"Life-threatening" means that the subject was at immediate risk of death from the AE as it occurred or it is suspected that use or continued use of the product would result in the subject's death. "Life-threatening" does not mean that had an AE occurred in a more severe form it might have caused death (e.g., hepatitis that resolved without hepatic failure).

Hospitalization

Out-patient treatment in an emergency room is not in itself a serious AE, although the reasons for it may be (e.g., bronchospasm, laryngeal edema). Hospital admissions and/or surgical operations planned before or during a study are not considered AEs if the illness or disease existed before the subject was enrolled in the study, provided that it did not deteriorate in an unexpected way during the study, 6. Important Medical Event or Medical Intervention Medical and scientific judgment should be exercised in deciding whether a case is serious in situations where important medical events may not be immediately life-threatening or result in death, hospitalization, disability or incapacity but may jeopardize the subject or may require medical intervention to prevent one or more outcomes listed in the definition of serious. These should usually be considered as serious.

Simply stopping the suspect drug does not mean that it is an important medical event; medical judgment must be used.

Examples of such events are:

Angioedema not severe enough to require intubation but requiring iv hydrocortisone treatment Hepatotoxicity caused by paracetamol (acetaminophen) overdose requiring treatment with N-acetylcysteine Intensive treatment in an emergency room or at home for allergic bronchospasm Blood dyscrasias (e.g., neutropenia or anemia requiring blood transfusion, etc.) or convulsions that do not result in hospitalization Development of drug dependency or drug abuse 7. Benefits The benefits of this study would include a thorough psychiatric evaluation; a thorough medical evaluation; the possibility that either of the study medications might alleviate suicidal symptoms or behavior, manic, depressive, and/or anxiety symptoms in subjects with bipolar disorder or Major Depressive Disorder; help and referral for additional treatment if needed; and the chance to contribute to a scientific investigation which may be of benefit to patients with Bipolar Disorders or Major Depressive Disorder in the future.

LITERATURE CITED

1. Kessler R C, Rubinow D R, Holmes C, et al. The epidemiology of DSM-III-R bipolar I disorder in a general population survey. Psychological Med 1997; 27:1079-1089.
2. Angst, F., Stassen, H. H., Clayton, P. J., and Angst, J. (2002). Mortality of patients with mood disorders: Follow-up over 34-38 years. J Affect Disord, 68(2), 167-181.
3. Mann J J, Brent A, Anango V. The neurobiology and genetics of suicide and attempted suicide: a focus on the serotonergic system. Neuropsychopharmacology. 24(5): 467-477, 2001
4. Mann J J & Arango V Neurobiology of suicide and attempted suicide. Chapter in Suicide: an unnecessary death. Wasserman D (ed.) Martin Dunitz. London. 2001: 29-34
5. Arango V, Mann J J. Relevance of serotonergic post mortem studies to suicidal behavior. Int Rev Psychiat 4:131-140. 1992
6. Gershon E S. Genetics. In Goodwin F K, Jamison K R (eds), Manic Depressive Illness. New York, Oxford: Oxford University Press, pp. 373-401. 1990.
7. Roy A. Genetic and biologic risk factors for suicide in depressive disorders. Psychiat Quart 64:345-358. 1993.
8. Roy A, Segal N L, Sarchiapone M. Attempted suicide among living co-twins of twin suicide victims. Am J Psychiat 152:1075-1076.1995.
9. Colic V, Stock E G; Pultz J, Marcus R, and Sheehan D V Sheehan (2009). Sheehan Suicidality Tracking Scale (S-STS): Preliminary Results from a Multicenter Clinical Trial in Generalized Anxiety Disorder (2009) Psychiatry 6(1):26-31.
10. Posner K, Oquendo, M, Gould M, Stanley B, Davies M. (2007). Columbia Classification Algorithm of Suicide Assessment (C-CASA): Classification of Suicidal Events in the FDA's Pediatric Suicidal Risk Analysis of Antidepressants. Am J Psychiatry 164:1035-1043.
11. Posner K, Brent D, Lucas, C, et al. Columbia-Suicide Severity Rating Scale (C-SSRS). New York, N.Y.: Columbia University/New York State Psychiatric Institute; 2006.
12. Bertolote J M. Suicide in the World: an epidemiological overview 1959-2000. Chapter in Suicide: an unnecessary death. Wasserman D (ed.) Martin Dunitz. London. 2001: 3-10).
13. Rettersol N & Mehlum L. Attempted suicide as a risk factor for suicide; treatment and follow up. Chapter in Chapter in Suicide: an unnecessary death. Wasserman D (ed.) Martin Dunitz. London. 2001:125-131)
14. Khan, A., Khan, S., Kolts, R., and Brown, W. A. (2003). Suicide rates in clinical trials of SSRIs, other antidepressants, and placebo: Analysis of FDA reports. Am J Psychiatry, 160(4), 790-792.
15. Goodwin, F. K., Fireman, B., Simon, G. E., Hunkeler, E. M., Lee, J., and Revicki, D. (2003). Suicide risk in bipolar disorder during treatment with lithium and divalproex. JAMA, 290(11), 1467-1473.
16. Baldessarini, R. J, Tondo, L., and Hennen, J. (2001). Treating the suicidal patient with bipolar disorder: Reducing suicide risk with lithium. Ann N Y Acad Sci, 932:24-38; discussion 39-43.
17. Baldessarini, R. J., Tondo, L., and Hennen, J. (1999). Effects of lithium treatment and its discontinuation on suicidal behavior in bipolar manic-depressive disorder. J Clin Psychiatry, 60(Suppl. 2), 77-84.
18. Bowden C L, Grunze H, Mullen J, Brecher M, Paulsson B, Jones M, Vågerö M, Svensson K. A randomized, double-blind, placebo-controlled efficacy and safety study of quetiapine or lithium as monotherapy for mania in bipolar disorder. J Clin Psychiatry. 2005 January; 66(1):111-21.
19. Jones M, Huizar K. Quetiapine monotherapy for mania associated with bipolar disorder. Program and abstracts of the Fifth International Conference on Bipolar Disorder; Jun. 12-14, 2003; Pittsburgh, Pa.
20. Paulsson B, Huizar K. Quetiapine monotherapy for the treatment of bipolar mania. Programs and abstracts of the 5th International Conference on Bipolar Disorder; Jun. 12-13, 2003; Pittsburgh, Pa.
21. Sachs G, Chengappa K N R, Suppes T, et al. Quetiapine with lithium or divalproex for the treatment of bipolar mania: a randomized, double-blind, placebo-controlled study. Bipolar Disord. 2004; 6:213-223.
22. Delbello M P, Schwiers M L, Rosenberg H L, Strakowski S M. A double-blind, randomized, placebo-controlled study of quetiapine as adjunctive treatment for adolescent mania. J Am Acad Child Adolesc Psychiatry. 2002 October; 41(10):1216-23.
23. Calabrese J R, Keck P E, Macfadden, W, Minkwitz M M., Ketter T A, Weisler R H, Cutler A J., McCoy R, Wilson E., and Mullen J. A Randomized, Double-Blind, Placebo-Controlled Trial of Quetiapine in the Treatment of Bipolar I or II Depression. Am J Psychiatry. 2005; 162:1351-1360.
24. Macfadden W, Calabrese J, McCoy R et al. Anti-anxiety effects analysis of quetiapine in bipolar depression. Abstract presented at CINP, Paris, 2004.
25. Emsley R A, Buckley P, Greenwood M R Differential Effect of Quetiapine on Depressive Symptoms in Patients with Partially Responsive Schizophrenia, Jnl. Psychopharmacology. 2003; 17(2): 210-215.
26. Keck P E Jr, McElroy S L. Redefining mood stabilization. J Affect Disord. 2003; 73:163-169
27. McElroy S L, Keck P E, Jr. Pharmacological agents for the treatment of acute bipolar mania. Biol Psychiatry 2000; 48:539-557
28. Suppes T, Baldessarini R, Faedda G, Tohen M. Risk of recurrence following discontinuation of lithium treatment in bipolar disorder. Arch Gen Psychiatry. 1991; 48:1082-1088.
29. Suppes T, Webb A, Paul B, Carmody T, Kraemer H and Rush J. Clinical outcome in a randomized 1-year trial of clozapine versus treatment as usual for patients with treatment-resistant illness and a history of mania. Am J Psychiatry 156:1164-1169, August 1999

30. Suppes T, Dennehy E B, Rush A J et al. The Texas Medication Algorithm Project: clinical results for patients with a history of mania. J Clin Psychiatry. 2003; 64:370-82.

31. Suppes, T; Swann, A C; Dennehy, E B; et al, Texas Medication Algorithm Project: Development and Feasibility Testing of a Treatment Algorithm for Patients With Bipolar Disorder. Year Book of Psychiatry & Applied Mental Health. 2003; 64:378-381, 2003.

32. Suppes T, Dennehy E B, Hirschfeld R M A, et al. Texas Consensus Conference Panel on Medication Treatment of Bipolar Disorder. The Texas Implementation of medication algorithms: update to the algorithms for treatment of bipolar I disorder. J Clin Psychiatry. 2005; 66:870-886.

33. Suppes, Trisha M D, PhD; Mintz, Jim PhD; McElroy, Susan L. MD; Altshuler, Lori L. MD; Kupka, Ralph W. MD; Frye, Mark A. MD; Keck, Paul E. Jr MD; Nolen, Willem A. MD; Leverich, Gabriele S. MSW; Grunze, Heinz M D; Rush, A. John M D; Post, Robert M. MD Mixed Hypomania in 908 Patients With Bipolar Disorder Evaluated Prospectively in the Stanley Foundation Bipolar Treatment Network: A Sex-Specific Phenomenon. Archives of General Psychiatry. 62(10):1089-1096, October 2005.

34. Houston J P, Ahl J, Meyers A L, Kaiser C J, Tohen M, Baldessarini R J. Reduced suicidal ideation in bipolar I disorder mixed-episode patients in a placebo-controlled trial of olanzapine combined with lithium or divalproex. J Clin Psychiatry. 2006; 67:1246-1252.

35. Ciapparelli A, Dell'Osso L, Pina S, Chiavacci M C, Fenzi M, Cassan o G B. Clozapine for treatment refractory schizophrenia, schizoaffective disorder and psychotic bipolar disorder: a 24 month naturalistic study. J Clin Psychiatry 2000; 61(5):329-334.

36. Diagnostic and Statistical Manual of Mental Disorders, Fourth Edition Text Revision. American Psychiatric Association, 2000.

37. Spearing M K, Post R M, Leverich G S, et al. Modification of the Clinical Global Impressions Scale for use in bipolar illness (BP): the CGI-BP. Psychiatry Res 1997; 73: 159-171.

38. Guy W. ECDEU Assessment Manual for Psychopharmacology. Revised for Mental Health, DHEW Pub. (ADM). National Institute for Mental Health, Rockville, Md., 1976.

39. Sheehan D V, Lecrubier Y, Harnett-Sheehan K, Amorim P, Janays J, Weiller E, Hergueta T, Baker R, Dunbar G: The Mini International Neuropsychiatric Interview (M.I.N.I.): The Development and Validation of a Structured Diagnostic Psychiatric Interview. J. Clin Psychiatry, 1999; 59(suppl 20):22-33.

40. Hamilton, M. The assessment of anxiety states by rating. Br J Med Psychol 1959; 32:50-55

41. Young R C, Biggs J T, Ziegler V E, et al. A rating scale for mania: reliability, validity, and sensitivity. Br J Psychiatry 1978; 133: 429-435.

42. Montgomery S, Asberg M. A new depression scale designed to be sensitive to change. British J Psychiatry. 1979; 134:383-9.

43. Leon A C, Shear M K, Portera L, Kleiman G L. Assessing impairment in patients with panic disorder: the Sheehan Disability Scale. Soc Psychiatry Psychiatr Epidemiol 1992; 27:78-82

44. Sheehan D V, Sheehan K H, Raj B A. The Measurement of Disability. International Clinical Psychopharmacology. 1996; 11(Suppl 3):89-95.

45. National Institute of Mental Health. AIMS (Abnormal Involuntary Movement Scale). Psychopharmacol Bull 1985; 21:839-843

46. Simpson G M, Angus J W S. A rating scale for extrapyramidal side effects. Acta Psychiatry Scand 1970; 212: S11-S19.

47. Barnes T R. A rating scale for drug induced akathisia. Br J Psychiatry 1989; 154: 672-676.

48. Entsuah A R. Randomization procedures for analyzing clinical trail data with treatment related withdrawals. Communications in Statistics: Theory and Method, 1990: 19:3859-3880; Entsuah R. ETRANK: a ranking procedure for handling missing data in clinical trials: application to venlafaxine extended-release depression clinical trial. J Biopharm Stat. 1996: 6:457-475.

49. Gould A L. A new approach to the analysis of clinical drug trials with withdrawals. Biometrics. 1980: 36:721-727.

50. Little R J A, Rubin D B. Statistical Analysis with Missing Data. New York: John Wiley and Sons, Inc.: 1987

51. McIntyre R S, Hirschfeld R, Calabrese J, Panagides J. Asenapine in bipolar disorder: an overview of clinical trials in the Olympia Program. Poster presented at the 63rd Annual Scientific Convention and Meeting of the Society of Biological Psychiatry; May 1-3, 2008. Washington, D.C.

52. McIntyre R S, Cohen M, Zhao Jun, Panagides J, Szegedi A. Double-blind extension studies of asenapine in patients with bipolar mania. Poster presented at the 21st Congress of the European College of Neuropsychopharmacology; Aug. 30-Sep. 3, 2008. Barcelona, Spain.

The invention claimed is:

1. A method of treating suicidality in a subject in need thereof, comprising administering to the subject an effective amount of mecamylamine or TC-5214.

2. The method of claim 1, wherein the subject has suicidal thoughts and is at risk of committing suicide.

3. The method of claim 1, wherein the subject has tried to commit suicide or has a history of suicide attempts.

4. The method of claim 1, wherein the subject is further suffering from ambulatory bipolar disorder, schizophrenia, or both.

5. The method of claim 1, wherein the subject is identified as suffering from suicidality using a suicidality tracking scale capable of direct mapping to the Columbia Classification Algorithm for Suicide Assessment (C-CASA).

6. The method of claim 1, wherein the subject is identified as suffering from suicidality using the Sheehan Suicidality Tracking Scale (S-STS) or Columbia Suicide Severity Rating Scale (C-CRS).

7. The method of claim 1, wherein the subject is identified as having suicidality symptoms of more than zero as measured by the Sheehan Suicidality Tracking Scale (S-STS) prior to said administering.

8. The method of claim 1, wherein the subject has an abnormally low brain-derived neurotrophic factor (BDNF), or cerebrospinal fluid (CSF) monoamine metabolite, concentration prior to said administering.

9. The method of claim 8, wherein the monoamine metabolite is 5-hydroxyinoleacetic acid (5-HIAA).

10. The method of claim 1, wherein the subject has a polymorphism in the tryptophan hydroxylase gene in intron 7.

11. The method of claim 1, wherein the subject has had a major depressive episode.

12. The method of claim 1, wherein the subject is suffering from bipolar depression.

13. The method of claim 1, wherein the subject is suffering from an anxiety disorder or anxiety symptoms.

14. The method of claim 1, wherein the subject is further suffering from a disorder selected from the group consisting of bipolar disorder, panic disorder, social anxiety, post-traumatic stress disorder (PTSD), substance dependence/abuse, eating disorder, obsessive compulsive disorder (OCD), schizophrenia, schizo-affective disorder, schizophrenoform disorder, Huntington's disease, early Alzheimer's disease, and Parkinson's disease.

15. The method of claim 1, wherein the mecamylamine or TC-5214 is administered as a monotherapy.

16. The method of claim 1, wherein no mood stabilizing, antidepressant, antipsychotic, or anxiolytic medication, other than an nAChR inhibitor, is administered to the subject concurrently with the mecamylamine or TC-5214, or administered less than one week prior to administration of the mecamylamine or TC-5214.

17. The method of claim 1, wherein the subject is administered a mood stabilizing, antidepressant, antipsychotic, or anxiolytic medication at least one week, prior to administration of the mecamylamine or TC-5214.

18. The method of claim 1, wherein both mecamylamine and TC-5214 are administered to the subject.

19. The method of claim 1, wherein the mecamylamine is administered to the subject.

20. The method of claim 1, wherein the subject has not suffered a major depressive episode.

21. The method of claim 1, wherein the subject is not suffering from major depressive disorder.

22. The method of claim 1, wherein the subject is not suffering from bipolar disorder.

23. The method of claim 1, wherein the suicidality is thereby eliminated.

24. The method of claim 1, wherein the suicidality is non-drug-induced.

25. The method of claim 1, wherein the TC-5214 is administered to the subject.

* * * * *

UNITED STATES PATENT AND TRADEMARK OFFICE
CERTIFICATE OF CORRECTION

PATENT NO. : 9,180,191 B2
APPLICATION NO. : 13/502239
DATED : November 10, 2015
INVENTOR(S) : David Vincent Sheehan et al.

Page 1 of 4

It is certified that error appears in the above-identified patent and that said Letters Patent is hereby corrected as shown below:

IN THE SPECIFICATION

Column 1,
Lines 6-12,
"CROSS-REFERENCE TO RELATED APPLICATION
The present application claims the benefit of U.S. Application Ser. No. 61/252,343, filed Oct. 16, 2009, which is hereby incorporated by reference herein in its entirety, including any figures, tables, nucleic acid sequences, amino acid sequences, and drawings."

should read

--CROSS-REFERENCE TO RELATED APPLICATIONS
This application is the U.S. National Stage of International Application No. PCT/US2010/052949, filed October 15, 2010, which claims the benefit of U.S. Application Serial No. 61/252,343, filed October 16, 2009, each of which is hereby incorporated by reference herein in its entirety, including any figures, tables, nucleic acid sequences, amino acid sequences, and drawings.--.

Column 2,
Line 50, "may he" should read --may be--.

Column 9,
Line 15, "*Curr. Mel. Med.*," should read --*Curr. Mol. Med.*,--.
Line 34, "Dhannacon, Inc." should read --Dharmacon, Inc.--.

Column 19,
Line 47, "wit a score" should read --with a score--.

Signed and Sealed this
Fifth Day of April, 2016

Michelle K. Lee
*Director of the United States Patent and Trademark Office*

IN THE SPECIFICATION

Column 20,
Line 2, "1.0 plus" should read --10 plus--.

Column 28,
Line 31, "1.D. assignments" should read --I.D. assignments--.

Column 29,
Line 31, "CGT-BP" should read --CGI-BP--.

Column 38,
Lines 43-48 (Table 2),

"
|        | Visit    |       |    |            |
|--------|----------|-------|----|------------|
| Screen | Baseline | 3-13  | 14 |            |
|        | Week     |       |    | Early      |
| −1     | 0        | 1-11  | 12 | Termination |
"

should read

--
| Visit | Screen | Baseline | 3-13 | 14 | Early |
|-------|--------|----------|------|----|-------|
| Week  | -1     | 0        | 1-11 | 12 | Termination |
--.

Column 39,
Line 50, "bipolar 1" should read --bipolar I--.

Column 40,
Lines 4-8 (Table 2),

"
|        | Visit    |       |    |            |
|--------|----------|-------|----|------------|
| Screen | Baseline | 3-13  | 14 |            |
|        | Week     |       |    | Early      |
| −1     | 0        | 1-11  | 12 | Termination |
"

should read

--
| Visit | Screen | Baseline | 3-13 | 14 | Early |
|-------|--------|----------|------|----|-------|
| Week  | -1     | 0        | 1-11 | 12 | Termination |
--.

Column 45,
Line 46, "Hemoglobin Ale (HgA1c)," should read --Hemoglobin A1c (HgA1c),--.

Column 47,
Line 15, "analysis. Repeated" should read --analysis.
                                              Repeated--.

CERTIFICATE OF CORRECTION (continued)
U.S. Pat. No. 9,180,191 B2

IN THE SPECIFICATION

Column 47,
Line 25, "PG1-21" should read --PGI-21--.

Column 49,
Line 60, "DSM-IV Axis 1" should read --DSM-IV Axis I--.

Column 54,
Lines 25-29 (Table 5),

"

| | Visit | | | |
|---|---|---|---|---|
| Screen | Baseline | 3-13 | 14 | |
| | Week | | | Early |
| -1 | 0 | 1-11 | 12 | Termination |

,, should read

--

| Visit | Screen | Baseline | 3-13 | 14 | Early |
|---|---|---|---|---|---|
| Week | -1 | 0 | 1-11 | 12 | Termination |

--.

Column 55,
Line 60, "bipolar 1 or II" should read --bipolar I or II--.

Column 56,
Lines 3-7 (Table 5),

"

| | Visit | | | |
|---|---|---|---|---|
| Screen | Baseline | 3-13 | 14 | |
| | Week | | | Early |
| -1 | 0 | 1-11 | 12 | Termination |

"

should read

--

| Visit | Screen | Baseline | 3-13 | 14 | Early |
|---|---|---|---|---|---|
| Week | -1 | 0 | 1-11 | 12 | Termination |

--.

Column 59,
Line 48, Table 6, Week 5-6, last column, "Level 1-8" should read --Level 1-6--.

Column 67,
Line 12-13,
"bipolar 1 disorder, bipolar 11 disorder" should read --bipolar I disorder, bipolar II disorder--.

CERTIFICATE OF CORRECTION (continued)
U.S. Pat. No. 9,180,191 B2

IN THE SPECIFICATION

Column 68,
Line 36, "harrier methods" should read --barrier methods--.

Column 69,
Line 3, "(Ability)" should read --(Abilify)--.
Line 12, "Ability ISS" should read --Abilify ISS--.

Column 71,
Line 47, "Colic" should read --Coric--.

Column 73,
Line 48, "Janays" should read --Janavs--.
Line 61, "Kleiman" should read --Klerman--.